US008383126B2

(12) United States Patent
Mukamolova et al.

(10) Patent No.: US 8,383,126 B2
(45) Date of Patent: Feb. 26, 2013

(54) BACTERIAL PHEROMONES AND USES THEREOF

(75) Inventors: Galina V. Mukamolova, Moscow Region (RU); Arseny S. Kaprelyants, Moscow (RU); Danielle I. Young, Ceredigion (GB); Douglas B. Kell, Ceredigion (GB); Michael Young, Ceredigion (GB)

(73) Assignee: University of Wales, Aberstwyth, Aberystwyth, Ceredigion (GB)

( * ) Notice: Subject to any disclaimer, the term of this patent is extended or adjusted under 35 U.S.C. 154(b) by 209 days.

(21) Appl. No.: 11/978,257

(22) Filed: Oct. 29, 2007

(65) Prior Publication Data

US 2008/0206269 A1 Aug. 28, 2008

Related U.S. Application Data

(62) Division of application No. 09/445,289, filed as application No. PCT/GB98/01619 on Jun. 3, 1998.

(30) Foreign Application Priority Data

Jun. 4, 1997 (GB) .................................. 9711389.8
May 27, 1998 (GB) .................................. 9811221.2

(51) Int. Cl.
*A61K 39/02* (2006.01)
*A61K 39/04* (2006.01)
*A61K 38/00* (2006.01)
*C07K 1/00* (2006.01)

(52) U.S. Cl. ............... 424/190.1; 424/234.1; 424/248.1; 530/350; 530/300; 530/825; 514/1.1

(58) Field of Classification Search ........................ None
See application file for complete search history.

(56) References Cited

U.S. PATENT DOCUMENTS 6,331,318 B1 12/2001 Milstein
6,649,169 B2 11/2003 Dowling et al.
7,452,869 B2 11/2008 Hellner et al.
7,595,383 B1 * 9/2009 Gennaro et al. ............. 536/23.7
2008/0206269 A1 8/2008 Mukamolova et al.

OTHER PUBLICATIONS

Skolnick et al. Trends in Biotechnology 18: 34-39, 2000.*
Illustrated Stedman's Medical Dictionary. 24th Edition, Williams and Wilkins, London. p. 707 (1982).
Mukamalova et al. Arch. Microbiol. 172: 9-14 (Jul. 1999).
Mukamalova et al. Antonie can Leeuwenhoek 67: 289-295 (1995).
U.S. Appl. No. 09/445,289, Mukamalova et al.
Badcock, K. et al., "Hypothetical 17.7 KD protein," TRPRO Database entry 033049, Jan. 1, 1998, Accession No. 033049.
Cole, S.T. et al. "Deciphering the biology of *Mycobacterium tuberculosis* from the complete genome sequence," Nature 393(6685): 537-44 (1998).
Cole, S.T. et al., "Hypothetical 15.7 KD protein," TRPRO Database entry P71755, Feb. 1, 1997, Accession No. P71755.
Cole, S.T. et al., "Hypothetical 18.8 KD protein," TRPRO Database entry 007747, Jul. 1, 1997, Accession No. 007747.
Cole, S.T. et al., "Hypothetical 38.1 KD protein," TRPRO Database entry 005594, Jul. 1, 1997, Accession No. 005594.
Eiglmeir, K. et al. "Use of an ordered cosmid library to deduce the genomic organization of *Mycobacterium leprae*," Mol. Microbiol. 7(2): 197-206 (1993).
Kaprelyants, Arseny S. and Kell, Douglas B. et al., "Do bacteria need to communicate with each other for growth?" Trends in Microbiology 4(6):237-42 (1996).
Kaprelyants, Arseny S. et al., "Estimation of dormant *Micrococcus luteus* cells by penicillin lysis and by resuscitation in cell-free spent culture medium at high dilution," FEMS Microbiology Letters 115(2-3):347-52 (1994).
Kunst, F. et al, "Cell wall-binding protein homolog yocH-*Bacillus subtilis*" PIR Database entry E69901, Dec. 5, 1997, accession No. E69901.
Kunst, F. et al. "The complete genome sequence of the Gram-positive bacterium *Bacillus subtillis*," Nature 390:249-56 (1997).
International Preliminary Examination Report dated Sep. 14, 1999, from International Patent Application No. PCT/GB98/01619 (filed Jun. 3, 1998).
International Search Report dated Nov. 4, 1998, from International Patent Application No. PCT/GB98/01619 (filed Jun. 3, 1998).
Jing, ER; "Study of resuscitating effect for dormant tuberculosis by recombinant resuscitation promoting factor (Rpf) proteins." *China Journal of Modern Medicine*. (19:17) 2640-43. Sep. 2009.
Harlow et al. In: Antibodies: A Laboratory Manual. Cold Spring Harbor Laboratory, Chapter 5, 60-71, 1988.
Lyristis, M. et al, "Hypothetical protein 1-*Clostridium perfringens* (fragment), " PIR Database entry S49552, No. 29, 1995, Accession No. S49552.
Lyristis, Michael et al. "Identification and molecular analysis of a locus that regulates extracellular toxin production in *Clostridium perfringens*," Mol. Microbiol. 12(5): 761-77 (1994).
Mukamolova, Galina V. et al. "A bacerial cytokine," Proc. Natl. Acad Sci. USA 95(15): 8916-21 (1998).
Ogasawara, N. et al. "Hypothetical 47.7 KD protein in meta-ksga intergenic region," SWISSPROT Database entry Yabe-Bacsu, Oct. 1, 1994, Accession No. P37546.
Ogasawara, Naotake et al. "Systemic Sequencing of the 180 Kilobase Region of the *Bacillus subtilis* Chromosome containing the replication Origin." DNA Research 1:1-14 (1994).
Parker, W.D. et al. "Cytochrome oxidase mutuations aiding diagnosis of sporadic Alzheimer's disease, Sequence 29 from Patent US 5565323," Genbank Accession No. 127393, 1997.
Votyakova, Tatyana V. et al., "Influence of Viable Cells on the Resuscitation of Dormant Cells in *Micrococcus luteus* cultures held in an Extended Stationary Phase: The Population Effect," Applied and Environmental Microbiology 60(9): 3284-91 (1994).
Skolnick, et al. Trends in Biotechnology. 18: 34-39 (2000).
Rudinger, et al. Peptide Hormones. (Ed) JA Parsons. University Park Press, pp. 1-7 (1976).
Houghten, et al. Vaccines. Cold Spring Harbor Laboratory. 86: 21-25 (1986).
The Webster's New Riverside University Dictionary, p. 933 (1984).

* cited by examiner

*Primary Examiner* — S. Devi
(74) *Attorney, Agent, or Firm* — McCarter & English, LLP; Maria Laccotripe Zacharakis

(57) ABSTRACT

RP-factors, their cognate receptors, convertases, respective genes and inhibitors or mimetics thereof are described. In particular, antibodies, pharmaceutical compositions and (therapeutic, diagnostic) methods based on the RP-factors and their receptors/convertases are described.

38 Claims, 23 Drawing Sheets

FIG. 1A

| FIG. 1A-1 |
|---|
| FIG. 1A-2 |
| FIG. 1A-3 |

```
SEQ ID NO: 1  MtubZ94752  mlrlvvqalllvlafaggyavaacktvtltvdgtamrvttmksrvidive  50

              MtubZ94752  engfsvddrddlypaagvqvhdadtivlrrsrplqisldghdakgvwtta 100

              MtubZ94752  stvdealaqlamtdtapaaasrasrvplsgmalpvvsaktvqlndgglvr 150

              MtubZ94752  tvhlpapnvagllsaagvpllqsdhvvpaatapivegmqiqvtrnrikkv 200
SEQ ID NO: 2  MtubMTV008  -----------------mpvgwlwrartakgttlknarttliaaaiaqt  32

SEQ ID NO: 3  Mlepl04666  ------------------------------------------msesyrkl   8
SEQ ID NO: 4  MtubMTV043  -----------------------------------------msgrhrkpt   9
              MtubZ94752  terlplppnarrvedpemnmsrevvedpgvpgtqdvtfavaevngvetgr 250
SEQ ID NO: 36 MlutZ96935  -----------------------------------------mtlfttsat   9
SEQ ID NO: 5  MlepL01095  --------------------------------------mpgemldvrklc  12
SEQ ID NO: 6  MtubU38939  ------------mhplpadhgrsrcnrhpisplslignisatsgdmssmt  38
SEQ ID NO: 7  MtubZ81368  -------------------------------mtpgllttagagrprdrca  19
              MtubMTV008  lvttspagianaddagldpnaaagpdavgfdpnlppapdaapvdtppape  82
```

FIG. 1A-1

```
SEQ ID NO: 8 Scoeli6C12S  ---irtaavtlvaatalgatgeavaapsaplrtDWDAIAACESSGNWQAN   25
             Mlep104666   ttssiivakitftgamldgsialagqaspatdsEWDQVARCESGGNWSIN   58
             MtubMTV043   tsnvsvakiaftgavlgggiamaaqataatdgEWDQVARCESGGNWSIN    59
             MtubZ94752   lpvanvvvtpaheavvrvgtkpgtevppvidgsIWDAIAGCEAGGNWAIN  300
             MlutZ96935   rsrratasivagmtlagaaavgfsapagaatvdTWDRLAECESNGTWDIN   59
             MlepL01095   klfvksavvsgivtasmalststgmanavprePNWDAVAQCESGRNWRAN   62
             MtubU38939   riakpliksamaaglvtasmslstavahagpsPNWDAVAQCESGGNWAAN   88
             MtubZ81368   rivctvfietavvatmfvallglstisskaddIDWDAIAQCESGGNWAAN   69
             MtubMTV008   dagfdpnlppplapdflsppaeeappvpvaysVNWDAIAQCESGGNWSIN  132
                                                          ***.* *******  *

             Scoeli6C12S  TGNGYYGGLQFARSSWIAAGGLKYAPRADLATRGEQIAVAERLARLQGMS   75
             Mlep104666   TGNGYLGGLQFSQGTWASHGGGEYAPSAQLATREQQIAVAERVLATQGSG  108
             MtubMTV043   TGNGYLGGLQFTQSTWAAHGGGEFAPSAQLASREQQIAVGERVLATQGRG  109
             MtubZ94752   TGNGYYGGVQFDQGTWEANGGLRYAPRADLATREEQIAVAEVTRLRQGWG  350
             MlutZ96935   TGNGFYGGVQFTLSSWQAVGGEG---YPHQASKAEQIKRAEILQDLQGWG  106
             MlepL01095   TGNGFYGGLQFKPTIWARYGGVG---NPAGASREQQITVANRVLADQGLD  109
             MtubU38939   TGNGKYGGLQFKPATWAAFGGVG---NPAAASREQQIAVANRVLAEQGLD  135
             MtubZ81368   TGNGLYGGLQISQATWDSNGGVG---SPAAASPQQQIEVADNIMKTQGPG  116
             MtubMTV008   TGNGYYGGLQFTAGTWRANGGSG---SAANASREEQIRVAENVLRSQGIR  179
                          ****.******   .* . **         *.***** *** ..  **
```

FIG. 1A-2

```
Scoeli6C12S  AW------------------------------------------------  78
Mlepl04666   AWPACGHGLSGPSLQEVLPAG--MGAPw----INGAPAPLAPPPPAEPAP  152
MtubMTV043   AWPVCGRGLSNATPREVLPASaaMDAPldaaaVNGEPAPLA-PPPADPAP  158
MtubZ94752   AWPVCAaragar--------------------------------------  362
MlutZ96935   AWPLCSQKLgltqadadagdvdateaapvavertatvqrqsaadeaaaeq  156
MlepL01095   AWPKCGAASDLPITLWSHPAQGVKQIINDIIqmgdttlaaialngl----  155
MtubU38939   AWPTCGAASGLPIALWSKPAQGIKQIINEIIwagiqasipr---------  176
MtubZ81368   AWPKCSscsqgdaplgslthiltflaaetggcsgsrdd------------  154
MtubMTV008   AWPVCGrrg-----------------------------------------  188
             *** *.

Mlepl04666   pqppadnf-----------------------PPTPGDVPSPLarp-----  174
MtubMTV043   pvelaandlpaplgeplpaapadpappadlaPPAPADVAPPVelavndlp  208
MlutZ96935   aaaaeqavvaeaetivvksgdslwtlaneyeveggwtalyeankgavsda  206

MtubMTV043   aplgeplpaapadpappadlappapadlappapadlappapadlappvel  258
MlutZ96935   aviyvgqelvlpqa------------------------------------  220

MtubMTV043   avndlpaplgeplpaapaelappadlapasadlappapadlappapaela  308

MtubMTV043   ppapadlappaavneqtapgdqpatapggpvglatdlelpepdpqpadap  358

MtubMTV043   ppgdvteapaetpqvsniaytkklwqairaqdvcgndaldslaqpyvig-  407
```

| FIG. 1B-1 |
| --- |
| FIG. 1B-2 |

```
SEQ ID NO: 9  A YabEBsubt    mgeregrvdslldtlynlseekeaffitqkmkklfsvklsKSKVILVAACLLLAGSGTAYAAHELTKQSVSVSINGKKKHIR  82
SEQ ID NO: 1  A Mtubz94752   ----------------------------------------MLRLVVGALLLVLAFAGG-YAVAACKTVTLTVDGTAMR--VT  39

SEQ ID NO: 10 A YocHBsubt    -----------------------------------------------------------------------mkktimsfvav  11
              A YabEBsubt    THANTVGDLLETLDIKTRDEDKITPAKQTKITADMDVVYEAAKPVKLTING-EEKTLWSTAKTVGALLDEQDVDVKEQDQID 163
              A Mtubz94752   TMKSRVIDIVEENGFSVDDRDDLYPAAGVQVHDADTIVLRRSRPLQISLDGHDAKQVWTTASTVDEALAQLAMTDTAPAAAS 121
SEQ ID NO: 11 A Caceto506    ---------------------KR??AVILMVAVIFTIISSMKKNITVNIDG-KTSKIITYKSNEGSILSKNNILVGPKDKIQ  58
                                                      #    .     ..    . . . ..#       .     .  #    .
```

FIG. 1B-1

```
A yocHBsubt    aalsttafgahasakeitvqkgdtlwgisqkngvnlkdlkewnkltsdkiiagekltisseettttgqytikagdtlskiaq  93
A YabEBsubt    PAIDTDISKDMKINIEPAFQVTVNDAGKQKKIWTTSTTVADFLKQQKMNIKDEDKIKPALDAKLTKGKAD-ITITRIEKVTD  244
A MtubZ94752   RASRVPLSG-MALPVVSAKTVQLNDGGLVRTVHLPAPNVAGLLSAAGVPLLQSDHVVPAATAPIVEGMQIQVTRNRIKKVTE  202
A Caceto506    PALDTNLKNGDKIYIKKAISVEVAVDGKVRRVKSSEETVSKMLKAEKIPLSKVDKVNISRNAAIKKNM--KISITRVNSQIT  138
                #    .     .. # # .  #  . .        #  .#    . .   # .    # .        .. #.

A yocHBsubt    kfgttvnnlkvwnnlssdmiyaqstlsvkgqataantatenaqtnapqaapkqeavqkeqpkqeavqqqpkqetkaeaetsv  175
A YabEBsubt    VVEEKIAFDVKKQEDASLEKGKEKVVQKGKEGKLKKHFEVVKENGKEVSRELVKEETAEQSKDKVIAVGTKQSSPKFETVSA  326
A MtubZ94752   RLP--LPPNARRVEDPEMNMSREVVEDPGVPGTQDVTFAVAEVNGVETGRLPVANVVVTPAHEAVVRVGTKPGTEVPPVIDG  282
A Caceto506    KENQQVDFPTEVISDDSMGNDEKQVIQQGQAGEKEVFTKIVYEDGKAVSKEIVGEVIKKEPTKQVFKVGTlgvlkpdrggrv  220
                   .       #          # . #  #        .   .#    .  #            #..###

                B MtubZ94752   Siwdaiagceaggnwaintgnqyyggvqfdqgtweangglryapradlatreeqiavaevtrlrqgwgawpvcaaragar--  362
                B yocHBsubt    NTEEKAVQSNTNNQEASKELTVTATAYTANDGGISGVTATGIDLNKNPNA-KVIAVDPNVIPLGSKVYVEGYGEATTAADTG  256
                B YabEBsubt    SGDSKTVVSRSNE-STGKVMTVSSTAYTASCSGCSGHTATGVNLKNNPNA-KVIAVDPNVIPLGSKVHVEGYGYAIIAADTG  406
                B Caceto506    --------------LYKKSLQVLATAYTDDFSF--GITASGTKVKRDSDGYSSIAVDPTVIPLGTKLYVPGYGYGVVAEDTG  286
SEQ ID NO: 12   B Cperfring    ----------------------AEAYTA----------SGMHVLRDPNGYSTIAVDPSVIPLGTKLYVEGYGYAIIAADTG  49
                                                 * . *  *****     * **.*  . .  ..  ***** *****.*.********..*****

B YocHBsubt    GAIKGNKIDVFVPEKSSAYRWGNKTVKIKILN  288
B YabEBsubt    SAIKGNKIDVFFPSKSDASNWGVKTVSVKVLN  438
B Caceto506    GAIKGNRLDLFFTSERECYDNGAKNVTVYILK  318
B Cperfring    GAIKGNRVDLFFNTEAEASNWGVRNLDVYILN  81
               ******..*.** *  .* .** . . . .**
```

FIG. 1B-2

```
                RPF       TIVVKSGDSLWTLANE-YEVEGGWTALYEANKGAVS---------DAAVIYVGQELVLPQA
SEQ ID NO: 13   g149657   TIKVKSGDSLWKLSRQ-YDTT--ISALKSENKL------------KSTVLYVGQSLKVPES
SEQ ID NO: 14   g2226145  TIKVKSGDSLWKLAQT-YNTS--VAALTSANIIL------------STTVLSIGQTLTIP--
SEQ ID NO: 15   g2226145  TYTVKSGDSLWVIAQK-FNVT--AQQIREKNNL------------KTDVLQVGQKLVI---
SEQ ID NO: 16   g2226145  KYTVKSGDSLWKIANN-INLT--VQQIRNINNL------------KSDVLYVGQVLKL---
SEQ ID NO: 17   g266725   TYTVKSGDTIWALSSK-YGTS--VQNIMSWNNL------------SSSSIYVGQVLAVKQ-
SEQ ID NO: 18   g80581    THAVKSGDTIWALSVK-YGVS--VQDIMSWNNL------------SSSSIYVGQKLAIKQ-
SEQ ID NO: 19   g2707292  SVKVKSGDTLWALSVK-YKTS--IAQLKSWNHL------------SSDTIYIGQNLIVSQS
SEQ ID NO: 20   g755216   TYTVKSGDTLWGISQR-YGIS--VAQIQSANNL------------KSTIIYIGQKLLL---
SEQ ID NO: 21   g1722873  TYTVKKGDTLWDIAGRFYGNSTQWRKIWNANKTAMIKRSKRNIRQPGHWIFPGQKLKIPQ-
SEQ ID NO: 22   g1176755  TYTVKKGDTLWDLAGKFYGDSTKWRKIWKVNKKAMIKRSKRNIRQPGHWIFPGQKLKIPQ-
SEQ ID NO: 23
                          .  **.** .*          .     .   *.            .    ** *
```

| FIG. 1D-1 |
| --- |
| FIG. 1D-2 |

```
SEQ ID NO: 4 1 msgrhrkpttsnvsvakiaftgavlgggiamaaqataatdgewdqvarcesggnwsintgngylgg
               lqftqstwaahgggefapsaqlasreqqiavgervlatqgrgawpvcgrglsnatprevlpasaamd
               apldaaavngepaplapppadp 156

          157 appvelaandlpaplgeplpaapadpappadlappapadv 196
          197 appvelavndlpaplgeplpaapadpappadlappapadlappapadlappapadl 252
          253 appvelavndlpaplgeplpaapaelappadlap-asadlappapadlappapaelappapadlappa
          320 -------avne 323

          324 qtapgdqpatapggpvglatdlelpepdpqpadapppgdvteapaetpqvsniaytkklwqaira
          389 qdvcgndaldslaqpyvig* 407
```

| Motif | sequence | | | |
| --- | --- | --- | --- | --- |
| A | 157 | appvelaandl | 167 | SEQ ID NO: 25 |
| B' | 168 | paplgeplpaapad | 181 | SEQ ID NO: 28 |
| C | 182 | pappadl | 188 | SEQ ID NO: 29 |
| D | 189 | appapadv | 196 | SEQ ID NO: 31 |

FIG. 1D-1

```
A        197 appvelavndl      207 SEQ ID NO: 26
B'       208 paplgeplpaapad   221 SEQ ID NO: 28
C        222 pappadl          228 SEQ ID NO: 29
D        229 appapadl         236 SEQ ID NO: 30
D        237 appapadl         244 SEQ ID NO: 30
D        245 appapadl         252 SEQ ID NO: 30

A        253 appvelavndl      263 SEQ ID NO: 26
B        264 paplgeplpaapael  278 SEQ ID NO: 27
'C       279 appadl           284 SEQ ID NO: 55
D*       285 apasadl          291 SEQ ID NO: 56
D        292 appapadl         299 SEQ ID NO: 30
D        300 appapael         307 SEQ ID NO: 57
D        308 appapadl         315 SEQ ID NO: 30
D'       316 appa             319 SEQ ID NO: 58

'A'      320 avne             323 SEQ ID NO: 59
```

A = appvela[av]ndl

B = paplgeplpaapa[de]l

C = pappadl

D = appapa[de][lv]

FIG. 1D-2

```
SEQ ID NO:34  Lmonocytog..  mnmkkatiaatagiavtafaaptiasastvvveagdtlwgiaqskgttvdaikkannlttdkivpgqkiqvn  72
SEQ ID NO:36  MlutFactor    mtlfttsatrsrratasivagmtlagaaavgfsapaqaat----------vdtwdrlaecesngtwdintgn  62

              Lmonocytog..  nevaaaektekspvsatwlnvrtgagvdnsiitsikggtkvtvettesngwhkityndgktgfvngkyltdka 144
              MlutFactor    gfyggvgftlsswgavggegyphq---askaeqikraeilqdlqgwgawplcsqklgltqadadag------ 125

              Lmonocytog..  vstpvaptqevkkETTTQQAAPVAETKTEVKQTTQATTPAPKVAETKETPVIDQNATTHAVKSGDTIVADSV 216
              MlutFactor    -------------DVDATEAAPVAVERTATVQRQSAADEAAAEQAAAAEQAVVAEAETIVVKSGDSLVTDAN 184

              Lmonocytog..  KYGVsvqdimswnnl-----SSSSIYVGQKDAIKQTantatpkaevkteapaaekqaapvvkentntntatt 283
              MlutFactor    EYEVeggwtalyeankgavsDAAVIYVGQEDVLPQA------------------------------------ 220

              Lmonocytog..  ekketatqqqtapkapteaakpapapstntnanktntntntnntntpskntntnsntntntnsntnanqgss 355
              MlutFactor    ------------------------------------------------------------------------ 220

              Lmonocytog..  nnnsnssasaiiaeaqkhlgkayswggngpttfdcsgytkyvfakagislprtsgaqyasttrisesqakpg 427
              MlutFactor    ------------------------------------------------------------------------ 220

              Lmonocytog..  dlvffdygsgishvgiyvgngqminaqdngvkydnihgsgwgkylvgfgrv                     478
              MlutFactor    ---------------------------------------------------                     220
```

| FIG. 2A-1 |
|---|
| FIG. 2A-2 |

```
SEQ ID NO:35   1 accaaggagaaggacgaccccggtgtgcctcggccgccgatcagcgaggactcgccatgg 60
              61 acaccatgactctcttcaccacttccgccacccgctcccgccgtgccaccgcctcgatcg 120
                      M  T  L  F  T  T  S  A  T  R  S  R  R  A  T  A  S  I  V
                                                         SEQ ID NO: 37  g
             121 tcgcgggcatgaccctcgccggcgccgccgccgtgggcttctccgccccggcccaggccg 180
                   A  G  M  T  L  A  G  A  A  A  V  G  F  S  A  P  A  Q  A  A
                                                         SEQ ID NO: 38  A
                                    oligo A1>>>
                 csacsgtsgacacstgggaccgsctsgcsgag
             181 ccaccgtggacacctgggaccgcctcgccgagtgcgagtccaacggcacctgggacatca 240
                   T  V  D  T  W  D  R  L  A  E  C  E  S  N  G  T  W  D  I  N
                   T  V  D  T  W  D  R  L  A  E  E  x  S  N  G  T  x  D
                      <<< oligo G2     SEQ ID NO: 40   oligo G1>>>
SEQ ID NO: 39         gttgccgaagatgccgcc        agttcaccctgtcctcctg
             241 acaccggcaacggcttctacggcggcgtgcagttcaccctgtcctcctggcaggccgtcg 300
                   T  G  N  G  F  Y  G  G  V  Q  F  T  L  S  S  W  Q  A  V  G
                                                         SEQ ID NO: 42  G
```

FIG. 2A-1

```
SEQ ID NO: 41        <<< oligo A2
                     ccictycciatrggigtrgtycg
                 301 gcggcgaaggctacccgcaccaggcctcgaaggccgagcagatcaagcgcgccgagatcc 360
                      G  E  G  Y  P  H  Q  A  S  K  A  E  Q  I  K  R  A  E  I  L
                      G  E  G  Y  P  H  Q  A  S  K

                 361 tccaggacctgcagggctggggcgcgtggccgctgtgctcgcagaagctgggcctgaccc 420
                      Q  D  L  Q  G  W  G  A  W  P  L  C  S  Q  K  L  G  L  T  Q

                 421 aggctgacgcggacgccggtgacgtggacgccaccgaggccgccccggtcgccgtggagc 480
                      A  D  A  D  A  G  D  V  D  A  T  E  A  A  P  V  A  V  E  R

                 481 gcacggccaccgtgcagcgccagtccgccgcggacgaggctgccgccgagcaggccgctg 540
                      T  A  T  V  Q  R  Q  S  A  A  D  E  A  A  A  E  Q  A  A  A

                 541 ccgcggagcaggccgtcgtcgccgaggccgagaccatcgtcgtcaagtccggtgactccc 600
                      A  E  Q  A  V  V  A  E  A  E  T  I  V  V  K  S  G  D  S  L

                 601 tctggacgctcgccaacgagtacgaggtggagggtggctggaccgccctctacgaggcca 660
                      W  T  L  A  N  E  Y  E  V  E  G  G  W  T  A  L  Y  E  A  N

                 661 acaagggcgccgtctccgacgccgccgtgatctacgtcggccaggagctcgtcctgccgc 720
                      K  G  A  V  S  D  A  A  V  I  Y  V  G  Q  E  L  V  L  P  Q

                 721 aggcctgagacgcctgaccggcccccggaccggtacc 758
                      A  *

SEQ ID NO: 43 1   ATVDTWDRLA ECESNGTWDI NTGNGFYGGV QFTLSSWQAV GGEGYPHQAS KAEQIKRAEI     60
              61  LQDLQGWGAW PLCSQKLGLT QADADAGDVD ATEAAPVAVE RTATVQRQSA ADEAAAEQAA    120
              121 AAEQAVVAEA ETIVVKSGDS LWTLANEYEV EGGWTALYEA NKGAVSDAAV IYVGQELVLP QA 182
```

FIG. 2A-2

```
SEQ ID NO:44  ggatccgcaccgccgcggtaaccctggtcgccgcgaccgcactcggggcgaccggcgaag   60
SEQ ID NO:45   I  R  T  A  A  V  T  L  V  A  A  T  A  L  G  A  T  G  E  A

              cggtggccgcgccctcggcgcccctgcgcaccgactgggacgccatcgccgcgtgcgagt  120
               V  A  A  P  S  A  P  L  R  T  D  W  D  A  I  A  A  C  E  S

              ccagcggcaactggcaggcgaacaccggcaacggctactacggcggcctgcagttcgcac  180
               S  G  N  W  Q  A  N  T  G  N  G  Y  Y  G  G  L  Q  F  A  R

              ggtccagctggatcgccgccggcggcctcaagtacgccccgcgcgcggacctcgccaccc  240
               S  S  W  I  A  A  G  G  L  K  Y  A  P  R  A  D  L  A  T  R

              gcggcgagcagatcgccgtggcggaacgcctcgcccgtctgcaggggatgtccgcctgg   299
               G  E  Q  I  A  V  A  E  R  L  A  R  L  Q  G  M  S  A  W
```

FIG. 2B

FIG. 3C
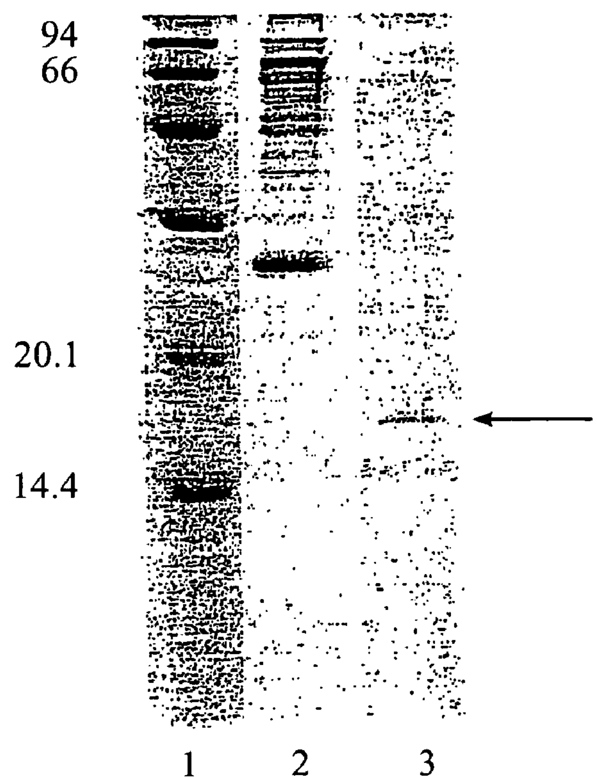
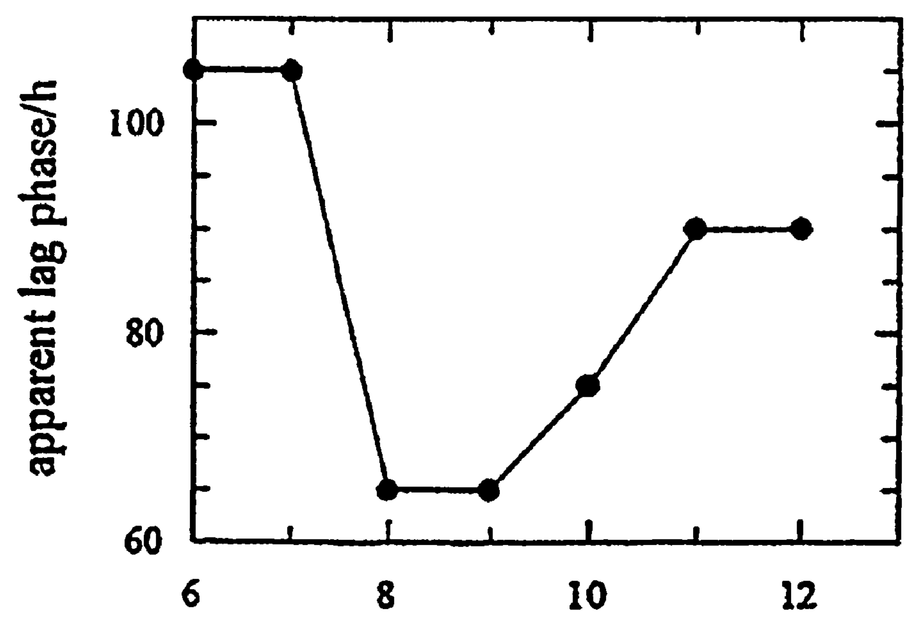
FIG. 3D

SEQUENCE LISTING

<160> NUMBER OF SEQ ID NOS: 65

<210> SEQ ID NO 1
<211> LENGTH: 362
<212> TYPE: PRT
<213> ORGANISM: Mycobacterium tuberculosis

<400> SEQUENCE: 1

Met Leu Arg Leu Val Val Gly Ala Leu Leu Leu Val Leu Ala Phe Ala
1 5 10 15

Gly Gly Tyr Ala Val Ala Ala Cys Lys Thr Val Thr Leu Thr Val Asp
20 25 30

Gly Thr Ala Met Arg Val Thr Thr Met Lys Ser Arg Val Ile Asp Ile
35 40 45

Val Glu Glu Asn Gly Phe Ser Val Asp Asp Arg Asp Asp Leu Tyr Pro
50 55 60

Ala Ala Gly Val Gln Val His Asp Ala Asp Thr Ile Val Leu Arg Arg
65 70 75 80

Ser Arg Pro Leu Gln Ile Ser Leu Asp Gly His Asp Ala Lys Gln Val
85 90 95

Trp Thr Thr Ala Ser Thr Val Asp Glu Ala Leu Ala Gln Leu Ala Met
100 105 110

Thr Asp Thr Ala Pro Ala Ala Ala Ser Arg Ala Ser Arg Val Pro Leu
115 120 125

Ser Gly Met Ala Leu Pro Val Val Ser Ala Lys Thr Val Gln Leu Asn
130 135 140

Asp Gly Gly Leu Val Arg Thr Val His Leu Pro Ala Pro Asn Val Ala
145 150 155 160

Gly Leu Leu Ser Ala Ala Gly Val Pro Leu Leu Gln Ser Asp His Val
165 170 175

Val Pro Ala Ala Thr Ala Pro Ile Val Glu Gly Met Gln Ile Gln Val
180 185 190

Thr Arg Asn Arg Ile Lys Lys Val Thr Glu Arg Leu Pro Leu Pro Pro
195 200 205

Asn Ala Arg Arg Val Glu Asp Pro Glu Met Asn Met Ser Arg Glu Val
210 215 220

```
Val Glu Asp Pro Gly Val Pro Gly Thr Gln Asp Val Thr Phe Ala Val
225                 230                 235                 240

Ala Glu Val Asn Gly Val Glu Thr Gly Arg Leu Pro Val Ala Asn Val
                245                 250                 255

Val Val Thr Pro Ala His Glu Ala Val Val Arg Val Gly Thr Lys Pro
            260                 265                 270

Gly Thr Glu Val Pro Pro Val Ile Asp Gly Ser Ile Trp Asp Ala Ile
        275                 280                 285

Ala Gly Cys Glu Ala Gly Gly Asn Trp Ala Ile Asn Thr Gly Asn Gly
    290                 295                 300

Tyr Tyr Gly Gly Val Gln Phe Asp Gln Gly Thr Trp Glu Ala Asn Gly
305                 310                 315                 320

Gly Leu Arg Tyr Ala Pro Arg Ala Asp Leu Ala Thr Arg Glu Glu Gln
                325                 330                 335

Ile Ala Val Ala Glu Val Thr Arg Leu Arg Gln Gly Trp Gly Ala Trp
            340                 345                 350

Pro Val Cys Ala Ala Arg Ala Gly Ala Arg
        355                 360


<210> SEQ ID NO 2
<211> LENGTH: 188
<212> TYPE: PRT
<213> ORGANISM: Mycobacterium tuberculosis

<400> SEQUENCE: 2

Met Pro Val Gly Trp Leu Trp Arg Ala Arg Thr Ala Lys Gly Thr Thr
1               5                   10                  15

Leu Lys Asn Ala Arg Thr Thr Leu Ile Ala Ala Ala Ile Ala Gly Thr
            20                  25                  30

Leu Val Thr Thr Ser Pro Ala Gly Ile Ala Asn Ala Asp Asp Ala Gly
        35                  40                  45

Leu Asp Pro Asn Ala Ala Ala Gly Pro Asp Ala Val Gly Phe Asp Pro
    50                  55                  60

Asn Leu Pro Pro Ala Pro Asp Ala Ala Pro Val Asp Thr Pro Pro Ala
65                  70                  75                  80

Pro Glu Asp Ala Gly Phe Asp Pro Asn Leu Pro Pro Pro Leu Ala Pro
                85                  90                  95

Asp Phe Leu Ser Pro Pro Ala Glu Glu Ala Pro Pro Val Pro Val Ala
            100                 105                 110

Tyr Ser Val Asn Trp Asp Ala Ile Ala Gln Cys Glu Ser Gly Gly Asn
        115                 120                 125

Trp Ser Ile Asn Thr Gly Asn Gly Tyr Tyr Gly Gly Leu Arg Phe Thr
    130                 135                 140

Ala Gly Thr Trp Arg Ala Asn Gly Gly Ser Gly Ser Ala Ala Asn Ala
145                 150                 155                 160

Ser Arg Glu Glu Gln Ile Arg Val Ala Glu Asn Val Leu Arg Ser Gln
                165                 170                 175

Gly Ile Arg Ala Trp Pro Val Cys Gly Arg Arg Gly
            180                 185


<210> SEQ ID NO 3
<211> LENGTH: 174
<212> TYPE: PRT
<213> ORGANISM: Mycobacterium leprae

<400> SEQUENCE: 3

Met Ser Glu Ser Tyr Arg Lys Leu Thr Thr Ser Ser Ile Ile Val Ala
```

```
1               5                   10                  15

Lys Ile Thr Phe Thr Gly Ala Met Leu Asp Gly Ser Ile Ala Leu Ala
            20                  25                  30

Gly Gln Ala Ser Pro Ala Thr Asp Ser Glu Trp Asp Gln Val Ala Arg
        35                  40                  45

Cys Glu Ser Gly Gly Asn Trp Ser Ile Asn Thr Gly Asn Gly Tyr Leu
    50                  55                  60

Gly Gly Leu Gln Phe Ser Gln Gly Thr Trp Ala Ser His Gly Gly Gly
65                  70                  75                  80

Glu Tyr Ala Pro Ser Ala Gln Leu Ala Thr Arg Glu Gln Gln Ile Ala
                85                  90                  95

Val Ala Glu Arg Val Leu Ala Thr Gln Gly Ser Gly Ala Trp Pro Ala
            100                 105                 110

Cys Gly His Gly Leu Ser Gly Pro Ser Leu Gln Glu Val Leu Pro Ala
        115                 120                 125

Gly Met Gly Ala Pro Trp Ile Asn Gly Ala Pro Ala Pro Leu Ala Pro
    130                 135                 140

Pro Pro Pro Ala Glu Pro Ala Pro Pro Gln Pro Pro Ala Asp Asn Phe
145                 150                 155                 160

Pro Pro Thr Pro Gly Asp Val Pro Ser Pro Leu Ala Arg Pro
                165                 170


<210> SEQ ID NO 4
<211> LENGTH: 407
<212> TYPE: PRT
<213> ORGANISM: Mycobacterium tuberculosis

<400> SEQUENCE: 4

Met Ser Gly Arg His Arg Lys Pro Thr Thr Ser Asn Val Ser Val Ala
1               5                   10                  15

Lys Ile Ala Phe Thr Gly Ala Val Leu Gly Gly Gly Gly Ile Ala Met
            20                  25                  30

Ala Ala Gln Ala Thr Ala Ala Thr Asp Gly Glu Trp Asp Gln Val Ala
        35                  40                  45

Arg Cys Glu Ser Gly Gly Asn Trp Ser Ile Asn Thr Gly Asn Gly Tyr
    50                  55                  60

Leu Gly Gly Leu Gln Phe Thr Gln Ser Thr Trp Ala Ala His Gly Gly
65                  70                  75                  80

Gly Glu Phe Ala Pro Ser Ala Gln Leu Ala Ser Arg Glu Gln Gln Ile
                85                  90                  95

Ala Val Gly Glu Arg Val Leu Ala Thr Gln Gly Arg Gly Ala Trp Pro
            100                 105                 110

Val Cys Gly Arg Gly Leu Ser Asn Ala Thr Pro Arg Glu Val Leu Pro
        115                 120                 125

Ala Ser Ala Ala Met Asp Ala Pro Leu Asp Ala Ala Ala Val Asn Gly
    130                 135                 140

Glu Pro Ala Pro Leu Ala Pro Pro Pro Ala Asp Pro Ala Pro Pro Val
145                 150                 155                 160

Glu Leu Ala Ala Asn Asp Leu Pro Ala Pro Leu Gly Glu Pro Leu Pro
                165                 170                 175

Ala Ala Pro Ala Asp Pro Ala Pro Pro Ala Asp Leu Ala Pro Pro Ala
            180                 185                 190

Pro Ala Asp Val Ala Pro Pro Val Glu Leu Ala Val Asn Asp Leu Pro
        195                 200                 205

Ala Pro Leu Gly Glu Pro Leu Pro Ala Ala Pro Ala Asp Pro Ala Pro
```

```
    210                 215                 220

Pro Ala Asp Leu Ala Pro Pro Ala Pro Ala Asp Leu Ala Pro Pro Ala
225                 230                 235                 240

Pro Ala Asp Leu Ala Pro Pro Ala Pro Ala Asp Leu Ala Pro Pro Val
                245                 250                 255

Glu Leu Ala Val Asn Asp Leu Pro Ala Pro Leu Gly Glu Pro Leu Pro
            260                 265                 270

Ala Ala Pro Ala Glu Leu Ala Pro Pro Ala Asp Leu Ala Pro Ala Ser
        275                 280                 285

Ala Asp Leu Ala Pro Pro Ala Pro Ala Asp Leu Ala Pro Pro Ala Pro
    290                 295                 300

Ala Glu Leu Ala Pro Pro Ala Pro Ala Asp Leu Ala Pro Pro Ala Ala
305                 310                 315                 320

Val Asn Glu Gln Thr Ala Pro Gly Asp Gln Pro Ala Thr Ala Pro Gly
                325                 330                 335

Gly Pro Val Gly Leu Ala Thr Asp Leu Glu Leu Pro Glu Pro Asp Pro
            340                 345                 350

Gln Pro Ala Asp Ala Pro Pro Pro Gly Asp Val Thr Glu Ala Pro Ala
        355                 360                 365

Glu Thr Pro Gln Val Ser Asn Ile Ala Tyr Thr Lys Lys Leu Trp Gln
    370                 375                 380

Ala Ile Arg Ala Gln Asp Val Cys Gly Asn Asp Ala Leu Asp Ser Leu
385                 390                 395                 400

Ala Gln Pro Tyr Val Ile Gly
                405


<210> SEQ ID NO 5
<211> LENGTH: 155
<212> TYPE: PRT
<213> ORGANISM: Mycobacterium leprae

<400> SEQUENCE: 5

Met Pro Gly Glu Met Leu Asp Val Arg Lys Leu Cys Lys Leu Phe Val
1               5                   10                  15

Lys Ser Ala Val Val Ser Gly Ile Val Thr Ala Ser Met Ala Leu Ser
            20                  25                  30

Thr Ser Thr Gly Met Ala Asn Ala Val Pro Arg Glu Pro Asn Trp Asp
        35                  40                  45

Ala Val Ala Gln Cys Glu Ser Gly Arg Asn Trp Arg Ala Asn Thr Gly
    50                  55                  60

Asn Gly Phe Tyr Gly Gly Leu Gln Phe Lys Pro Thr Ile Trp Ala Arg
65                  70                  75                  80

Tyr Gly Gly Val Gly Asn Pro Ala Gly Ala Ser Arg Glu Gln Gln Ile
                85                  90                  95

Thr Val Ala Asn Arg Val Leu Ala Asp Gln Gly Leu Asp Ala Trp Pro
            100                 105                 110

Lys Cys Gly Ala Ala Ser Asp Leu Pro Ile Thr Leu Trp Ser His Pro
        115                 120                 125

Ala Gln Gly Val Lys Gln Ile Ile Asn Asp Ile Ile Gln Met Gly Asp
    130                 135                 140

Thr Thr Leu Ala Ala Ile Ala Leu Asn Gly Leu
145                 150                 155


<210> SEQ ID NO 6
<211> LENGTH: 176
<212> TYPE: PRT
```

```
<213> ORGANISM: Mycobacterium tuberculosis

<400> SEQUENCE: 6

Met His Pro Leu Pro Ala Asp His Gly Arg Ser Arg Cys Asn Arg His
1               5                   10                  15

Pro Ile Ser Pro Leu Ser Leu Ile Gly Asn Ile Ser Ala Thr Ser Gly
            20                  25                  30

Asp Met Ser Ser Met Thr Arg Ile Ala Lys Pro Leu Ile Lys Ser Ala
        35                  40                  45

Met Ala Ala Gly Leu Val Thr Ala Ser Met Ser Leu Ser Thr Ala Val
    50                  55                  60

Ala His Ala Gly Pro Ser Pro Asn Trp Asp Ala Val Ala Gln Cys Glu
65                  70                  75                  80

Ser Gly Gly Asn Trp Ala Ala Asn Thr Gly Asn Gly Lys Tyr Gly Gly
                85                  90                  95

Leu Gln Phe Lys Pro Ala Thr Trp Ala Ala Phe Gly Gly Val Gly Asn
            100                 105                 110

Pro Ala Ala Ala Ser Arg Glu Gln Gln Ile Ala Val Ala Asn Arg Val
        115                 120                 125

Leu Ala Glu Gln Gly Leu Asp Ala Trp Pro Thr Cys Gly Ala Ala Ser
    130                 135                 140

Gly Leu Pro Ile Ala Leu Trp Ser Lys Pro Ala Gln Gly Ile Lys Gln
145                 150                 155                 160

Ile Ile Asn Glu Ile Ile Trp Ala Gly Ile Gln Ala Ser Ile Pro Arg
                165                 170                 175


<210> SEQ ID NO 7
<211> LENGTH: 154
<212> TYPE: PRT
<213> ORGANISM: Mycobacterium tuberculosis

<400> SEQUENCE: 7

Met Thr Pro Gly Leu Leu Thr Thr Ala Gly Ala Gly Arg Pro Arg Asp
1               5                   10                  15

Arg Cys Ala Arg Ile Val Cys Thr Val Phe Ile Glu Thr Ala Val Val
            20                  25                  30

Ala Thr Met Phe Val Ala Leu Leu Gly Leu Ser Thr Ile Ser Ser Lys
        35                  40                  45

Ala Asp Asp Ile Asp Trp Asp Ala Ile Ala Gln Cys Glu Ser Gly Gly
    50                  55                  60

Asn Trp Ala Ala Asn Thr Gly Asn Gly Leu Tyr Gly Gly Leu Gln Ile
65                  70                  75                  80

Ser Gln Ala Thr Trp Asp Ser Asn Gly Gly Val Gly Ser Pro Ala Ala
                85                  90                  95

Ala Ser Pro Gln Gln Gln Ile Glu Val Ala Asp Asn Ile Met Lys Thr
            100                 105                 110

Gln Gly Pro Gly Ala Trp Pro Lys Cys Ser Ser Cys Ser Gln Gly Asp
        115                 120                 125

Ala Pro Leu Gly Ser Leu Thr His Ile Leu Thr Phe Leu Ala Ala Glu
    130                 135                 140

Thr Gly Gly Cys Ser Gly Ser Arg Asp Asp
145                 150


<210> SEQ ID NO 8
<211> LENGTH: 99
<212> TYPE: PRT
<213> ORGANISM: Streptomyces coelicolor
```

<400> SEQUENCE: 8

```
Ile Arg Thr Ala Ala Val Thr Leu Val Ala Ala Thr Ala Leu Gly Ala
1               5                   10                  15

Thr Gly Glu Ala Val Ala Ala Pro Ser Ala Pro Leu Arg Thr Asp Trp
            20                  25                  30

Asp Ala Ile Ala Ala Cys Glu Ser Ser Gly Asn Trp Gln Ala Asn Thr
        35                  40                  45

Gly Asn Gly Tyr Tyr Gly Gly Leu Gln Phe Ala Arg Ser Ser Trp Ile
    50                  55                  60

Ala Ala Gly Gly Leu Lys Tyr Ala Pro Arg Ala Asp Leu Ala Thr Arg
65                  70                  75                  80

Gly Glu Gln Ile Ala Val Ala Glu Arg Leu Ala Arg Leu Gln Gly Met
                85                  90                  95

Ser Ala Trp
```

<210> SEQ ID NO 9
<211> LENGTH: 438
<212> TYPE: PRT
<213> ORGANISM: Bacillus subtilis

<400> SEQUENCE: 9

```
Met Gly Glu Arg Glu Gly Arg Val Asp Ser Leu Leu Asp Thr Leu Tyr
1               5                   10                  15

Asn Leu Ser Glu Glu Lys Glu Ala Phe Phe Ile Thr Gln Lys Met Lys
            20                  25                  30

Lys Leu Phe Ser Val Lys Leu Ser Lys Ser Lys Val Ile Leu Val Ala
        35                  40                  45

Ala Cys Leu Leu Leu Ala Gly Ser Gly Thr Ala Tyr Ala Ala His Glu
    50                  55                  60

Leu Thr Lys Gln Ser Val Ser Val Ser Ile Asn Gly Lys Lys Lys His
65                  70                  75                  80

Ile Arg Thr His Ala Asn Thr Val Gly Asp Leu Leu Glu Thr Leu Asp
                85                  90                  95

Ile Lys Thr Arg Asp Glu Asp Lys Ile Thr Pro Ala Lys Gln Thr Lys
            100                 105                 110

Ile Thr Ala Asp Met Asp Val Val Tyr Glu Ala Ala Lys Pro Val Lys
        115                 120                 125

Leu Thr Ile Asn Gly Glu Glu Lys Thr Leu Trp Ser Thr Ala Lys Thr
    130                 135                 140

Val Gly Ala Leu Leu Asp Glu Gln Asp Val Asp Val Lys Glu Gln Asp
145                 150                 155                 160

Gln Ile Asp Pro Ala Ile Asp Thr Asp Ile Ser Lys Asp Met Lys Ile
                165                 170                 175

Asn Ile Glu Pro Ala Phe Gln Val Thr Val Asn Asp Ala Gly Lys Gln
            180                 185                 190

Lys Lys Ile Trp Thr Thr Ser Thr Thr Val Ala Asp Phe Leu Lys Gln
        195                 200                 205

Gln Lys Met Asn Ile Lys Asp Glu Asp Lys Ile Lys Pro Ala Leu Asp
    210                 215                 220

Ala Lys Leu Thr Lys Gly Lys Ala Asp Ile Thr Ile Thr Arg Ile Glu
225                 230                 235                 240

Lys Val Thr Asp Val Val Glu Glu Lys Ile Ala Phe Asp Val Lys Lys
                245                 250                 255

Gln Glu Asp Ala Ser Leu Glu Lys Gly Lys Glu Lys Val Val Gln Lys
```

```
            260                 265                 270

Gly Lys Glu Gly Lys Leu Lys Lys His Phe Glu Val Val Lys Glu Asn
        275                 280                 285

Gly Lys Glu Val Ser Arg Glu Leu Val Lys Glu Glu Thr Ala Glu Gln
    290                 295                 300

Ser Lys Asp Lys Val Ile Ala Val Gly Thr Lys Gln Ser Ser Pro Lys
305                 310                 315                 320

Phe Glu Thr Val Ser Ala Ser Gly Asp Ser Lys Thr Val Val Ser Arg
                325                 330                 335

Ser Asn Glu Ser Thr Gly Lys Val Met Thr Val Ser Ser Thr Ala Tyr
            340                 345                 350

Thr Ala Ser Cys Ser Gly Cys Ser Gly His Thr Ala Thr Gly Val Asn
        355                 360                 365

Leu Lys Asn Asn Pro Asn Ala Lys Val Ile Ala Val Asp Pro Asn Val
    370                 375                 380

Ile Pro Leu Gly Ser Lys Val His Val Glu Gly Tyr Gly Tyr Ala Ile
385                 390                 395                 400

Ile Ala Ala Asp Thr Gly Ser Ala Ile Lys Gly Asn Lys Ile Asp Val
                405                 410                 415

Phe Phe Pro Ser Lys Ser Asp Ala Ser Asn Trp Gly Val Lys Thr Val
            420                 425                 430

Ser Val Lys Val Leu Asn
        435


<210> SEQ ID NO 10
<211> LENGTH: 288
<212> TYPE: PRT
<213> ORGANISM: Bacillus subtilis

<400> SEQUENCE: 10

Met Lys Lys Thr Ile Met Ser Phe Val Ala Val Ala Ala Leu Ser Thr
1               5                   10                  15

Thr Ala Phe Gly Ala His Ala Ser Ala Lys Glu Ile Thr Val Gln Lys
            20                  25                  30

Gly Asp Thr Leu Trp Gly Ile Ser Gln Lys Asn Gly Val Asn Leu Lys
        35                  40                  45

Asp Leu Lys Glu Trp Asn Lys Leu Thr Ser Asp Lys Ile Ile Ala Gly
    50                  55                  60

Glu Lys Leu Thr Ile Ser Ser Glu Glu Thr Thr Thr Thr Gly Gln Tyr
65                  70                  75                  80

Thr Ile Lys Ala Gly Asp Thr Leu Ser Lys Ile Ala Gln Lys Phe Gly
                85                  90                  95

Thr Thr Val Asn Asn Leu Lys Val Trp Asn Asn Leu Ser Ser Asp Met
            100                 105                 110

Ile Tyr Ala Gly Ser Thr Leu Ser Val Lys Gly Gln Ala Thr Ala Ala
        115                 120                 125

Asn Thr Ala Thr Glu Asn Ala Gln Thr Asn Ala Pro Gln Ala Ala Pro
    130                 135                 140

Lys Gln Glu Ala Val Gln Lys Glu Gln Pro Lys Gln Glu Ala Val Gln
145                 150                 155                 160

Gln Gln Pro Lys Gln Glu Thr Lys Ala Glu Ala Glu Thr Ser Val Asn
                165                 170                 175

Thr Glu Glu Lys Ala Val Gln Ser Asn Thr Asn Asn Gln Glu Ala Ser
            180                 185                 190

Lys Glu Leu Thr Val Thr Ala Thr Ala Tyr Thr Ala Asn Asp Gly Gly
```

```
        195                 200                 205

Ile Ser Gly Val Thr Ala Thr Gly Ile Asp Leu Asn Lys Asn Pro Asn
    210                 215                 220

Ala Lys Val Ile Ala Val Asp Pro Asn Val Ile Pro Leu Gly Ser Lys
225                 230                 235                 240

Val Tyr Val Glu Gly Tyr Gly Glu Ala Thr Thr Ala Ala Asp Thr Gly
                245                 250                 255

Gly Ala Ile Lys Gly Asn Lys Ile Asp Val Phe Val Pro Glu Lys Ser
            260                 265                 270

Ser Ala Tyr Arg Trp Gly Asn Lys Thr Val Lys Ile Lys Ile Leu Asn
        275                 280                 285


<210> SEQ ID NO 11
<211> LENGTH: 320
<212> TYPE: PRT
<213> ORGANISM: Clostridium acetobutylicum
<220> FEATURE:
<221> NAME/KEY: MOD_RES
<222> LOCATION: (3)..(4)
<223> OTHER INFORMATION: Variable amino acid

<400> SEQUENCE: 11

Lys Arg Xaa Xaa Ala Val Ile Leu Met Val Ala Val Ile Phe Thr Ile
1               5                   10                  15

Ile Ser Ser Met Lys Lys Asn Ile Thr Val Asn Ile Asp Gly Lys Thr
            20                  25                  30

Ser Lys Ile Ile Thr Tyr Lys Ser Asn Glu Gly Ser Ile Leu Ser Lys
        35                  40                  45

Asn Asn Ile Leu Val Gly Pro Lys Asp Lys Ile Gln Pro Ala Leu Asp
    50                  55                  60

Thr Asn Leu Lys Asn Gly Asp Lys Ile Tyr Ile Lys Lys Ala Ile Ser
65                  70                  75                  80

Val Glu Val Ala Val Asp Gly Lys Val Arg Arg Val Lys Ser Ser Glu
                85                  90                  95

Glu Thr Val Ser Lys Met Leu Lys Ala Glu Lys Ile Pro Leu Ser Lys
            100                 105                 110

Val Asp Lys Val Asn Ile Ser Arg Asn Ala Ala Ile Lys Lys Asn Met
        115                 120                 125

Lys Ile Ser Ile Thr Arg Val Asn Ser Gln Ile Thr Lys Glu Asn Gln
    130                 135                 140

Gln Val Asp Phe Pro Thr Glu Val Ile Ser Asp Asp Ser Met Gly Asn
145                 150                 155                 160

Asp Glu Lys Gln Val Ile Gln Gln Gly Gln Ala Gly Glu Lys Glu Val
                165                 170                 175

Phe Thr Lys Ile Val Tyr Glu Asp Gly Lys Ala Val Ser Lys Glu Ile
            180                 185                 190

Val Gly Glu Val Ile Lys Lys Glu Pro Thr Lys Gln Val Phe Lys Val
        195                 200                 205

Gly Thr Leu Gly Val Leu Lys Pro Asp Arg Gly Gly Arg Val Leu Tyr
    210                 215                 220

Lys Lys Ser Leu Gln Val Leu Ala Thr Ala Tyr Thr Asp Asp Phe Ser
225                 230                 235                 240

Phe Gly Ile Thr Ala Ser Gly Thr Lys Val Lys Arg Asp Ser Asp Gly
                245                 250                 255

Tyr Ser Ser Ile Ala Val Asp Pro Thr Val Ile Pro Leu Gly Thr Lys
            260                 265                 270
```

```
Leu Tyr Val Pro Gly Tyr Gly Tyr Gly Val Val Ala Glu Asp Thr Gly
        275                 280                 285

Gly Ala Ile Lys Gly Asn Arg Leu Asp Leu Phe Phe Thr Ser Glu Arg
    290                 295                 300

Glu Cys Tyr Asp Trp Gly Ala Lys Asn Val Thr Val Tyr Ile Leu Lys
305                 310                 315                 320


<210> SEQ ID NO 12
<211> LENGTH: 81
<212> TYPE: PRT
<213> ORGANISM: Clostridium perfringens

<400> SEQUENCE: 12

Ala Glu Ala Tyr Thr Ala Ser Gly Met His Val Leu Arg Asp Pro Asn
1               5                   10                  15

Gly Tyr Ser Thr Ile Ala Val Asp Pro Ser Val Ile Pro Leu Gly Thr
            20                  25                  30

Lys Leu Tyr Val Glu Gly Tyr Gly Tyr Ala Ile Ile Ala Ala Asp Thr
        35                  40                  45

Gly Gly Ala Ile Lys Gly Asn Arg Val Asp Leu Phe Phe Asn Thr Glu
    50                  55                  60

Ala Glu Ala Ser Asn Trp Gly Val Arg Asn Leu Asp Val Tyr Ile Leu
65                  70                  75                  80

Asn


<210> SEQ ID NO 13
<211> LENGTH: 51
<212> TYPE: PRT
<213> ORGANISM: Unknown
<220> FEATURE:
<223> OTHER INFORMATION: Description of Unknown Organism: RP-factor
      C-terminal domain peptide

<400> SEQUENCE: 13

Thr Ile Val Val Lys Ser Gly Asp Ser Leu Trp Thr Leu Ala Asn Glu
1               5                   10                  15

Tyr Glu Val Glu Gly Gly Trp Thr Ala Leu Tyr Glu Ala Asn Lys Gly
            20                  25                  30

Ala Val Ser Asp Ala Ala Val Ile Tyr Val Gly Gln Glu Leu Val Leu
        35                  40                  45

Pro Gln Ala
    50


<210> SEQ ID NO 14
<211> LENGTH: 46
<212> TYPE: PRT
<213> ORGANISM: Unknown
<220> FEATURE:
<223> OTHER INFORMATION: Description of Unknown Organism: Hypothetical
      wall-associated protein fragment

<400> SEQUENCE: 14

Thr Ile Lys Val Lys Ser Gly Asp Ser Leu Trp Lys Leu Ser Arg Gln
1               5                   10                  15

Tyr Asp Thr Thr Ile Ser Ala Leu Lys Ser Glu Asn Lys Leu Lys Ser
            20                  25                  30

Thr Val Leu Tyr Val Gly Gln Ser Leu Lys Val Pro Glu Ser
        35                  40                  45


<210> SEQ ID NO 15
<211> LENGTH: 44
```

```
<212> TYPE: PRT
<213> ORGANISM: Unknown
<220> FEATURE:
<223> OTHER INFORMATION: Description of Unknown Organism: Hypothetical
      wall-associated protein fragment

<400> SEQUENCE: 15

Thr Ile Lys Val Lys Ser Gly Asp Ser Leu Trp Lys Leu Ala Gln Thr
1               5                   10                  15

Tyr Asn Thr Ser Val Ala Ala Leu Thr Ser Ala Asn His Leu Ser Thr
            20                  25                  30

Thr Val Leu Ser Ile Gly Gln Thr Leu Thr Ile Pro
        35                  40


<210> SEQ ID NO 16
<211> LENGTH: 43
<212> TYPE: PRT
<213> ORGANISM: Unknown
<220> FEATURE:
<223> OTHER INFORMATION: Description of Unknown Organism: Hypothetical
      wall-associated protein fragment

<400> SEQUENCE: 16

Thr Tyr Thr Val Lys Ser Gly Asp Ser Leu Trp Val Ile Ala Gln Lys
1               5                   10                  15

Phe Asn Val Thr Ala Gln Gln Ile Arg Glu Lys Asn Asn Leu Lys Thr
            20                  25                  30

Asp Val Leu Gln Val Gly Gln Lys Leu Val Ile
        35                  40


<210> SEQ ID NO 17
<211> LENGTH: 43
<212> TYPE: PRT
<213> ORGANISM: Unknown
<220> FEATURE:
<223> OTHER INFORMATION: Description of Unknown Organism: Hypothetical
      wall-associated protein fragment

<400> SEQUENCE: 17

Lys Tyr Thr Val Lys Ser Gly Asp Ser Leu Trp Lys Ile Ala Asn Asn
1               5                   10                  15

Ile Asn Leu Thr Val Gln Gln Ile Arg Asn Ile Asn Asn Leu Lys Ser
            20                  25                  30

Asp Val Leu Tyr Val Gly Gln Val Leu Lys Leu
        35                  40


<210> SEQ ID NO 18
<211> LENGTH: 45
<212> TYPE: PRT
<213> ORGANISM: Unknown
<220> FEATURE:
<223> OTHER INFORMATION: Description of Unknown Organism: Hypothetical
      wall-associated protein fragment

<400> SEQUENCE: 18

Thr Tyr Thr Val Lys Ser Gly Asp Thr Ile Trp Ala Leu Ser Ser Lys
1               5                   10                  15

Tyr Gly Thr Ser Val Gln Asn Ile Met Ser Trp Asn Asn Leu Ser Ser
            20                  25                  30

Ser Ser Ile Tyr Val Gly Gln Val Leu Ala Val Lys Gln
        35                  40                  45


<210> SEQ ID NO 19
<211> LENGTH: 45
```

<212> TYPE: PRT
<213> ORGANISM: Unknown
<220> FEATURE:
<223> OTHER INFORMATION: Description of Unknown Organism: Hypothetical wall-associated protein fragment

<400> SEQUENCE: 19

```
Thr His Ala Val Lys Ser Gly Asp Thr Ile Trp Ala Leu Ser Val Lys
1               5                   10                  15

Tyr Gly Val Ser Val Gln Asp Ile Met Ser Trp Asn Asn Leu Ser Ser
            20                  25                  30

Ser Ser Ile Tyr Val Gly Gln Lys Leu Ala Ile Lys Gln
        35                  40                  45
```

<210> SEQ ID NO 20
<211> LENGTH: 46
<212> TYPE: PRT
<213> ORGANISM: Unknown
<220> FEATURE:
<223> OTHER INFORMATION: Description of Unknown Organism: Hypothetical wall-associated protein fragment

<400> SEQUENCE: 20

```
Ser Val Lys Val Lys Ser Gly Asp Thr Leu Trp Ala Leu Ser Val Lys
1               5                   10                  15

Tyr Lys Thr Ser Ile Ala Gln Leu Lys Ser Trp Asn His Leu Ser Ser
            20                  25                  30

Asp Thr Ile Tyr Ile Gly Gln Asn Leu Ile Val Ser Gln Ser
        35                  40                  45
```

<210> SEQ ID NO 21
<211> LENGTH: 43
<212> TYPE: PRT
<213> ORGANISM: Unknown
<220> FEATURE:
<223> OTHER INFORMATION: Description of Unknown Organism: Hypothetical wall-associated protein fragment

<400> SEQUENCE: 21

```
Thr Tyr Thr Val Lys Ser Gly Asp Thr Leu Trp Gly Ile Ser Gln Arg
1               5                   10                  15

Tyr Gly Ile Ser Val Ala Gln Ile Gln Ser Ala Asn Asn Leu Lys Ser
            20                  25                  30

Thr Ile Ile Tyr Ile Gly Gln Lys Leu Leu Leu
        35                  40
```

<210> SEQ ID NO 22
<211> LENGTH: 60
<212> TYPE: PRT
<213> ORGANISM: Unknown
<220> FEATURE:
<223> OTHER INFORMATION: Description of Unknown Organism: Hypothetical wall-associated protein fragment

<400> SEQUENCE: 22

```
Thr Tyr Thr Val Lys Lys Gly Asp Thr Leu Trp Asp Ile Ala Gly Arg
1               5                   10                  15

Phe Tyr Gly Asn Ser Thr Gln Trp Arg Lys Ile Trp Asn Ala Asn Lys
            20                  25                  30

Thr Ala Met Ile Lys Arg Ser Lys Arg Asn Ile Arg Gln Pro Gly His
        35                  40                  45

Trp Ile Phe Pro Gly Gln Lys Leu Lys Ile Pro Gln
    50                  55                  60
```

```
<210> SEQ ID NO 23
<211> LENGTH: 60
<212> TYPE: PRT
<213> ORGANISM: Unknown
<220> FEATURE:
<223> OTHER INFORMATION: Description of Unknown Organism: Hypothetical
      wall-associated protein fragment

<400> SEQUENCE: 23

Thr Tyr Thr Val Lys Lys Gly Asp Thr Leu Trp Asp Leu Ala Gly Lys
1               5                   10                  15

Phe Tyr Gly Asp Ser Thr Lys Trp Arg Lys Ile Trp Lys Val Asn Lys
            20                  25                  30

Lys Ala Met Ile Lys Arg Ser Lys Arg Asn Ile Arg Gln Pro Gly His
        35                  40                  45

Trp Ile Phe Pro Gly Gln Lys Leu Lys Ile Pro Gln
    50                  55                  60


<210> SEQ ID NO 24
<211> LENGTH: 167
<212> TYPE: PRT
<213> ORGANISM: Mycobacterium tuberculosis

<400> SEQUENCE: 24

Ala Pro Pro Val Glu Leu Ala Ala Asn Asp Leu Pro Ala Pro Leu Gly
1               5                   10                  15

Glu Pro Leu Pro Ala Ala Pro Ala Asp Pro Ala Pro Pro Ala Asp Leu
            20                  25                  30

Ala Pro Pro Ala Pro Ala Asp Val Ala Pro Pro Val Glu Leu Ala Val
        35                  40                  45

Asn Asp Leu Pro Ala Pro Leu Gly Glu Pro Leu Pro Ala Ala Pro Ala
    50                  55                  60

Asp Pro Ala Pro Pro Ala Asp Leu Ala Pro Pro Ala Pro Ala Asp Leu
65                  70                  75                  80

Ala Pro Pro Ala Pro Ala Asp Leu Ala Pro Pro Ala Pro Ala Asp Leu
                85                  90                  95

Ala Pro Pro Val Glu Leu Ala Val Asn Asp Leu Pro Ala Pro Leu Gly
            100                 105                 110

Glu Pro Leu Pro Ala Ala Pro Ala Glu Leu Ala Pro Pro Ala Asp Leu
        115                 120                 125

Ala Pro Ala Ser Ala Asp Leu Ala Pro Pro Ala Pro Ala Asp Leu Ala
    130                 135                 140

Pro Pro Ala Pro Ala Glu Leu Ala Pro Pro Ala Pro Ala Asp Leu Ala
145                 150                 155                 160

Pro Pro Ala Ala Val Asn Glu
                165


<210> SEQ ID NO 25
<211> LENGTH: 11
<212> TYPE: PRT
<213> ORGANISM: Mycobacterium tuberculosis

<400> SEQUENCE: 25

Ala Pro Pro Val Glu Leu Ala Ala Asn Asp Leu
1               5                   10


<210> SEQ ID NO 26
<211> LENGTH: 11
<212> TYPE: PRT
<213> ORGANISM: Mycobacterium tuberculosis
```

<400> SEQUENCE: 26

Ala Pro Pro Val Glu Leu Ala Val Asn Asp Leu
1 5 10

<210> SEQ ID NO 27
<211> LENGTH: 15
<212> TYPE: PRT
<213> ORGANISM: Mycobacterium tuberculosis

<400> SEQUENCE: 27

Pro Ala Pro Leu Gly Glu Pro Leu Pro Ala Ala Pro Ala Glu Leu
1 5 10 15

<210> SEQ ID NO 28
<211> LENGTH: 15
<212> TYPE: PRT
<213> ORGANISM: Mycobacterium tuberculosis

<400> SEQUENCE: 28

Pro Ala Pro Leu Gly Glu Pro Leu Pro Ala Ala Pro Ala Glu Leu
1 5 10 15

<210> SEQ ID NO 29
<211> LENGTH: 7
<212> TYPE: PRT
<213> ORGANISM: Mycobacterium tuberculosis

<400> SEQUENCE: 29

Pro Ala Pro Pro Ala Asp Leu
1 5

<210> SEQ ID NO 30
<211> LENGTH: 8
<212> TYPE: PRT
<213> ORGANISM: Mycobacterium tuberculosis

<400> SEQUENCE: 30

Ala Pro Pro Ala Pro Ala Asp Leu
1 5

<210> SEQ ID NO 31
<211> LENGTH: 8
<212> TYPE: PRT
<213> ORGANISM: Mycobacterium tuberculosis

<400> SEQUENCE: 31

Ala Pro Pro Ala Pro Ala Asp Val
1 5

<210> SEQ ID NO 32
<211> LENGTH: 8
<212> TYPE: PRT
<213> ORGANISM: Mycobacterium tuberculosis

<400> SEQUENCE: 32

Ala Pro Pro Ala Pro Ala Glu Leu
1 5

<210> SEQ ID NO 33
<211> LENGTH: 8
<212> TYPE: PRT
<213> ORGANISM: Mycobacterium tuberculosis

<400> SEQUENCE: 33

```
Ala Pro Pro Ala Pro Ala Glu Val
1               5


<210> SEQ ID NO 34
<211> LENGTH: 478
<212> TYPE: PRT
<213> ORGANISM: Listeria monocytogenes

<400> SEQUENCE: 34

Met Asn Met Lys Lys Ala Thr Ile Ala Ala Thr Ala Gly Ile Ala Val
1               5                   10                  15

Thr Ala Phe Ala Ala Pro Thr Ile Ala Ser Ala Ser Thr Val Val Val
            20                  25                  30

Glu Ala Gly Asp Thr Leu Trp Gly Ile Ala Gln Ser Lys Gly Thr Thr
        35                  40                  45

Val Asp Ala Ile Lys Lys Ala Asn Asn Leu Thr Thr Asp Lys Ile Val
    50                  55                  60

Pro Gly Gln Lys Leu Gln Val Asn Asn Glu Val Ala Ala Ala Glu Lys
65                  70                  75                  80

Thr Glu Lys Ser Val Ser Ala Thr Trp Leu Asn Val Arg Thr Gly Ala
                85                  90                  95

Gly Val Asp Asn Ser Ile Ile Thr Ser Ile Lys Gly Gly Thr Lys Val
            100                 105                 110

Thr Val Glu Thr Thr Glu Ser Asn Gly Trp His Lys Ile Thr Tyr Asn
        115                 120                 125

Asp Gly Lys Thr Gly Phe Val Asn Gly Lys Tyr Leu Thr Asp Lys Ala
    130                 135                 140

Val Ser Thr Pro Val Ala Pro Thr Gln Glu Val Lys Lys Glu Thr Thr
145                 150                 155                 160

Thr Gln Gln Ala Ala Pro Val Ala Glu Thr Lys Thr Glu Val Lys Gln
                165                 170                 175

Thr Thr Gln Ala Thr Thr Pro Ala Pro Lys Val Ala Glu Thr Lys Glu
            180                 185                 190

Thr Pro Val Ile Asp Gln Asn Ala Thr Thr His Ala Val Lys Ser Gly
        195                 200                 205

Asp Thr Ile Trp Ala Leu Ser Val Lys Tyr Gly Val Ser Val Gln Asp
    210                 215                 220

Ile Met Ser Trp Asn Asn Leu Ser Ser Ser Ser Ile Tyr Val Gly Gln
225                 230                 235                 240

Lys Leu Ala Ile Lys Gln Thr Ala Asn Thr Ala Thr Pro Lys Ala Glu
                245                 250                 255

Val Lys Thr Glu Ala Pro Ala Ala Glu Lys Gln Ala Ala Pro Val Val
            260                 265                 270

Lys Glu Asn Thr Asn Thr Asn Thr Ala Thr Thr Glu Lys Lys Glu Thr
        275                 280                 285

Ala Thr Gln Gln Gln Thr Ala Pro Lys Ala Pro Thr Glu Ala Ala Lys
    290                 295                 300

Pro Ala Pro Ala Pro Ser Thr Asn Thr Asn Ala Asn Lys Thr Asn Thr
305                 310                 315                 320

Asn Thr Asn Thr Asn Asn Thr Asn Thr Pro Ser Lys Asn Thr Asn Thr
                325                 330                 335

Asn Ser Asn Thr Asn Thr Asn Thr Asn Ser Asn Thr Asn Ala Asn Gln
            340                 345                 350

Gly Ser Ser Asn Asn Asn Ser Asn Ser Ser Ala Ser Ala Ile Ile Ala
        355                 360                 365
```

```
Glu Ala Gln Lys His Leu Gly Lys Ala Tyr Ser Trp Gly Gly Asn Gly
    370                 375                 380

Pro Thr Thr Phe Asp Cys Ser Gly Tyr Thr Lys Tyr Val Phe Ala Lys
385                 390                 395                 400

Ala Gly Ile Ser Leu Pro Arg Thr Ser Gly Ala Gln Tyr Ala Ser Thr
                405                 410                 415

Thr Arg Ile Ser Glu Ser Gln Ala Lys Pro Gly Asp Leu Val Phe Phe
            420                 425                 430

Asp Tyr Gly Ser Gly Ile Ser His Val Gly Ile Tyr Val Gly Asn Gly
        435                 440                 445

Gln Met Ile Asn Ala Gln Asp Asn Gly Val Lys Tyr Asp Asn Ile His
    450                 455                 460

Gly Ser Gly Trp Gly Lys Tyr Leu Val Gly Phe Gly Arg Val
465                 470                 475


<210> SEQ ID NO 35
<211> LENGTH: 758
<212> TYPE: DNA
<213> ORGANISM: Micrococcus luteus
<220> FEATURE:
<221> NAME/KEY: CDS
<222> LOCATION: (66)..(728)

<400> SEQUENCE: 35

accaaggaga aggacgaccc cggtgtgcct cggccgccga tcagcgagga ctcgccatgg      60

acacc atg act ctc ttc acc act tcc gcc acc cgc tcc cgc cgt gcc acc     110
      Met Thr Leu Phe Thr Thr Ser Ala Thr Arg Ser Arg Arg Ala Thr
      1               5                   10                  15

gcc tcg atc gtc gcg ggc atg acc ctc gcc ggc gcc gcc gcc gtg ggc      158
Ala Ser Ile Val Ala Gly Met Thr Leu Ala Gly Ala Ala Ala Val Gly
                20                  25                  30

ttc tcc gcc ccg gcc cag gcc gcc acc gtg gac acc tgg gac cgc ctc      206
Phe Ser Ala Pro Ala Gln Ala Ala Thr Val Asp Thr Trp Asp Arg Leu
            35                  40                  45

gcc gag tgc gag tcc aac ggc acc tgg gac atc aac acc ggc aac ggc      254
Ala Glu Cys Glu Ser Asn Gly Thr Trp Asp Ile Asn Thr Gly Asn Gly
        50                  55                  60

ttc tac ggc ggc gtg cag ttc acc ctg tcc tcc tgg cag gcc gtc ggc      302
Phe Tyr Gly Gly Val Gln Phe Thr Leu Ser Ser Trp Gln Ala Val Gly
    65                  70                  75

ggc gaa ggc tac ccg cac cag gcc tcg aag gcc gag cag atc aag cgc      350
Gly Glu Gly Tyr Pro His Gln Ala Ser Lys Ala Glu Gln Ile Lys Arg
80                  85                  90                  95

gcc gag atc ctc cag gac ctg cag ggc tgg ggc gcg tgg ccg ctg tgc      398
Ala Glu Ile Leu Gln Asp Leu Gln Gly Trp Gly Ala Trp Pro Leu Cys
                100                 105                 110

tcg cag aag ctg ggc ctg acc cag gct gac gcg gac gcc ggt gac gtg      446
Ser Gln Lys Leu Gly Leu Thr Gln Ala Asp Ala Asp Ala Gly Asp Val
            115                 120                 125

gac gcc acc gag gcc gcc ccg gtc gcc gtg gag cgc acg gcc acc gtg      494
Asp Ala Thr Glu Ala Ala Pro Val Ala Val Glu Arg Thr Ala Thr Val
        130                 135                 140

cag cgc cag tcc gcc gcg gac gag gct gcc gcc gag cag gcc gct gcc      542
Gln Arg Gln Ser Ala Ala Asp Glu Ala Ala Ala Glu Gln Ala Ala Ala
    145                 150                 155

gcg gag cag gcc gtc gtc gcc gag gcc gag acc atc gtc gtc aag tcc      590
Ala Glu Gln Ala Val Val Ala Glu Ala Glu Thr Ile Val Val Lys Ser
160                 165                 170                 175

ggt gac tcc ctc tgg acg ctc gcc aac gag tac gag gtg gag ggt ggc      638
Gly Asp Ser Leu Trp Thr Leu Ala Asn Glu Tyr Glu Val Glu Gly Gly
```

```
                180                 185                 190

tgg acc gcc ctc tac gag gcc aac aag ggc gcc gtc tcc gac gcc gcc      686
Trp Thr Ala Leu Tyr Glu Ala Asn Lys Gly Ala Val Ser Asp Ala Ala
            195                 200                 205

gtg atc tac gtc ggc cag gag ctc gtc ctg ccg cag gcc tga              728
Val Ile Tyr Val Gly Gln Glu Leu Val Leu Pro Gln Ala
        210                 215                 220

gacgcctgac cggccccccg gaccggtacc                                     758


<210> SEQ ID NO 36
<211> LENGTH: 220
<212> TYPE: PRT
<213> ORGANISM: Micrococcus luteus

<400> SEQUENCE: 36

Met Thr Leu Phe Thr Thr Ser Ala Thr Arg Ser Arg Arg Ala Thr Ala
1               5                   10                  15

Ser Ile Val Ala Gly Met Thr Leu Ala Gly Ala Ala Ala Val Gly Phe
            20                  25                  30

Ser Ala Pro Ala Gln Ala Ala Thr Val Asp Thr Trp Asp Arg Leu Ala
        35                  40                  45

Glu Cys Glu Ser Asn Gly Thr Trp Asp Ile Asn Thr Gly Asn Gly Phe
    50                  55                  60

Tyr Gly Gly Val Gln Phe Thr Leu Ser Ser Trp Gln Ala Val Gly Gly
65                  70                  75                  80

Glu Gly Tyr Pro His Gln Ala Ser Lys Ala Glu Gln Ile Lys Arg Ala
                85                  90                  95

Glu Ile Leu Gln Asp Leu Gln Gly Trp Gly Ala Trp Pro Leu Cys Ser
            100                 105                 110

Gln Lys Leu Gly Leu Thr Gln Ala Asp Ala Asp Ala Gly Asp Val Asp
        115                 120                 125

Ala Thr Glu Ala Ala Pro Val Ala Val Glu Arg Thr Ala Thr Val Gln
    130                 135                 140

Arg Gln Ser Ala Ala Asp Glu Ala Ala Ala Glu Gln Ala Ala Ala Ala
145                 150                 155                 160

Glu Gln Ala Val Val Ala Glu Ala Glu Thr Ile Val Val Lys Ser Gly
                165                 170                 175

Asp Ser Leu Trp Thr Leu Ala Asn Glu Tyr Glu Val Glu Gly Gly Trp
            180                 185                 190

Thr Ala Leu Tyr Glu Ala Asn Lys Gly Ala Val Ser Asp Ala Ala Val
        195                 200                 205

Ile Tyr Val Gly Gln Glu Leu Val Leu Pro Gln Ala
    210                 215                 220


<210> SEQ ID NO 37
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37

gcsacsgtsg acacstggga ccgsctsgcs gag                                  33


<210> SEQ ID NO 38
<211> LENGTH: 19
<212> TYPE: PRT
<213> ORGANISM: Micrococcus luteus
```

<220> FEATURE:
<221> NAME/KEY: MOD_RES
<222> LOCATION: (13)..(13)
<223> OTHER INFORMATION: Variable amino acid
<220> FEATURE:
<221> NAME/KEY: MOD_RES
<222> LOCATION: (18)..(18)
<223> OTHER INFORMATION: Variable amino acid

<400> SEQUENCE: 38

Ala Thr Val Asp Thr Trp Asp Arg Leu Ala Glu Glu Xaa Ser Asn Gly
1 5 10 15

Thr Xaa Asp

<210> SEQ ID NO 39
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 39
ccgccgtaga agccgttg 18

<210> SEQ ID NO 40
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 40
agttcaccct gtcctcctg 19

<210> SEQ ID NO 41
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (9)..(9)
<223> OTHER INFORMATION: i
<220> FEATURE:
<221> NAME/KEY: modified_base
<222> LOCATION: (15)..(15)
<223> OTHER INFORMATION: i
<220> FEATURE:
<221> NAME/KEY: modified_base
<222> LOCATION: (21)..(21)
<223> OTHER INFORMATION: i

<400> SEQUENCE: 41
gcytgrtgng grtanccytc ncc 23

<210> SEQ ID NO 42
<211> LENGTH: 12
<212> TYPE: PRT
<213> ORGANISM: Micrococcus luteus

<400> SEQUENCE: 42

Val Gly Gly Glu Gly Tyr Pro His Gln Ala Ser Lys
1 5 10

<210> SEQ ID NO 43

```
<211> LENGTH: 182
<212> TYPE: PRT
<213> ORGANISM: Micrococcus luteus

<400> SEQUENCE: 43

Ala Thr Val Asp Thr Trp Asp Arg Leu Ala Glu Cys Glu Ser Asn Gly
1               5                   10                  15

Thr Trp Asp Ile Asn Thr Gly Asn Gly Phe Tyr Gly Gly Val Gln Phe
            20                  25                  30

Thr Leu Ser Ser Trp Gln Ala Val Gly Gly Glu Gly Tyr Pro His Gln
        35                  40                  45

Ala Ser Lys Ala Glu Gln Ile Lys Arg Ala Glu Ile Leu Gln Asp Leu
    50                  55                  60

Gln Gly Trp Gly Ala Trp Pro Leu Cys Ser Gln Lys Leu Gly Leu Thr
65                  70                  75                  80

Gln Ala Asp Ala Asp Ala Gly Asp Val Asp Ala Thr Glu Ala Ala Pro
                85                  90                  95

Val Ala Val Glu Arg Thr Ala Thr Val Gln Arg Gln Ser Ala Ala Asp
            100                 105                 110

Glu Ala Ala Ala Glu Gln Ala Ala Ala Ala Glu Gln Ala Val Val Ala
        115                 120                 125

Glu Ala Glu Thr Ile Val Val Lys Ser Gly Asp Ser Leu Trp Thr Leu
    130                 135                 140

Ala Asn Glu Tyr Glu Val Glu Gly Gly Trp Thr Ala Leu Tyr Glu Ala
145                 150                 155                 160

Asn Lys Gly Ala Val Ser Asp Ala Ala Val Ile Tyr Val Gly Gln Glu
                165                 170                 175

Leu Val Leu Pro Gln Ala
            180


<210> SEQ ID NO 44
<211> LENGTH: 299
<212> TYPE: DNA
<213> ORGANISM: Streptomyces coelicolor
<220> FEATURE:
<221> NAME/KEY: CDS
<222> LOCATION: (3)..(299)

<400> SEQUENCE: 44

gg atc cgc acc gcc gcg gta acc ctg gtc gcc gcg acc gca ctc ggg        47
   Ile Arg Thr Ala Ala Val Thr Leu Val Ala Ala Thr Ala Leu Gly
   1               5                   10                  15

gcg acc ggc gaa gcg gtg gcc gcg ccc tcg gcg ccc ctg cgc acc gac        95
Ala Thr Gly Glu Ala Val Ala Ala Pro Ser Ala Pro Leu Arg Thr Asp
                20                  25                  30

tgg gac gcc atc gcc gcg tgc gag tcc agc ggc aac tgg cag gcg aac       143
Trp Asp Ala Ile Ala Ala Cys Glu Ser Ser Gly Asn Trp Gln Ala Asn
            35                  40                  45

acc ggc aac ggc tac tac ggc ggc ctg cag ttc gca cgg tcc agc tgg       191
Thr Gly Asn Gly Tyr Tyr Gly Gly Leu Gln Phe Ala Arg Ser Ser Trp
        50                  55                  60

atc gcc gcc ggc ggc ctc aag tac gcc ccg cgc gcg gac ctc gcc acc       239
Ile Ala Ala Gly Gly Leu Lys Tyr Ala Pro Arg Ala Asp Leu Ala Thr
    65                  70                  75

cgc ggc gag cag atc gcc gtg gcg gaa cgc ctc gcc cgt ctg cag ggg       287
Arg Gly Glu Gln Ile Ala Val Ala Glu Arg Leu Ala Arg Leu Gln Gly
80                  85                  90                  95

atg tcc gcc tgg                                                       299
Met Ser Ala Trp
```

<210> SEQ ID NO 45
<211> LENGTH: 99
<212> TYPE: PRT
<213> ORGANISM: Streptomyces coelicolor

<400> SEQUENCE: 45

```
Ile Arg Thr Ala Ala Val Thr Leu Val Ala Ala Thr Ala Leu Gly Ala
1               5                   10                  15

Thr Gly Glu Ala Val Ala Ala Pro Ser Ala Pro Leu Arg Thr Asp Trp
            20                  25                  30

Asp Ala Ile Ala Ala Cys Glu Ser Ser Gly Asn Trp Gln Ala Asn Thr
        35                  40                  45

Gly Asn Gly Tyr Tyr Gly Gly Leu Gln Phe Ala Arg Ser Ser Trp Ile
    50                  55                  60

Ala Ala Gly Gly Leu Lys Tyr Ala Pro Arg Ala Asp Leu Ala Thr Arg
65                  70                  75                  80

Gly Glu Gln Ile Ala Val Ala Glu Arg Leu Ala Arg Leu Gln Gly Met
                85                  90                  95

Ser Ala Trp
```

<210> SEQ ID NO 46
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 46
gtcagaattc atatggccac cgtggacacc tggg 34

<210> SEQ ID NO 47
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 47
tgacggatcc tattaggcct gcggcaggac gag 33

<210> SEQ ID NO 48
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 48
atcagaattc atatggacga catcgattgg gacgc 35

<210> SEQ ID NO 49
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 49
cgcaggatcc cctcaatcgt ccctgctcc 29

<210> SEQ ID NO 50
<211> LENGTH: 23
<212> TYPE: DNA

<213> ORGANISM: Artificial Sequence
<220> FEATURE:
<223> OTHER INFORMATION: Description of Artificial Sequence: Primer

<400> SEQUENCE: 50
gaagagaatt ccttccatca cga 23

<210> SEQ ID NO 51
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 51
ccaaacgaat tcggtcaatc ac 22

<210> SEQ ID NO 52
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 52
gcaaggatcc cagactaaaa aaacag 26

<210> SEQ ID NO 53
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 53
atcaggatcc atattattag tttaaga 27

<210> SEQ ID NO 54
<211> LENGTH: 663
<212> TYPE: DNA
<213> ORGANISM: Micrococcus luteus
<220> FEATURE:
<221> NAME/KEY: CDS
<222> LOCATION: (1)..(663)

<400> SEQUENCE: 54

```
atg act ctc ttc acc act tcc gcc acc cgc tcc cgc cgt gcc acc gcc       48
Met Thr Leu Phe Thr Thr Ser Ala Thr Arg Ser Arg Arg Ala Thr Ala
1               5                   10                  15

tcg atc gtc gcg ggc atg acc ctc gcc ggc gcc gcc gcc gtg ggc ttc       96
Ser Ile Val Ala Gly Met Thr Leu Ala Gly Ala Ala Ala Val Gly Phe
            20                  25                  30

tcc gcc ccg gcc cag gcc gcc acc gtg gac acc tgg gac cgc ctc gcc      144
Ser Ala Pro Ala Gln Ala Ala Thr Val Asp Thr Trp Asp Arg Leu Ala
        35                  40                  45

gag tgc gag tcc aac ggc acc tgg gac atc aac acc ggc aac ggc ttc      192
Glu Cys Glu Ser Asn Gly Thr Trp Asp Ile Asn Thr Gly Asn Gly Phe
    50                  55                  60

tac ggc ggc gtg cag ttc acc ctg tcc tcc tgg cag gcc gtc ggc ggc      240
Tyr Gly Gly Val Gln Phe Thr Leu Ser Ser Trp Gln Ala Val Gly Gly
65                  70                  75                  80

gaa ggc tac ccg cac cag gcc tcg aag gcc gag cag atc aag cgc gcc      288
Glu Gly Tyr Pro His Gln Ala Ser Lys Ala Glu Gln Ile Lys Arg Ala
                85                  90                  95

gag atc ctc cag gac ctg cag ggc tgg ggc gcg tgg ccg ctg tgc tcg      336
```

```
Glu Ile Leu Gln Asp Leu Gln Gly Trp Gly Ala Trp Pro Leu Cys Ser
            100                 105                 110

cag aag ctg ggc ctg acc cag gct gac gcg gac gcc ggt gac gtg gac      384
Gln Lys Leu Gly Leu Thr Gln Ala Asp Ala Asp Ala Gly Asp Val Asp
        115                 120                 125

gcc acc gag gcc gcc ccg gtc gcc gtg gag cgc acg gcc acc gtg cag      432
Ala Thr Glu Ala Ala Pro Val Ala Val Glu Arg Thr Ala Thr Val Gln
    130                 135                 140

cgc cag tcc gcc gcg gac gag gct gcc gcc gag cag gcc gct gcc gcg      480
Arg Gln Ser Ala Ala Asp Glu Ala Ala Ala Glu Gln Ala Ala Ala Ala
145                 150                 155                 160

gag cag gcc gtc gtc gcc gag gcc gag acc atc gtc gtc aag tcc ggt      528
Glu Gln Ala Val Val Ala Glu Ala Glu Thr Ile Val Val Lys Ser Gly
                165                 170                 175

gac tcc ctc tgg acg ctc gcc aac gag tac gag gtg gag ggt ggc tgg      576
Asp Ser Leu Trp Thr Leu Ala Asn Glu Tyr Glu Val Glu Gly Gly Trp
            180                 185                 190

acc gcc ctc tac gag gcc aac aag ggc gcc gtc tcc gac gcc gcc gtg      624
Thr Ala Leu Tyr Glu Ala Asn Lys Gly Ala Val Ser Asp Ala Ala Val
        195                 200                 205

atc tac gtc ggc cag gag ctc gtc ctg ccg cag gcc tga                  663
Ile Tyr Val Gly Gln Glu Leu Val Leu Pro Gln Ala
    210                 215                 220


<210> SEQ ID NO 55
<211> LENGTH: 6
<212> TYPE: PRT
<213> ORGANISM: Mycobacterium tuberculosis

<400> SEQUENCE: 55

Ala Pro Pro Ala Asp Leu
1               5


<210> SEQ ID NO 56
<211> LENGTH: 7
<212> TYPE: PRT
<213> ORGANISM: Mycobacterium tuberculosis

<400> SEQUENCE: 56

Ala Pro Ala Ser Ala Asp Leu
1               5


<210> SEQ ID NO 57
<211> LENGTH: 8
<212> TYPE: PRT
<213> ORGANISM: Mycobacterium tuberculosis

<400> SEQUENCE: 57

Ala Pro Pro Ala Pro Ala Glu Leu
1               5


<210> SEQ ID NO 58
<211> LENGTH: 4
<212> TYPE: PRT
<213> ORGANISM: Mycobacterium tuberculosis

<400> SEQUENCE: 58

Ala Pro Pro Ala
1


<210> SEQ ID NO 59
<211> LENGTH: 4
<212> TYPE: PRT
<213> ORGANISM: Mycobacterium tuberculosis
```

<400> SEQUENCE: 59

Ala Val Asn Glu
1

<210> SEQ ID NO 60
<211> LENGTH: 15
<212> TYPE: PRT
<213> ORGANISM: Mycobacterium tuberculosis
<220> FEATURE:
<221> NAME/KEY: MOD_RES
<222> LOCATION: (14)..(14)
<223> OTHER INFORMATION: Asp or Glu

<400> SEQUENCE: 60

Pro Ala Pro Leu Gly Glu Pro Leu Pro Ala Ala Pro Ala Xaa Leu
1 5 10 15

<210> SEQ ID NO 61
<211> LENGTH: 8
<212> TYPE: PRT
<213> ORGANISM: Mycobacterium tuberculosis
<220> FEATURE:
<221> NAME/KEY: MOD_RES
<222> LOCATION: (7)..(7)
<223> OTHER INFORMATION: Asp or Glu
<220> FEATURE:
<221> NAME/KEY: MOD_RES
<222> LOCATION: (8)..(8)
<223> OTHER INFORMATION: Leu or Val

<400> SEQUENCE: 61

Ala Pro Pro Ala Pro Ala Xaa Xaa
1 5

<210> SEQ ID NO 62
<211> LENGTH: 11
<212> TYPE: PRT
<213> ORGANISM: Mycobacterium tuberculosis
<220> FEATURE:
<221> NAME/KEY: MOD_RES
<222> LOCATION: (8)..(8)
<223> OTHER INFORMATION: Ala or Val

<400> SEQUENCE: 62

Ala Pro Pro Val Glu Leu Ala Xaa Asn Asp Leu
1 5 10

<210> SEQ ID NO 63
<211> LENGTH: 14
<212> TYPE: PRT
<213> ORGANISM: Mycobacterium tuberculosis

<400> SEQUENCE: 63

Pro Ala Pro Leu Gly Glu Pro Leu Pro Ala Ala Pro Ala Asp
1 5 10

<210> SEQ ID NO 64
<211> LENGTH: 9
<212> TYPE: PRT
<213> ORGANISM: Micrococcus luteus

<400> SEQUENCE: 64

Lys Ala Glu Gln Ile Lys Arg Ala Glu
1 5

<210> SEQ ID NO 65
<211> LENGTH: 5

-continued

```
<212> TYPE: PRT
<213> ORGANISM: Micrococcus luteus

<400> SEQUENCE: 65

Asp Thr Trp Asp Arg
1               5
```

BACTERIAL PHEROMONES AND USES THEREOF

RELATED INFORMATION

This application is a divisional application of U.S. application Ser. No. 09/445,289, filed May 11, 2000, pending, which is the U.S. national phase application, pursuant to 35 U.S.C. §371, of international patent application Ser. No. PCT/GB98/01619, filed Jun. 3, 1998, designating the United States and published in English as WO 98/55624 on Dec. 10, 1998, which claims priority to GB 97113898.8, filed Jun. 4, 1997 and GB 9811221.2, filed May 27, 1998, the disclosures of each of which applications are incorporated herein in their entirety by this reference.

The sequence listing in the 57,763 byte text file "2011-10-04_118160-00302_ST25.txt" that was created Oct. 4, 2011 and filed electronically by EFS-Web on Oct. 4, 2011 is incorporated herein by reference.

FIELD OF THE INVENTION

The present invention relates to RP-factors, their cognate receptors, convertases, respective genes and to inhibitors or mimetics thereof. In particular, the invention relates to antibodies, pharmaceutical compositions and (therapeutic, diagnostic) methods based on the RP-factors and their receptors/convertases.

INTRODUCTION

Bacterial Pheromones

It is known that certain chemicals may mediate intercellular communication in bacterial cultures. Such communication has been shown to be of importance during sporulation, conjugation, changes in virulence and in bioluminescence. It is now clear that a variety of different autocrine and/or paracrine chemical compounds ("pheromones") produced as secondary metabolites are responsible for such social behaviour in prokaryotes (see e.g. 25 Kell et al., 1995, Trends Ecol. Evolution, 10, 126-129).

Pheromones may be distinguished from nutrients inter alia in that: (i) they are produced by the organisms themselves, (ii) they are active at very low concentrations (e.g. at picomolar or nanomolar concentrations), and (iii) with the exception of prohormone processing, their metabolism is not necessary for activity (although they may of course ultimately be degraded).

The chemical nature of these pheromonal compounds varies widely: those associated with Gram-negative organisms tend to be of low molecular weight (e.g. N-acyl homoserine lactone derivatives), whilst a number of Gram-positive organisms use proteins and polypeptides (Kell et al, 1995, ibidem).

Pheromones are also known to play an important role in the development of bacterial cultures. For unstressed (uninjured) bacteria and optimal growth media, the "self-promoting" mode of culture growth is normally masked due to the high rate of production of growth factors and the sensitivity of the cells to these pheromones. Only under unfavourable conditions (for example, poor growth media, small initial inocula and/or starved cells) is this self-promoting behaviour "visible".

For example, a dramatic reduction in the length of the lag phase of cultures of *Nitrosomonas europea* is mediated by N-(3-oxo-hexanoyl) homoserine lactone, and chorionic gonadotropin-like ligand (a 48 kD protein) had similar growth-stimulating activity for *Xanthomonas maltophila*. A number of mammalian hormones (including peptide and steroid hormones as well as cytokines) have also been shown to exhibit potent growth-stimulating activities for both Gram-positive and Gram-negative bacteria.

Latency and Resuscitation

The ability of a microbial cell to grow and divide on a nutrient agar plate constitutes the benchmark method for determining the number of living cells in a sample of interest. However, it is also widely recognised that, especially in nature, the distinction between life and non-life is not absolute; many cells may exist in "dormant" or "moribund" forms or states and will not produce colonies on nutrient media (i.e. are "non-culturable"). However, these dormant or latent cells are not dead: they can be returned, by a process known as resuscitation, to a state of viability/culturability.

For example, it is known that cells of the (high-G+C Gram-positive) bacterium *Micrococcus luteus* can enter a state of true dormancy from which they may be resuscitated by culture supernatants, even in the absence of any 'initially viable' cells.

The latent state has profound medical implications: many pathogenic bacteria (including pathogenic mycobacteria such as *M. tuberculosis*) are known to persist for extended periods in latent states in a host organism. Indeed, tuberculosis is a re-emergent infection of great concern, and it is recognised in particular that the causative organism (*Mycobacterium tuberculosis*) can lie dormant (remain latent) in patients and carriers for periods of years.

The latent state also has important commercial implications, since it complicates many laboratory methods for the detection, cultivation and enumeration of bacteria (for example in the food and healthcare industries).

There is therefore a pressing need to understand the physiological bases of latency and resuscitation.

SUMMARY OF THE INVENTION

The present invention is based, at least in part, on the discovery of a new class of pheromones which stimulate the resuscitation of bacteria after true dormancy. This "resuscitation factor" (herein embraced by the term "RP-factor") may exhibit activity at picomolar concentrations (implying a non-nutritional role). The elucidation of the structure of the pheromones at the amino acid sequence level has also permitted the present inventors to describe a larger family of proteins, some members of which act more broadly as regulators of cellular growth or replication and not necessarily as resuscitation promoting factors. Further sequence comparisons have also led to the identification of the cognate receptors, at least some of which share certain sequence similarities with their cognate RP-factors.

Thus, in a first aspect of the present invention there is provided an isolated RP-factor.

RP-Factors

The term "RP-factor" is used herein to encompass any representative of that family of substances the members of which are capable of resuscitating dormant, moribund or latent cells (e.g. dormant bacterial cells). In addition, the RP-factors of the invention may also exhibit growth-stimulatory activity with respect to growing cells (e.g. growing bacterial cells), and/or may be competent to reduce the lag time of cell (e.g. bacterial cell) cultures. The resuscitation activity (and optionally also the growth-stimulatory activity or lag-time reducing activity) of the RP-factor may be specific for a particular (bacterial) cell (e.g. specific for one or more pathogenic mycobacteria), or may be non-specific. Specificity may be manipulated for example by engineering (e.g. by mutagenesis or chimaerisation, as herein described) of the specificity-determining domain(s) of the RP-factor or by replacement of the signalling domain.

The term "RP-factor" is also used herein in a somewhat broader sense to encompass polypeptides which are expressed by bacteria and which regulate (e.g. promote, trigger, prevent or impair) the growth or multiplication of a cell (the "target cell") by acting as signalling moieties in conjunction with (e.g. by binding to) cognate cellular receptors. Such polypeptides may be referred to herein as bacterial cytokines.

The RP-factors of the invention therefore include bacterial cytokines which may or may not be capable of resuscitating dormant, moribund or latent cells (e.g. dormant bacterial cells) and/or exhibit growth-stimulatory activity with respect to growing cells (e.g. growing bacterial cells). They may or may not also be competent to reduce the lag time associated with the growth of cell (e.g. bacterial cell) cultures. Moreover, some bacterial cytokines which fall within the scope of the term "RP-factor" as defined herein may even prevent or impair the growth of the target cells (particularly where the target cells are eukaryotic (e.g. mammalian) cells).

The RP-factors of the invention may fall into at least two functional classes: autosignalling factors and allosignalling factors. Autosignalling factors act to regulate the growth of the bacterial cell in which they were expressed (i.e. they act as bacterial autocrine factors), while allosignallers act to regulate the growth of other cells (i.e. they act as bacterial paracrine factors). Autosignalling factors therefore act as self-regulators of bacterial cell growth, and may be essential for viability and/or growth. Some RP-factors may function as both auto- and allosignalling cytokines.

Allosignalling factors may exhibit a range of different specificities. Some may act solely on other bacterial cells of the same species as the cell in which they were expressed ("homoactive" factors), while others may act on cells of one or more other species ("heteroactive" factors). Heteroactive factors may exhibit a broad range of specificity: they may act on several different species (for example, in a genus-specific manner), or may be species-specific. Some heteroactive bacterial factors may act on eukaryotic cells, and may be specific for particular cell-types. For example, some heteroactive bacterial cytokines (particularly those produced by certain pathogens) may act on mammalian cells (e.g. mammalian epithelial, endothelial or immune cells), and may be tissue- or cell-type specific.

Notwithstanding the above explanation, it is postulated that the specificity of at least some RP-factors may be concentration dependent. In these cases, the specificity of any given RP-factor falls within a continuum, so that an autosignalling RP-factor may mediate cross-talk and so exhibit allosignalling activity when present at sufficiently high concentrations. Similarly, allosignalling RP-factors may exhibit homo- or heteroactivity depending on concentration.

The RP-factor may be translocated through the cell membrane, whereafter it may be secreted into the surrounding environment or remain associated with the surface of the cell. Thus, at least two classes of RP-factor may exist: secreted and non-secreted. The secreted RP-factors are characterised by the presence of a secretory signal sequence (the presence of which is readily recognised by those skilled in the art on the basis of the presence of DNA and/or amino acid sequence motifs). The non-secreted RP-factors may be cell-associated or cytosolic factors. Both classes of RP-factor may exist in a single cellular source (e.g. in a single bacterial source). Both classes of RP-factor find application in the invention.

Non-secreted RP-factors may act in at least four different ways: (a) as a membrane-anchored juxtacrine factor mediating a growth regulating signal between two different cells in close physical proximity or contact; and/or (b) as an intercellular signalling moiety upon cleavage by an enzyme (e.g. a convertase, as herein defined) which releases a soluble signalling moiety into the extracellular milieu; and/or (c) as an autocrine factor via binding to cognate receptors located on the surface of the cell in which the non-secreted factor is expressed or acting entirely intracellularly; and/or (d) as a cognate receptor for another non-secreted or secreted RP-factor.

Thus, the RP-factors of the invention may include the nine factors identified by the sequences shown in FIG. 1A and the five factors identified by those shown in FIG. 1B, together with their species variants, allelic forms, homologues, derivatives, muteins and corresponding secreted/nonsecreted forms (vide infra).

Preferably, the RP-factors of the invention are species variants, allelic forms, homologues, derivatives, muteins and corresponding secreted/nonsecreted forms of any one of the nine factors identified by the sequences shown in FIG. 1A and the five factors identified by those shown in FIG. 1B.

The RP-factors may be synthesised in the form of a precursor which is processed to produce a mature form. Such processing may proceed via various intermediate (pro-) forms. Such precursors, intermediate forms and mature proteins are all intended to be covered by the term "RP-factor" as used herein, except where indicated otherwise. As used herein, the term "pro-RP-factor" specifically defines any of various precursors (which may or may not be active) of a mature RP-factor.

The processing may comprise proteolytic cleavage and/or secretion. The precursors may be inactive, and become active on processing as a mature form. The precursors may comprise proteins having secretory leader sequences which are removed during secretion (pre-forms). Such forms are herein referred to as "pre-RP-factor or pre-pro-RP-factors". As explained above, such pre- or prepro-forms are also intended to be covered by the term "RP-factor" as used herein, except where indicated otherwise.

Processing may be attendant on the binding of an RP-factor precursor to a cognate receptor. Such receptors may then directly (or indirectly) cleave the precursor to produce a more mature form of the RP-factor. Such processing may occur as a cascade, involving several receptor-processing complexes, and so ultimately result in the production of a mature RP-factor which then acts as a signalling moiety by binding to a terminal (signal transducing) receptor.

In such processing, the proximal (or intermediate) receptors may function as convertases, and the terminal receptor as a signal transducer. However, a receptor may function as both a convertase and a signal transducer. As used herein, the term "convertase" is intended to define a molecule which binds an RP-factor precursor and (directly or indirectly) processes it to produce a more mature form. They may, for example, have protease activity.

The receptors/convertases discussed above may be disposed at the cell surface (e.g. membrane bound), cytosolic or extracellular.

Preferably, the RP-factor is derived from a bacterium (e.g. a pathogenic bacterium). Particularly preferred are RP-factors derived from high G+C Gram-positive bacteria.

However, the inventors have also discovered RP-factor family members in representatives of the low G+C Gram-positive organisms, including *Bacillus subtilis* and clostridia. Thus, RP-factors derived from low G+C Gram-positive bacteria (e.g. pathogenic low G+C Gram-positive bacteria) are also preferred according to the invention. Examples of the latter include: *Streptococcus* spp., *Staphylococcus* spp., *Listeria* spp., *Bacillus* spp., *Clostridium* spp. and *Lactobacillus* spp.

The invention also contemplates homologues, allelic forms, species variants, derivatives, muteins or equivalents of the RP-factors and RP-factor receptors/convertases of the invention.

Preferably, the homologues, derivatives, muteins or equivalents of the RP-factor of the invention have at least 20% identity with any one of the particular amino acid sequences shown in FIGS. 1A and 1B.

Particularly preferred are homologues, derivatives, muteins or equivalents of the RP-factor of the invention which have at least 30% identity, for example at least 35%, 40%, 45%, 50%, 55%, 60%, 65%, 70%, 75%, 80%, 85%, 90%, 95% or 98% identity with any one of the particular amino acid sequences shown in FIGS. 1A and 1B.

The homologues, derivatives, muteins or equivalents of the RP-factor of the invention may have at least 25% homology with any one of the particular amino acid sequences shown in FIGS. 1A and 1B.

Particularly preferred are homologues, derivatives, muteins or equivalents of the RP-factor of the invention which have at least 30% homology, for example at least 35%, 40%, 45%, 50%, 55%, 60%, 65%, 70%, 75%, 80%, 85%, 90%, 95% or 98% homology with any one of the particular amino acid sequences shown in FIGS. 1A and 1B.

The invention also contemplates chimaeric RP-factors. These are factors which comprise one or more heterologous domains. In this context, a heterologous domain is a portion of an RP-factor which is derived from a different RP-factor to that from which the other domain(s) with which it is associated are derived. Such chimaeric RP-factors find particular utility in applications where the specificity and/or activity of the RP-factor is manipulated or altered.

The invention also contemplates all individual functional domains of the RP-factors of the invention as separate and independent entities.

The invention also contemplates recombinant RP-factor. As used herein, the term "recombinant" is intended to define material which has been produced by that body of techniques collectively known as "recombinant DNA technology" (for example, using the nucleic acid, vectors and or host cells described infra).

Cognate Receptors

In some cases, the cognate cellular receptor is a cell surface receptor: in other cases, it is a cytosolic receptor with which the cytokine interacts after uptake by the target cell. The receptors with which the RP-factors and/or bacterial cytokines of the invention interact may share certain structural motifs with the RP-factors/cytokines themselves. In particular, the receptors may contain a ligand binding domain which is structurally similar to the signalling domain of the cognate RP-factor/cytokine.

The receptors may also comprise a membrane anchor domain and a wall spanning domain.

Preferably, the cognate receptor comprises a receptor domain as hereinbelow defined and/or a wall spanning domain as hereinbelow defined and/or a membrane anchor.

Particularly preferred are cognate receptors comprising the amino acid sequence of MtubZ94752 as shown in FIG. 1A or the amino acid sequence of YabE from *B. subtilis* as shown in FIG. 1B.

The cognate receptors may also comprise derivative or equivalent sequences of amino acid residues which are as defined above but in which amino acids have been added, deleted or substituted (e.g. conservatively substituted), provided that biological activity (e.g. signalling or ligand-binding activity) is substantially retained.

The cognate receptors may also comprise derivative or equivalent sequences of amino acid residues which have at least 20% identity or homology with the amino acid sequence of MtubZ94752 as shown in FIG. 1A or the amino acid sequence of YabE from *B. subtilis* as shown in FIG. 1B, for example at least 30% identity or homology, for example at least 35%, 40%, 45%, 50%, 55%, 60%, 65%, 70%, 75%, 80%, 85%, 90%, 95% or 98% identity or homology therewith.

RP-Factor/Cognate Receptor Domain Structure

The RP-factors of the invention (including the bacterial cytokines as also defined herein) and their cognate receptors may comprise a plurality of discrete domains. These domains may be functionally and/or structurally distinct.

The RP-factors of the invention may be characterised by the presence of at least two functional domains: a secretory signal sequence (which may be wholly or partially absent in the active form of the factor) and a signalling domain. The signalling domain may fall into one of at least two distinct classes described in more detail infra.

Many RP-factors also comprise a third functional domain which mediates a physical association with the surface of the target cell (hereinafter referred to as the "localizing domain" and described in more detail infra).

The RP-factors of the invention may further comprise a specificity-determining domain, which may function in conjunction with the signalling domain.

Non-secreted RP-factors may further comprise a wall-spanning domain (described in more detail infra) and/or a membrane anchor.

The gross structure and/or amino acid sequence of the aforementioned domains may vary considerably. In particular, the structure of the surface localizing domain may differ according to the structure of the cell-wall of the target cell. For example, the surface localizing domain may fall into one of at least two distinct classes: class I (which may act on peptidoglycan) and class II (which may act on the outer lipid envelope found in mycobacteria).

The cognate receptors of the invention may be characterised by the presence of at least two functional domains: a receptor domain and a wall spanning domain. They may also comprise a membrane anchor. The receptor domain may be structurally similar to the signalling domain of the cognate RP-factor (as described in more detail infra).

Receptor/Signalling Domain, class I

This domain may be associated with RP-factors from high G+C Gram-positive bacteria (such as mycobacteria and *Micrococcus* spp.) and/or their cognate receptors. When present on RP-factors, the domain may be involved in receptor binding, and may for example bind a structurally similar domain on a cognate receptor. Thus, when present as part of an RP-factor of the invention, the domain is termed the "signalling domain", and when present in the cognate receptor, the domain is termed the "receptor domain".

The domain may comprise a sequence of amino acid residues, the identity and relative positions of which correspond to those residues indexed by asterisks in any one of the 9 sequences set out in FIG. 1A.

In preferred embodiments, the domain may comprise a sequence of amino acid residues, the identity and relative positions of which correspond to those residues indexed by asterisks and dots in any one of the 9 sequences set out in FIG. 1A.

In particularly preferred embodiments, the domain may comprise a sequence of amino acid residues, the identity and relative positions of which correspond to those residues highlighted in bold upper case type in any one of the 9 sequences set out in FIG. 1A.

In more particularly preferred embodiments, the domain may comprise a sequence of amino acid residues, the identity and relative positions of which correspond to those residues presented in upper case type in any one of the 9 sequences set out in FIG. 1A.

The domain may also comprise derivative or equivalent sequences of amino acid residues which are as defined above but in which amino acids have been added, deleted or substituted (e.g. conservatively substituted), provided that biological activity (e.g. signalling or ligand-binding activity) is substantially retained.

The domain may also comprise derivative or equivalent sequences of amino acid residues which have at least 20% identity or homology with any one of the particular amino acid sequences defined above, for example at least 30% identity or homology, for example at least 35%, 40%, 45%, 50%, 55%, 60%, 65%, 70%, 75%, 80%, 85%, 90%, 95% or 98% identity or homology therewith.

Receptor/Signalling Domain, Class II

This domain may be associated with RP-factors from low G+C Gram-positive bacteria (such as bacilli and clostridia) and/or their cognate receptors. When present on RP-factors, the domain may be involved in receptor binding, and may for example bind a structurally similar domain on a cognate receptor. Thus, when present as part of an RP-factor of the invention, the domain is termed the "signalling domain", and when present in the cognate receptor, the domain is termed the "receptor domain".

The domain may comprise a sequence of amino acid residues, the identity and relative positions of which correspond to those residues indexed by asterisks in any one of the 5 sequences set out in FIG. 1B(B).

In preferred embodiments, the domain may comprise a sequence of amino acid residues, the identity and relative positions of which correspond to those residues indexed by asterisks and dots in any one of the 5 sequences set out in FIG. 1B(B).

In particularly preferred embodiments, the domain may comprise a sequence of amino acid residues, the identity and relative positions of which correspond to those residues highlighted in bold upper case type in any one of the 5 sequences set out in FIG. 1B(B).

In more particularly preferred embodiments, the domain may comprise a sequence of amino acid residues, the identity and relative positions of which correspond to those residues presented in upper case type in any one of the 5 sequences set out in FIG. 1B(B).

The domain may also comprise derivative or equivalent sequences of amino acid residues which are as defined above but in which amino acids have been added, deleted or substituted (e.g. conservatively substituted), provided that biological activity (e.g. signalling or ligand-binding activity) is substantially retained.

The domain may also comprise derivative or equivalent sequences of amino acid residues which have at least 20% identity or homology with any one of the particular amino acid sequences defined above, for example at least 30% identity or homology, for example at least 35%, 40%, 45%, 50%, 55%, 60%, 65%, 70%, 75%, 80%, 85%, 90%, 95% or 98% identity or homology therewith.

Wall Spanning Domain

This domain may be associated with non-secreted RP-factors (e.g. cell-associated RP-factors or RP-factors which act as juxtacrine factors) and with the cognate receptors of the RP-factors of the invention. When present, the domain is involved in mediating an interaction with the cell wall such that the RP-factor/receptor as a whole may span it.

The wall spanning domain may therefore be bounded by cytosolic and extracellular regions in vivo. The domain is often associated with a membrane anchor, the two structural elements acting in concert to maintain the RP-factor/receptor at the cell surface.

The domain may comprise a sequence of amino acid residues, the identity and relative positions of which correspond to those residues presented in upper case and indexed by hashes (#) in any one of the 5 sequences set out in FIG. 1B(A).

In preferred embodiments, the domain may comprise a sequence of amino acid residues, the identity and relative positions of which correspond to those residues presented in upper case and indexed by hashes and dots in any one of the 5 sequences set out in FIG. 1B(A).

In particularly preferred embodiments, the domain may comprise a sequence of amino acid residues, the identity and relative positions of which correspond to those residues highlighted in bold upper case type in any one of the 5 sequences set out in FIG. 1B(A).

In more particularly preferred embodiments, the domain may comprise a sequence of amino acid residues, the identity and relative positions of which correspond to those residues presented in upper case type in any one of the 5 sequences set out in FIG. 1B(A).

The domain may also comprise derivative or equivalent sequences of amino acid residues which are as defined above but in which. amino acids have been added, deleted or substituted (e.g. conservatively substituted), provided that biological activity (e.g. signalling or ligand-binding activity) is substantially retained.

The domain may also comprise derivative or equivalent sequences of amino acid residues which have at least 20% identity or homology with any one of the particular amino acid sequences defined above, for example at least 30% identity or homology, for example at least 35%, 40%, 45%, 50%, 55%, 60%, 65%, 70%, 75%, 80%, 85%, 90%, 95% or 98% identity or homology therewith.

Localizing Domain, Class I

This domain may be present in secreted RP-factors, and may mediate a physical association with the surface of the target cell by acting to bind peptidoglycan or some other surface component(s). It may therefore act to increase the local concentration of the cytokine at the target cell surface, so promoting activity by increasing the local concentration of RP-factor in the immediate vicinity of the cognate receptor. Localizing domains may therefore be a characteristic feature of allosignalling bacterial cytokines, and may be absent in autosignalling factors or vice versa. For example, when present in autosignalling factors, localizing domains may act to retain the factor at or near the cell surface after secretion through the cell membrane.

When present, the localizing domain may confer important binding properties on the RP-factor, whereby binding to cognate receptor is biphasic and characterised by a primary (relatively unspecific) association with the cell surface followed by a secondary (relatively highly specific) association with the cognate receptor.

The domain may comprise a sequence of amino acid residues, the identity and relative 25 positions of which correspond to those residues indexed by asterisks in any one of the 10 sequences set out in FIG. 1C.

In preferred embodiments, the domain may comprise a sequence of amino acid residues, the identity and relative positions of which correspond to those residues indexed by 30 asterisks and dots in any one of the 10 sequences set out in FIG. 1C.

In particularly preferred embodiments, the domain may comprise a sequence of amino acid residues, the identity and relative positions of which correspond to those residues highlighted in bold upper case type in any one of the 10 sequences set out in FIG. 1 C.

In more particularly preferred embodiments, the domain may comprise a sequence of amino acid residues, the identity and relative positions of which correspond to those residues set out in any one of the 10 sequences set out in FIG. 1 C.

The domain may also comprise derivative or equivalent sequences of amino acid residues which are as defined above but in which amino acids have been added, deleted or substituted (e.g. conservatively substituted), provided that biological activity (e.g. signalling or ligand-binding activity) is substantially retained.

The domain may also comprise derivative or equivalent sequences of amino acid 15 residues which have at least 20% identity or homology with any one of the particular amino acid sequences defined above, for example at least 30% identity or homology, for example at least 35%, 40%, 45%, 50%, 55%, 60%, 65%, 70%, 75%, 80%, 85%, 90%, 95% or 98% identity or homology therewith.

Localizing Domain, Class II

This domain may be present in secreted RP-factors, and may mediate a physical association with the surface of the target cell by acting to bind the outer lipid envelope present in mycobacteria. It may therefore act to increase the local concentration of the cytokine at the target cell surface, so promoting activity by increasing the local concentration of RP-factor in the immediate vicinity of the cognate receptor. Localizing domains may therefore be a characteristic feature of allosignalling bacterial cytokines, and may be absent in autosignalling factors.

When present, the localizing domain may confer important binding properties on the RP-factor, whereby binding to cognate receptor is biphasic and characterised by a primary (relatively unspecific) association with the cell surface followed by a secondary (relatively highly specific) association with the cognate receptor.

The domain may comprise an alanine plus proline-rich segment, such as one or more of the amino acid motifs depicted in FIG. 1D as 'A' (SEQ ID NO: 59), A, B, B' (SEQ ID NO: 63), C (SEQ ID NO: 29), 'C (SEQ ID NO:55), D, D* (SEQ ID NO: 56) and D' (SEQ ID NO: 58) (any one of which may be tandemly repeated) D. Motifs A, B and D are depicted in FIG. 1D with brackets around two amino acids, to indicate that the motifs define sequences that include a choice of one or the other of the two amino acids within the brackets as follows:

```
A = appvela[av]ndl;            (SEQ ID NO: 62)

B = paplgeplpaapa[de]l;        (SEQ ID NO: 60)
and

D = appapa[de][lv].            (SEQ ID NO: 61)
```

In preferred embodiments, the domain may comprise a sequence of amino acid residues corresponding to residues 158-322 of MtubMTVO43 as shown in FIG. 1D or to that of residues 45-112 of MtubMTV008 as shown in FIG. 1A.

The domain may also comprise derivative or equivalent sequences of amino acid residues which are as defined above but in which amino acids have been added, deleted or substituted (e.g. conservatively substituted), provided that biological activity (e.g. signalling or ligand-binding activity) is substantially retained.

The domain may also comprise derivative or equivalent sequences of amino acid residues which have at least 20% identity or homology with any one of the particular amino acid sequences defined above, for example at least 30% identity or homology, for example at least 35%, 40%, 45%, 50%, 55%, 60%, 65%, 70%, 75%, 80%, 85%, 90%, 95% or 98% identity or homology therewith.

The term "isolated" is used herein to indicate that the factor exists in a physical milieu distinct from that in which it occurs in nature. For example, the isolated factor may be substantially isolated with respect to the complex cellular milieu in which it naturally occurs. The absolute level of purity is not critical, and those skilled in the art can readily determine appropriate levels of purity according to the use to which the factor is to be put.

In many circumstances, the isolated factor will form part of a composition (for example a more or less crude extract containing many other proteins and substances), buffer system or pharmaceutical excipient, which may for example contain other components (including other proteins, such as albumin).

In other circumstances, the isolated protein may be purified to essential homogeneity, for example as determined by PAGE or column chromatography (for example HPLC or mass spectrometry). In preferred embodiments, the isolated RP-factor of the invention is essentially the sole active RP-factor in a given composition. Particularly preferred are compositions in which an RP-factor (or a particular species, homologue, mutein, derivative or equivalent thereof) is present as the sole active ingredient in a pharmaceutical composition.

The RP-factor for use in the invention need not be isolated in the sense defined above, however. For example, more or less crude culture supernatants (e.g. "spent" medium) may contain sufficient concentrations of RP-factor for use in several applications. Preferably, such supernatants are fractionated and/or extracted (see below), but in many circumstances they may be used without pretreatment. They are preferably derived from spent media used to culture RP-factor-producing microorganisms (for example, the bacterial sources described infra). The supernatants are preferably sterile. They may be treated in various ways, for example by concentration, filtration, centrifugation, spray drying, dialysis and/or lyophilisation. Conveniently, the culture supernatants are simply centrifuged to remove cells/cell debris and filtered.

Such supernatants find utility in diagnostic kits and methods, for example in the diagnostic kits and methods described infra. They also find utility in the recovery from various samples of culturable microorganisms (e.g. from soil, food, marine, freshwater, or tissue samples) or from samples taken from an organism (e.g. a human or animal).

The culture supernatants may also be used as supplements in various culturing substrates, for example in culture or transport media. The culture medium may take any convenient form, such as for example agar plates, broths, slopes, coated dipsticks, coated probes, membranes, coated or filled wells or films. The medium may be a defined or complex medium, and may contain indicator dyes to facilitate identification of cultured microorganisms. Preferably, the medium is suitable for the culturing or transport of bacteria, for example *Mycobacterium* spp.

The term "isolated" as applied to the other materials of the invention (for example, the genes and other nucleic acids encoding the RP-factor and their cognate receptors/convertases) is to be interpreted mutatis mutandis. Thus, as applied to nucleic acid (e.g. RNA or DNA or (structural) genes), the isolated nucleic acid may be present in any of a wide variety of vectors and in any of a wide variety of host cells (or other milieu, such as buffers, viruses or cellular extracts).

The term "family", as applied to the proteins of the invention, is used herein to indicate a group of proteins which share substantial sequence similarities, either at the level of the primary sequence of the proteins themselves, or at the level of the DNA encoding them. The sequence similarities may extend over the entire protein/gene, or may be limited to particular regions or domains. Similarities may be based on nucleotide/amino acid sequence identity as well as similarity (for example, those skilled in the art recognise certain amino acids as similar, and identify differences based on switches of similar amino acids as conservative changes). Some members of a protein family may be related in the sense that they share a common evolutionary ancestry, and such related proteins may herein be referred to as homologues. The members of a protein family do not necessarily share the same biochemical properties or biological functions, though their similarities are usually reflected in common functional features (such as effector binding sites and substrates).

The criteria by which protein families are recognised are well-known in the art, and include computer analysis of large collections of sequences at the level of DNA and protein as well as biochemical techniques such as hybridisation analysis and enzymatic assays (see for example Pearson and Lipman (1988), PNAS USA, 85: 2444).

Thus, the RP-factors of the invention include the factors shown in FIGS. 1 A and 1B, together with their species variants, allelic forms, homologues, derivatives, muteins and corresponding secreted/nonsecreted forms (vide infra). Preferably, the RP-factors of the invention are species variants, allelic forms, homologues, derivatives, muteins and 5 corresponding secreted/nonsecreted forms of any one of the proteins represented in FIG. 1A and FIG. 1B.

The RP-factors may be synthesised in the form of a precursor which is processed to produce a mature form. Such processing may proceed via various intermediate (pro-) forms. Such precursors, intermediate forms and mature proteins are all intended to be covered by the term "RP-factor" as used herein, except where indicated otherwise. As used herein, the term "pro-RP-factor" specifically defines any of various precursors (which may or may not be active) of a mature RP-factor.

The processing may comprise proteolytic cleavage and/or secretion. The precursors may be inactive, and become active on processing as a mature form. The precursors may comprise proteins having secretory leader sequences which are removed during secretion (pre-forms). Such forms are herein referred to as "pre-RP-factor or pre-pro-RP-factors". As explained above, such pre- or prepro-forms are also intended to be covered by the 20 term "RP-factor" as used herein, except where indicated otherwise.

Processing may be attendant on the binding of an RP-factor precursor to a cognate receptor. Such receptors may then directly (or indirectly) cleave the precursor to produce a more mature form of the RP-factor. Such processing may occur as a cascade, involving several receptor-processing complexes, and so ultimately result in the production of a mature RP-factor which then acts as a signalling moiety by binding to a terminal (signal transducing) receptor.

In such processing, the proximal (or intermediate) receptors may function as convertases, and the terminal receptor as a signal transducer. However, a receptor may function as both a convertase and a signal transducer. As used herein, the term "convertase" is intended to define a molecule which binds an RP-factor precursor and (directly or indirectly) processes it to produce a more mature form. They may, for example, have protease activity.

The receptors/convertases discussed above may be disposed at the cell surface (e.g. membrane bound), cytosolic or extracellular.

Preferably, the RP-factor is derived from a bacterium (e.g. a pathogenic bacterium). Particularly preferred are RP-factors derived from high G+C Gram-positive bacteria.

The term "derived from" as applied to a defined source is intended to define not only a source in the sense of it being the physical origin for the material, but also to define material which has structural and/or functional characteristics which correspond to those of material which does originate from the reference source. Thus, a protein "derived from" a given source need not necessarily have been purified from that source.

The term "high G+C Gram-positive bacterium" is a term of art defining a particular class of evolutionarily related bacteria. The class includes *Micrococcus* spp. (e.g. *M luteus*), *Mycobacterium* spp. (for example a fast- or slow-growing mycobacterium, e.g. *M. tuberculosis, M. leprae, M. smegmatis* or *M bovis*), *Streptomyces* spp. (e.g. *S. rimosus* and *S. coelicolor*) and *Corynebacterium* spp. (e.g. *C. glutamicum*). Preferred according to the invention are RP-factors/cognate receptors/convertases derived from mycobacteria ("mycobacterial RP-factors/RP-factor receptors/convertases").

The invention also contemplates homologues, allelic forms, species variants, derivatives, muteins or equivalents of the RP-factors and RP-factor receptors/convertases of the invention.

The term "homologue" is used herein in two distinct senses. It is used sensu stricto to define the corresponding protein from a different organism (i.e. a species variant), in which case there is a direct evolutionary relationship between the protein and its homologue. This may be reflected in a structural and functional equivalence, the protein and its homologue performing the same role in each organism.

The term is also used herein sensu lato to define a protein which is structurally similar (i.e. not necessarily related and/or structurally and functionally equivalent) to a given (reference) RP-factor. In this sense, homology is recognised on the basis of purely structural criteria by the presence of amino acid sequence identities and/or conservative amino acid changes (as set out by Dayhoff et alia, *Atlas of protein structure* vol. 5, National BioMed Fd'n, Washington D.C., 1979).

For the purposes of the invention, homologues may be recognised as those proteins the corresponding DNAs of which are capable of specifically or selectively cross-hybridising, or which can cross-hybridise under selective, appropriate and/or appropriately stringent hybridisation conditions.

The term "selectively or specifically (cross)hybridisable" in this context indicates that the sequences of the corresponding ssDNAs are such that binding to a unique (or small class) of homologous sequences can be obtained under more or less stringent hybridisation conditions. This method of the invention is not dependent on any particular hybridisation conditions, which can readily be determined by the skilled worker (e.g. by routine trial and error or on the basis of thermodynamic considerations).

Preferably, the homologues, derivatives, muteins or equivalents of the RP-factor of the invention have at least 20% identity with any one of the particular amino acid sequences shown in FIG. 1A or FIG. 1B.

Particularly preferred are homologues, derivatives, muteins or equivalents of the RP-factor of the invention which have at least 30% identity, for example at least 35%, 40%, 45%, 50%, 55%, 60%, 65%, 70%, 75%, 80%, 85%, 90%, 95% or 98% identity with any one of the particular amino acid sequences shown in FIG. 1A or FIG. 1B.

The homologues, derivatives, muteins or equivalents of the RP-factor of the invention may have at least 25% homology with any one of the particular amino acid sequences shown in FIG. 1A or FIG. 1B.

Particularly preferred are homologues, derivatives, muteins or equivalents of the RP-factor of the invention which have at least 30% homology, for example at least 35%, 40%, 45%, 50%, 55%, 60%, 65%, 70%, 75%, 80%, 85%, 90%, 95% or 98% homology with any one of the particular amino acid sequences shown in FIG. 1A or FIG. 1B.

The term "derivative" as applied herein to the proteins (e.g. the RP-factors or RP-factor receptors/convertases) of the invention is used to define proteins which are modified versions of the proteins of the invention. Such derivatives may include fusion proteins, in which the proteins of the invention have been fused to one or more different proteins or peptides (for example an antibody or a protein domain conferring a biochemical activity, to act as a label, or to facilitate purification).

The derivatives may also be products of synthetic processes which use a protein of the invention as a starting material or reactant.

The term "mutein" is used herein to define proteins that are mutant forms of the proteins of the invention, i.e. proteins in which one or more amino acids have been added, deleted or substituted. The muteins of the invention therefore include fragments, truncates and fusion proteins (e.g. comprising fused immunoglobulin, receptor, convertase or enzyme moieties).

The muteins of the invention also include proteins in which mutations have been introduced which effectively promote or impair one or more activities of the protein, for example mutations which promote or impair the function of a receptor, a recognition sequence or an effector binding site.

Muteins may be produced by any convenient method. Conveniently, site-directed mutagenesis with mutagenic oligonucleotides may be employed using a double stranded template (pBluescript KS II construct containing the RP-factor or RP-factor receptor/convertase gene), (e.g. Chameleon™ or QuikChange™—Stratagene™). After verifying each mutant derivative by sequencing, the mutated gene is excised and inserted into a suitable vector so that the modified protein can be over-expressed and purified.

Preferred mutant forms are truncates consisting (or consisting essentially) of the RP-factor signalling domain or the RP-factor specificity-determining factor, or of the ligand binding domain of the RP-factor receptor, or combinations of two or more of the foregoing.

The invention also contemplates chimaeric RP-factors. These are factors which comprise one or more heterologous domains. In this context, a heterologous domain is a portion of an RP-factor which is derived from a different RP-factor to that from which the other domain(s) with which it is associated are derived. Such chimaeric RP-factors find particular utility in applications where the specificity and/or activity of the RP-factor is manipulated or altered.

Useful in the construction of such chimaeric RP-factors are DNA fragments or cassettes consisting essentially of DNA encoding selected domains (for example, the signalling domain or the specificity-determining domain), the fragment or cassette optionally being bounded by one or more restriction endonuclease cleavage sites or cloning sites. The invention also contemplates concatenated domain cassettes, as well as mutant RP-factor structural genes which have cloning sites (e.g. one or more restriction endonuclease cleavage sites) located in one or more interdomain regions.

The term equivalent as used herein and applied to the materials of the invention defines materials (e.g. proteins, DNA etc.) which exhibit substantially the same functions as those of the materials of the invention while differing in structure (e.g. nucleotide or amino acid sequence). Such equivalents may be generated for example by identifying sequences of functional importance (e.g. by identifying conserved or canonical sequences or by mutagenesis followed by functional assay), selecting an amino acid sequence on that basis and then synthesising a peptide based on the selected amino acid sequence. Such synthesis can be achieved by any of many different methods known in the art, including solid phase peptide synthesis (to generate synthetic peptides) and the assembly (and subsequent cloning) of oligonucleotides.

The homologues, fragments, muteins, equivalents or derivatives of the proteins of the invention may also be defined inter alia as those proteins which cross-react with antibodies to the proteins of the invention, and in particular which cross-react with antibodies directed against any of the specific proteins shown FIG. 1A or FIG. 1B.

The invention also contemplates all individual functional domains of the RP-factors of the invention as separate and independent entities.

The invention also contemplates recombinant RP-factor. As used herein, the term "recombinant" is intended to define material which has been produced by that body of techniques collectively known as "recombinant DNA technology" (for example, using the nucleic acid, vectors and or host cells described infra).

The invention also contemplates a pharmaceutical composition (e.g. a vaccine) comprising the RP-factor or RP-factor receptor/convertase (or homologue, species variant, allelic form, derivative, mutein or equivalent thereof) of the invention.

A pharmaceutical composition is a solid or liquid composition in a form, concentration and level of purity suitable for administration to a patient (e.g. a human or animal patient) upon which administration it can elicit the desired physiological changes. The vaccines of the invention may include any suitable adjuvant (e.g. Freund's adjuvant, BCG or BCG extracts).

In another aspect, the invention relates to a pharmaceutical composition comprising the material of the invention which is: (a) for use in therapy (e.g. immunotherapy), diagnosis or prophylaxis; and/or (b) in a pharmaceutical excipient, a unit dosage form or in a form suitable for local or systemic administration.

In another aspect, the invention relates to an antibody (or antibody derivative) specific for the RP-factor (or homologue, derivative, mutein or equivalent thereof) of the invention.

The antibody is preferably in a form suitable for use in therapy (e.g. immunotherapy), diagnosis or prophylaxis; and/or formulated in a pharmaceutical excipient, a unit dosage form or in a form suitable for local or systemic administration. The antibody may be labelled and/or immortalised and/or conjugated to another moiety, and such embodiments find particular utility in diagnostic applications.

According to another aspect of the invention there is provided an isolated or recombinant RP-factor receptor.

The receptor/convertase may be derived from any of the sources hereinbefore described, for example from a bacterial source (e.g. a pathogenic bacterial source). Such sources include high G+C Gram-positives, *Micrococcus* spp. (e.g. *M. luteus*); or *Mycobacterium* spp. (for example a fast- or slow-growing mycobacterium, e.g. *M. tuberculosis, M. leprae, M. smegmatis* or *M. bovis*); or *Streptomyces* spp. (e.g. *S. rimosus* and *S. coelicolor*); or *Corynebacterium* spp. (e.g. *C. glutamicum*).

The invention also contemplates homologues, derivatives, muteins or equivalents of the receptors/convertases of the invention, as well as recombinant RP-factor receptors/convertases (as hereinbefore defined).

The invention also contemplates a pharmaceutical composition (e.g. a vaccine) comprising the receptor/convertase (or homologue, derivative, mutein or equivalent thereof) of the invention.

Preferably, the receptor/convertase (or homologue, derivative, mutein or equivalent thereof) or pharmaceutical composition is: (a) for use in therapy (e.g. immunotherapy), diagnosis or prophylaxis; and/or (b) in a pharmaceutical excipient, a unit dosage form or in a form suitable for local or systemic administration.

Also contemplated is an antibody (or antibody derivative) specific for the receptor/convertase (or homologue, derivative, mutein or equivalent thereof) of the invention. The antibody may be: (a) for use in therapy (e.g. immunotherapy), diagnosis or prophylaxis; and/or (b) in a pharmaceutical excipient, a unit dosage form or in a form suitable for local or systemic administration.

Also contemplated is an RP-factor antagonist or inhibitor.

Preferably, the antagonist or inhibitor comprises: (a) the antibody of the invention; and/or (b) the receptor/convertase of the invention; and/or (c) an RP-factor mutein comprising an RP-factor specificity-determining domain, which for example lacks a functional signalling domain. The receptor may function as an antagonist or inhibitor if administered in soluble form, where it may act as a sink for soluble RP-factor. Preferably, modified receptors consisting of the receptor domain (and lacking the membrane anchor and wall spanning domain) are used as inhibitors or antagonists. Such derivatives may exhibit higher solubility.

The antagonist or inhibitor of the invention is preferably: (a) for use in therapy (e.g. immunotherapy), diagnosis or prophylaxis; and/or (b) in a pharmaceutical excipient, a unit dosage form or in a form suitable for local or systemic administration.

Also contemplated by the invention is an RP-factor agonist, activator or mimetic. Preferably, the agonist, activator or mimetic comprises: (a) the RP-factor receptor/convertase antibody as herein described; and/or (b) an RP-factor mutein comprising (or consisting of) an RP-factor specificity-determining domain; and/or (c) an RP-factor mutein comprising (or consisting of) an RP-factor signalling domain; and/or (d) operably coupled combinations of any of (a)-(c).

The agonist, activator or mimetic may be: (a) for use in therapy (e.g. immunotherapy), diagnosis or prophylaxis; and/or (b) formulated in a pharmaceutical excipient, a unit dosage form, in a form suitable for local or systemic administration or in admixture with an antibiotic.

Preferably, the agonist, activator or mimetic may be for use in adjunctive therapy (for example formulated or presented in combination with an antimicrobial agent, e.g. an antibiotic).

The invention also contemplates isolated nucleic acid encoding the RP-factor (or homologue, derivative, allelic form, species variant, mutein or equivalent thereof) or RP-factor receptor/convertase (or homologue, derivative, allelic form, species variant, mutein or equivalent thereof) of the invention. The nucleic acids of the invention therefore embrace DNA having any sequence so long as it encodes the proteins of the invention. It will be appreciated by those skilled in the art that as a result of degeneracy in the genetic code, any particular amino acid sequence of the invention may be encoded by many different sequences. Thus, the nucleic acid sequence may be selected or optimised, e.g. with respect to the codon usage in any particular host cell.

The invention also contemplates vectors (e.g. an expression vector) comprising the nucleic acid of the invention. The nature of the vector is not critical to the invention. Any suitable vector may be used, including plasmid, virus, bacteriophage, transposon, minichromosome, liposome or mechanical carrier.

The expression vectors of the invention are DNA constructs suitable for expressing DNA which encodes the desired protein product (e.g. RP-factor or RP-factor receptor) which may include: (a) a regulatory element (e.g. a promoter, operator, activator, repressor and/or enhancer), (b) a structural or coding sequence which is transcribed into mRNA and (c) appropriate transcription, translation, initiation and termination sequences. They may also contain sequence encoding any of various tags (e.g. to facilitate subsequent purification of the expressed protein, such as affinity (e.g. His) tags).

Particularly preferred are vectors which comprise an expression element or elements operably linked to the DNA of the invention to provide for expression thereof at suitable levels. Any of a wide variety of expression elements may be used, and the expression element or elements may for example be selected from promoters, enhancers, ribosome binding sites, operators and activating sequences. Such expression elements may comprise an enhancer, and for example may be regulatable, for example being inducible (via the addition of an inducer).

As used herein, the term "operably linked" refers to a condition in which portions of a linear DNA sequence are capable of influencing the activity of other portions of the same linear DNA sequence. For example, DNA for a signal peptide (secretory leader) is operably linked to DNA for a polypeptide if it is expressed as a precursor which participates in the secretion of the polypeptide; a promoter is operably linked to a coding sequence if it controls the transcription of the sequence; a ribosome binding site is operably linked to a coding sequence if it is positioned so as to permit translation.

The vector may further comprise a positive selectable marker and/or a negative selectable marker. The use of a positive selectable marker facilitates the selection and/or identification of cells containing the vector.

Also contemplated by the invention are host cells comprising the vector of the invention. Any suitable host cell may be used, including prokaryotic host cells (such as *Escherichia coli, Streptomyces* spp. and *Bacillus subtilis*) and eukaryotic host cells.

In another aspect, the invention provides a culture or transport medium comprising the RP-factor (or homologue, derivative, mutein or equivalent thereof) of the invention. The culture medium may take any convenient form, such as for example agar plates, broths, slopes, coated dipsticks, coated probes, membranes, coated or filled wells or films. The medium may be a defined or complex medium, and may contain indicator dyes to facilitate identification of cultured microorganisms. Preferably, the medium is suitable for the culturing or transport of bacteria, for example *Mycobacterium* spp. *Streptomyces* spp. and *Corynebacterium* spp.

The invention also contemplates a nucleic acid probe comprising nucleic acid complementary to the nucleic acids of the invention. Such probes are preferably selectively hybridisable with nucleic acid encoding the proteins (e.g. the RP-factors of RP-factor receptors/convertases) of the invention. They are conveniently single stranded DNA or RNA probes.

The invention also contemplates a diagnostic kit comprising the factor (or homologue, derivative, mutein or equivalent thereof), receptor, antibody, probe or culture medium of the invention.

In another aspect, the invention contemplates antisense DNA corresponding to the nucleic acid encoding the RP-factor or RP-factor receptor/convertase of the invention.

The invention also contemplates a process for producing an antimicrobial drug comprising the steps of: (a) providing an RP-factor receptor; (b) providing candidate drugs; (c) screening the candidate drugs by contacting the RP-factor receptor/convertase with one of the candidate drugs and determining the affinity of the candidate drug for the RP-factor receptor, wherein the affinity is an index of antimicrobial activity, and optionally (d) synthesising or purifying a drug having antimicrobial activity on the basis of the identity of the candidate drug screened in step (c).

Preferably, the process for producing an antimicrobial drug comprises the steps of: (a) providing an RP-factor receptor/convertase; (b) providing a candidate drug; (c) providing an RP-factor; (d) screening the candidate drugs by contacting the RP-factor receptor/convertase with one of the candidate drugs in the presence of the RP-factor, and then determining the ability of the candidate drug to compete non-productively with the RP-factor for binding to the RP-factor receptor, wherein the competitive binding ability is an index of antimicrobial activity, and optionally (e) synthesising or purifying a drug having antimicrobial activity on the basis of the identity of the candidate drug screened in step (d).

The invention also covers an antimicrobial drug produced by (or obtainable by) the processes of the invention, and also derivatives thereof.

Also contemplated by the invention is a method for determining the microbiological quality of a product (e.g. a foodstuff, pharmaceutical preparation or medical product) comprising the step of contacting a sample of the product with an RP-factor (for example, an RP-factor as hereinbefore defined). In such methods, the RP-factor preferably forms part of a nutrient composition (e.g. a plate, broth, film or dipstick).

In another aspect, the invention relates to a method of culturing bacterial (e.g. mycobacterial) cells, comprising the step of incubating the cells in a culture medium containing an RP-factor (for example, an RP-factor as hereinbefore defined).

Also contemplated by the invention is an ex vivo method of diagnosis, comprising the step of contacting a biological sample with an RP-factor (for example, an RP-factor as hereinbefore defined).

The diagnostic method of the invention preferably includes the step of incubating the culture or transport medium of the invention to permit growth of cells in the biological sample (e.g. bacterial cells).

Also contemplated by the invention is a method of: (a) stimulating the growth of a microorganism; and/or (b) resuscitating a dormant, moribund or latent microorganism; comprising the step of contacting the microorganism with an RP-factor (for example, an RP-factor as hereinbefore defined).

The invention also contemplates a process for producing the recombinant RP-factor or RP-factor receptor/convertase of the invention comprising the steps of: (a) culturing the host cell of the invention, and (b) purifying the factor or receptor/convertase from the cultured host cells (e.g. from a culture supernatant or cell fraction).

Also contemplated by the invention is a process for producing the recombinant RP-factor or receptor/convertase of the invention comprising the steps of: (a) probing a gene library with a nucleic acid probe which is selectively hybridisable with the cognate structural gene to produce a signal which identifies a gene that selectively hybridises to the probe; (b) expressing the gene identified in step (a) (for example by cloning into a host cell, e.g. according to the process as hereinbefore defined) to produce the factor or receptor.

Also covered is a recombinant RP-factor or receptor/convertase obtainable by the above-described process.

Medical Applications

The invention permits the isolation, synthesis and rational design of a wide range of novel medicaments and pharmaceuticals for use in therapy, prophylaxis and diagnosis.

The various forms of therapy, prophylaxis and diagnosis in which the materials of the invention find application may involve changing, breaking or perturbing the resuscitation (RP-factor) signal transduction pathway of one or more infecting pathogens.

Thus, the materials of the invention find general application as antimicrobial agents, for example as antibacterial agents. They may therefore be used in the treatment, prophylaxis or diagnosis of microbial (e.g. bacterial) infections, particularly those infections associated with latency (e.g. mycobacterial infections).

Thus, the invention may for example be used to prevent, reduce or interfere with: (a) the resuscitation of a latent (or dormant) pathogen, and/or (b) the growth of a pathogen, and/or (c) the multiplication and spread of a pathogen; and/or (d) the activation of a latent infection (for example a latent bacterial (e.g. mycobacterial) infection).

In general, the materials of the invention may be used to treat conditions in which changing, breaking or perturbing the resuscitation (RP-factor) signal transduction pathway or blockading the RP-factor receptor/convertase associated with an infecting pathogen is indicated.

Particularly useful materials for use in such therapies/prophylactic methods include RP-factor antagonists or inhibitors. Such antagonists or inhibitors may comprise antibodies to the RP-factor or to the RP-factor receptor/convertase as herein defined; the RP-factor receptor/convertase of the invention; an RP-factor mutein, e.g. which comprises an altered RP-factor specificity-determining domain and/or which lacks a functional signalling domain.

RP-factor antibodies act to sequester and ultimately eliminate endogenous RP-factors in a patient bearing a latent microbial infection.

RP-factor receptor antibodies bind non-productively to the receptors associated with the infecting pathogen. Antibodies to the convertase inactivate (e.g. by steric inhibition) the convertase activity and so prevent maturation of the RP-factor. The antibodies may therefore competitively inhibit the binding of endogenous RP-factor to the receptors/convertases associated with the infecting pathogen. Alternatively, they may bind with high affinity (and/or essentially irreversibly) to the RP-factor receptors/convertases and so block RP-factor-ligand binding or RP-factor maturation. A similar activity is displayed by the RP-factor muteins having altered specificity and/or signalling activity.

In either case, the RP-factor-RP-receptor/convertase binding required for resuscitation of latent pathogens, growth of the pathogen and/or progression of the disease state is perturbed, reduced or abolished.

RP-factor receptors for use as therapeutics in such methods are uncoupled from the signal transduction pathway with which they are normally associated. Thus, they are preferably free (i.e. in soluble or dispersible) form and/or not membrane bound. In this way, effective circulating or systemic concentrations of the free RP-factor receptor can be established and maintained in a patient. In this form, the RP-factor receptors act as RP-factor sinks, and titrate out (and preferably ultimately eliminate) endogenous RP-factors in a patient bearing a latent microbial infection. The receptors therefore reduce or prevent activation of the (latent) pathogen and/or stimulation of pathogen growth, so slowing or halting the progression of the infection.

In another aspect, the invention may be used to resuscitate or assist in resuscitating (or activate or assist in activating) a latent (dormant) pathogenic microbe in vivo thereby to potentiate adjunctive antimicrobial therapy. The adjunctive antimicrobial therapies for use in such applications are those which depend for full efficacy on a non-latent or active (e.g. growing or replicating) target pathogen population (for example adjunctive therapies based on certain types of antibiotic). Thus, the materials of the invention may act synergistically with various antimicrobial compounds in antimicrobial therapy.

In a preferred embodiment, the invention is used to potentiate the antimicrobial therapy of tuberculosis, for example involving co-administration of one or more of isoniazid, rifampicin, pyrzinamide and/or ethambutol (or streptomycin).

Particularly useful materials for use in such therapies include for example the RP-factors of the invention, RP-factor agonists, activators and mimetics. Such agonists, activators or mimetics may comprise: the RP-factor receptor antibodies as hereinbefore described; the RP-factor convertase as hereinbefore defined; an RP-factor mutein comprising (or consisting of) an RP-factor specificity-determining domain; an RP-factor mutein comprising (or consisting of) an RP-factor signalling domain; and/or operably coupled combinations thereof.

The RP-factor receptor antibodies for use in such methods are those which serve to trigger an efferent signal transduction pathway at the RP-factor receptor. They may therefore act as RP-factor mimetics, breaking latency/dormancy and acting to resuscitate the pathogen.

Particularly useful in such methods are mutant RP-factors having altered specificity (e.g. in which the specificity-determining domain has been mutated or modified). Such mutant RP-factors may be active against a broad range of pathogens (e.g. against substantially all pathogenic or infective mycobacteria) or targeted against specific pathogens (for example, *M. tuberculosis* and *M. leprae*).

The antibodies, RP-factors, receptors and convertases discussed above may be administered directly or via a live vaccine vehicle. Such live vaccines vehicles comprise microorganisms which have been genetically engineered to express (and preferably secrete) the therapeutically active antibodies, RP-factors, receptors and convertases of the invention in vivo.

The invention therefore finds application in the treatment of a wide variety of microbial infections, and finds particular application in the treatment of latent microbial (e.g. bacterial) infections.

In preferred embodiments, the invention finds application in the treatment of actinomycete or mycobacterial infections, for example those involving *M. tuberculosis, M. leprae, M. bovis, M. kansasii* and *M. avium*.

Other infections which may be treated according to the invention include those involving *Corynebacterium* spp. (including *Corynebacterium diphtheriae*), *Tropheryma whippelii, Nocardia* spp. (including *Nocardia asteroides* and *Nocardia brasiliensis*), *Streptomyces* spp. (including *Streptomyces griseus, Streptomyces paraguayensis* and *Streptomyces somaliensis*), *Actinomadura* spp., *Nocardiopsis* spp., *Rhodococcus* spp., *Gordona* spp., *Tsukamurella* spp. and *Oerskovia* spp. as well as other pathogenic organisms from the group referred to as high G+C Gram-positive bacteria. Other infections which may be treated include those involving pathogenic low G+C Gram-positive bacteria (e.g. *Streptococcus* spp., *Staphylococcus* spp., *Listeria* spp., *Bacillus* spp., *Clostridium* spp. and *Lactobacillus* spp.).

The invention may also be embodied in various vaccines or immunotherapeutic agents.

Such vaccines or agents target one or more elements of the RP-factor mediated signal transduction pathway described herein (and in particular, the RP-factor or RP-factor receptors/convertases themselves). Thus, the RP-factors may be administered as part of a vaccine or immunotherapeutic composition to elicit an immune response directed against endogenous RP-factor in the patient, so reducing, preventing activation of the pathogen and so slowing or halting the progression of the infection.

Alternatively (or in addition), the RP-factor receptors/convertases may be administered as part of a vaccine or immunotherapeutic composition to elicit an immune response directed against receptors for pathogen-borne RP-factor in the patient. In this way, cellular and/or humoral immune responses may be stimulated against the pathogen(s) and/or activation of a latent pathogen (or its continued growth or multiplication) via the RP-factor signal transduction pathway may be reduced or prevented, so slowing or halting the progression of the infection.

The invention also finds application in the preparation of live vaccines: attenuated microbial strains can be constructed in which the gene(s) encoding (or regulating the expression or activity of) one or more RP-factors are mutated. Such attenuated vaccines may be based on mutant strains of actinomycetes, mycobacteria (for example *M. tuberculosis, M. leprae, M. bovis* (such as *M. bovis* BCG), *M. kanasii* and *M. avium*), *Corynebacterium* spp. (including *Corynebacterium diphtheriae*), *Tropheryma whippelii, Nocardia* spp. (including *Nocardia asteroides* and *Nocardia brasiliensis*), *Streptomyces* spp. (including *Streptomyces griseus, Streptomyces paraguayensis* and *Streptomyces somaliensis*), *Actinomadura* spp., *Nocardiopsis* spp., *Rhodococcus* spp., *Gordona* spp., *Tsukamurella* spp. and *Oerskovia* spp. as well as other pathogenic organisms from the group referred to as high G+C Gram-positive bacteria.

Particularly useful in such attenuated vaccines are strains bearing mutated RP-factor-encoding genes. Such mutations may be frameshift, deletion, insertion and/or substitution mutations. In preferred embodiments the mutations are null mutations (e.g. non-reverting null mutations), and may prevent growth of the microbe (i.e. "attenuate" it). In other embodiments the mutations may result in the expression of mutant RP-factors having altered specificity (e.g. in which the specificity-determining domain has been mutated or modified) and/or which lack a functional signalling domain. Such mutant RP-factors may bind with high affinity (and/or essentially irreversibly) and non-productively to the RP-factor receptors/convertases and so block RP-factor-ligand binding or RP-factor maturation. The attenuated microbial strains of the invention may also bear mutations in other genes (for example, in other genes essential to growth), and may also bear one or more genetic marker elements.

Biotechnological Applications

It is widely recognised that the great majority (probably well in excess of 99%) of soil organisms have not yet been cultured. Hitherto uncultured organisms are also expected to exist in other sources. The present invention may be used to permit the recovery of such organisms by culture from any source. Thus, the invention provides a way of unlocking an immense reservoir of biodiversity that is known to exist, but is presently inaccessible.

Thus, the present invention provides an unprecedented resource from which libraries of potentially useful microorganisms and biomolecules can be generated. Such libraries can then be used in screening methods to search for medically or industrially useful products.

Thus, in another aspect the invention provides a process for producing a library of biomolecules comprising the steps of: (a) providing a sample (e.g. a soil, marine, food, freshwater, tissue or organism-derived); (b) incubating the sample in a culture medium comprising an RP-factor (for example, an RP-factor as defined in the preceding claims or a culture supernatant comprising an RP-factor) to produce a microbial culture; and (c) isolating microorganisms from the culture of step (b).

The process may further comprise the step of screening the isolated microorganisms for those which elaborate one or more biomolecules of interest (for example a metabolite, enzyme, antibiotic (e.g. antiviral, antibacterial or antifungal agent) or toxin).

Also contemplated is a biomolecule produced by (or obtainable by) the above process, or a derivative thereof.

In another aspect, the invention provides a process for producing a library of microorganisms (e.g. bacteria) comprising the steps of: (a) providing a sample (e.g. a soil, marine, food, freshwater, tissue or organism-derived sample); (b) incubating the sample in a culture medium comprising an RP-factor (for example, an RP-factor as defined in the preceding claims or a culture supernatant comprising an RP-factor) to produce a microbial culture; (c) isolating microorganisms from the culture of step (b).

Also contemplated is a microbe produced by (or obtainable by) the above process, or a 30 derivative (e.g. mutant) thereof.

EXEMPLIFICATION

The invention will now be described in more detail with reference to several Examples. These are for exemplary purposes only and are not intended to limit the invention in any way.

BRIEF DESCRIPTION OF THE DRAWINGS

FIGS. 1A-1E: Part A. Multiple sequence alignment of the predicted amino-acid sequences of RP-factor-like gene products from *M. luteus, M. tuberculosis, M. leprae* and *Streptomyces coelicolor*. Proteins similar to the RP-factor are derived from *M. tuberculosis* (accession nos. U38939, nt 2406-2765, and Z81368, nt 33932-34396) and *M. leprae* (accession nos. L01095, nt 12292-12759, and L04666, nt 25446-24921). The DNA sequences of interest in accession Z81 368 are also encompassed by accession AD000010. N-terminal residues corresponding to predicted Gram-positive signal sequences are underlined. The *M. leprae* L04666 sequence may also contain a short, 32 aa signal peptide.

Figures 3A, 3B:
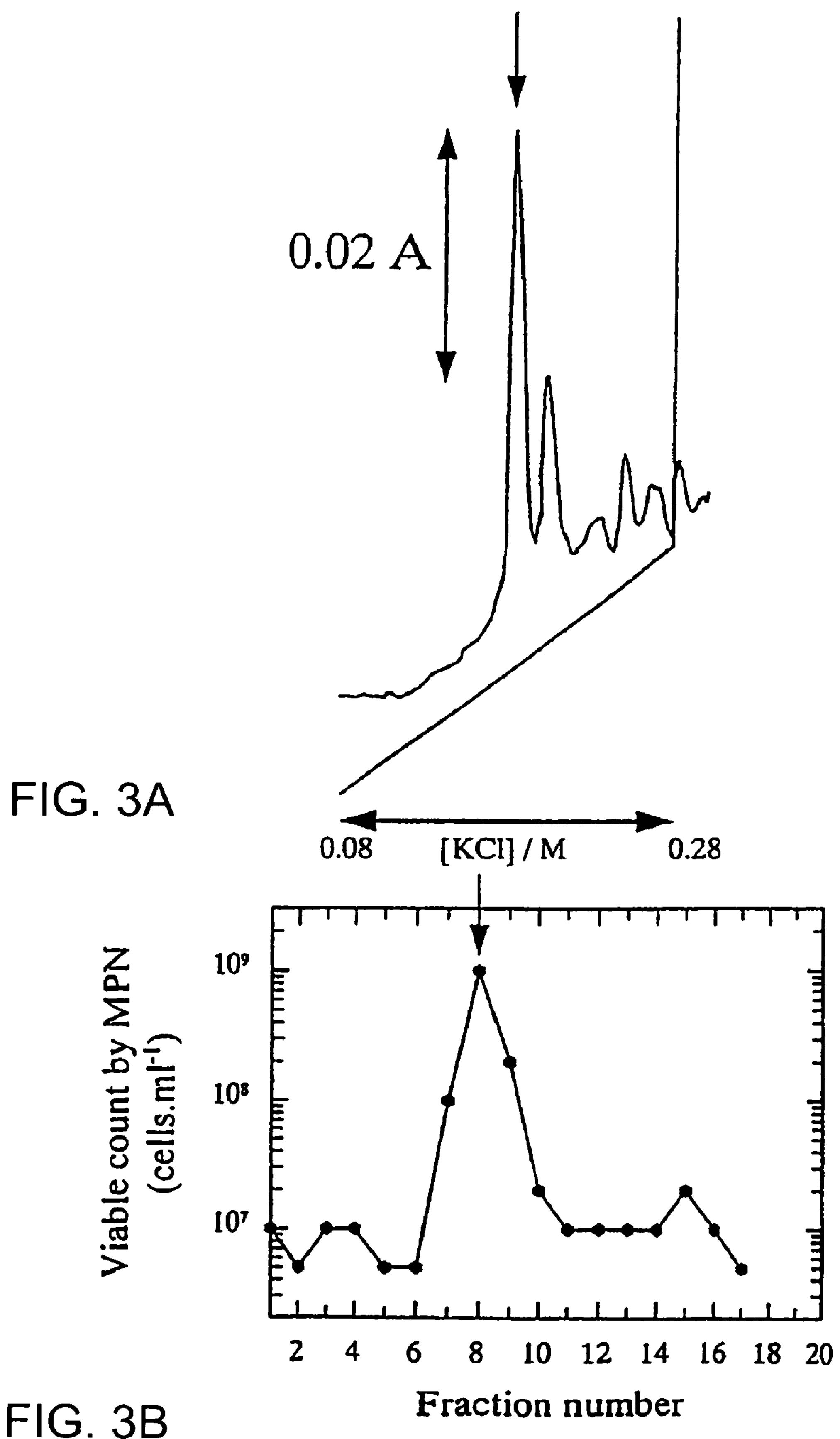

Part B. Multiple sequence alignment of gene products related to YabE of *Bacillus subtilis*. The alignment is given in two parts (A and B), with aligned residues in upper case. Those residues which are conserved (or conservatively substituted) in two or more sequences are in bold. In Part A, perfectly conserved residues are marked with a hash (#) and conservative substitutions with a dot (.). Cperfring is an incomplete ORF 1 from *Clostridium perfringens* (Acc. No. U04966); Caceto506 is an incomplete ORF from contig 506, *Clostridium acetobutylicum* genome sequencing project. YocH from *B. subtilis* and YabE from *B. subtilis* are YocH and YabE predicted gene products from the *B. subtilis* genome sequencing project (Acc. Nos. BG13521 and P37456).

Part C. Alignment of the RP-factor C-terminal domain with known and hypothetical wall-associated proteins from other organisms. Perfectly conserved residues are marked with an asterisk, those conserved in at least 7 sequences are marked with a dot (.).

Part D. Motifs in the C-terminus (residues 158-322) of MtubMTVO43.

Part E. Alignment between the predicted amino acid sequence of the *M. luteus* RP-factor and p60 proteins from *Listeria* spp. Many of the residues that are conserved in the alignment between the C-terminal portion of the *M. luteus* RP-factor (residues 125-220) and the *L. monocytogenes* EGD p60 protein (residues 158-245), are also conserved in the p60 protein from six other *Listeria* spp.

FIGS. 2A- and 2B: Part A. The sequence of the RP-factor-encoding gene and its predicted product. The nucleotide sequence is in lower case with PCR primers in bold. The predicted protein sequence is in upper case bold (single letter code). Protein and peptide microsequence data used for oligonucleotide design are in upper case italics.

Part B. The sequence of a 299 base pair DNA fragment encoding part of an RP-factor from *Streptomyces coelicolor*. The deduced amino acid sequence is given below the DNA sequence using the single letter amino acid code.

FIGS. 3A-3D: The elution profile of the resuscitation activity. Fractions eluted from the DEAE Sepharose™ column (see Materials and Methods) with 0.25 M KCl were applied to a Mono Q® column which was developed with a 20 ml linear gradient from 0.08 to 0.28 M KCl in 10 mM Tris-Cl buffer supplemented by 10% glycerol, pH 7.4. 10 ml of a diluted suspension of starved cells (CFU $3\cdot10^6$ cells$\cdot$ml$^{-1}$, total count $1.2\cdot10^9$ cells$\cdot$ml$^{-1}$) were added to 200 ml of LMM supplemented with 0.5% w/v lactate and 0.05% yeast extract containing of 2 μl of each fraction in 5-10 replicates in the Bioscreen instrument. For details see Materials and Methods. A: absorbance at 280 nm and magnitude of KCl concentration. B: resuscitation activity. C: SDS-PAGE profile of the fractions following DEAE-cellulose and Mono Q® chromatography. Lanes 1, markers (94,000, 67,000, 43,000, 30,000, 20, 100, 14,400); 2, fraction from DEAE-cellulose column; 3, purified preparation (fraction number 8 from the Mono Q®-column). D: Reduction of apparent lag phase of viable cells. 10 μl of a diluted suspension of viable, stationary phase cells (viable count 20 cells) was added to 200 ml of LMM supplemented with 0.5% w/v L-lactate and containing 2 μl of each fraction (from a different experiment to that shown in parts A and B) in 5-10 replicates in the Bioscreen instrument.

The apparent lag phase was estimated by extrapolating the exponential growth line to the abscissa.

Figure 4A:
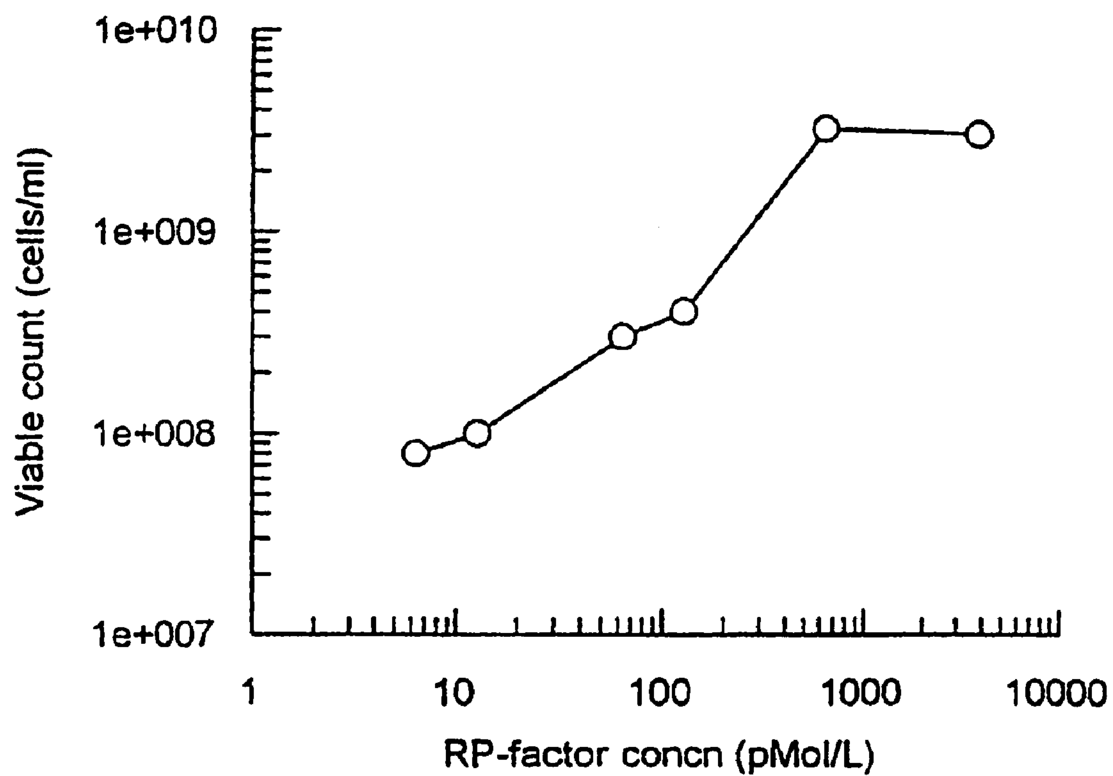
Figure 4B:
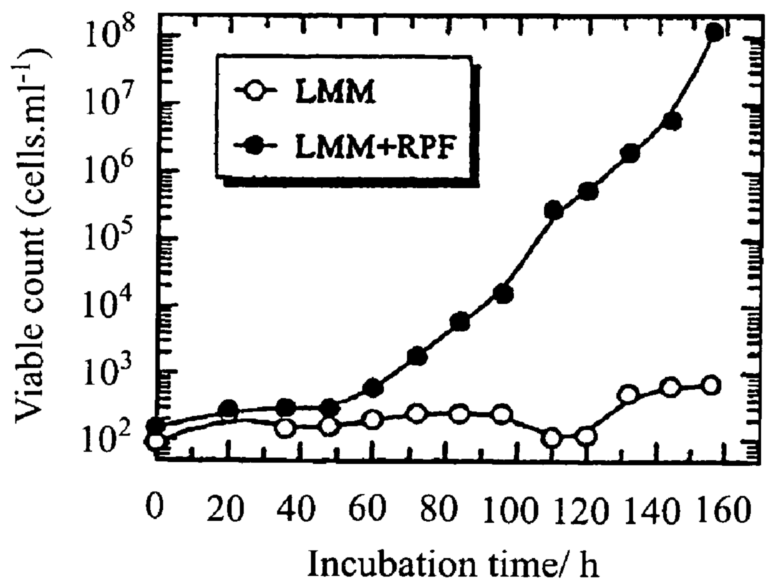

FIGS. 4A-4B: Effect of purified RP-factor on *M. luteus*.

A. Concentration dependence of RP-factor activity for resuscitation: resuscitation of dormant cells with different concentrations of RP-factor. 10 μl of a diluted suspension of starved cells (CFU $3\cdot10^{6}$ cells·ml$^{-1}$, total count $5\cdot10^{9}$ cells·ml$^{-1}$) was added to 200 μl of LMM supplemented with 0.5% w/v L-lactate, 0.05% yeast extract and RP-factor in concentrations shown in 5-10 replicates in the Bioscreen instrument. For details see Materials and Methods.

B. Growth of washed cells. Stationary phase cells of *M. luteus* grown in LMM were washed five times by suspension and centrifugation in LMM from which lactate had been omitted. Bacteria were finally suspended in the same medium by repeatedly passing them through a syringe, diluted and inoculated into a 20 ml flask containing LMM or LMM plus 31 pM RP-factor. The initial cell density was 250 viable cells per ml and incubation was at 30° C. with intensive shaking. Growth was monitored by plating 0.1 ml samples on plates containing broth E solidified with agar.

Figure 5C:
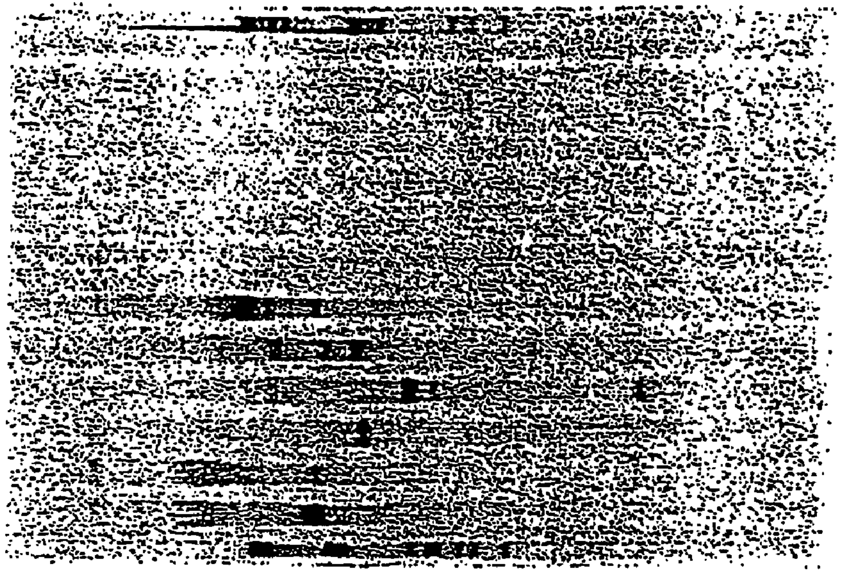
Figure 5B:
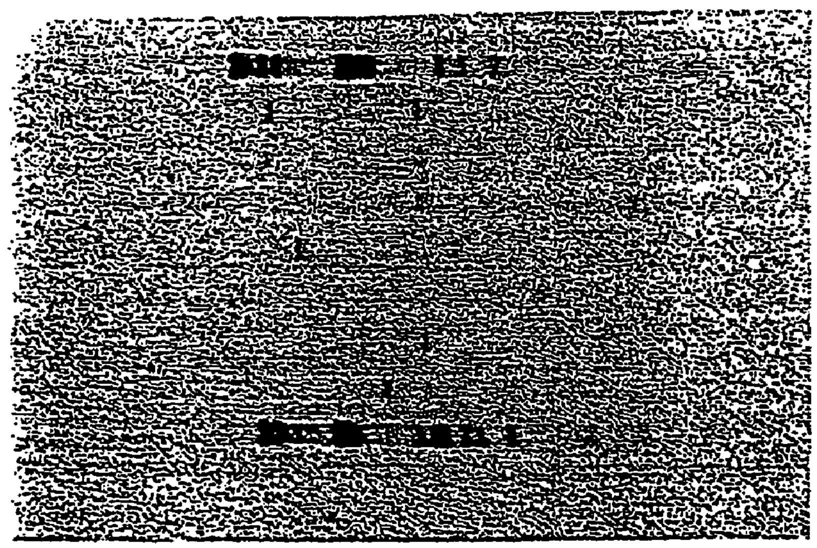
Figure 5A:
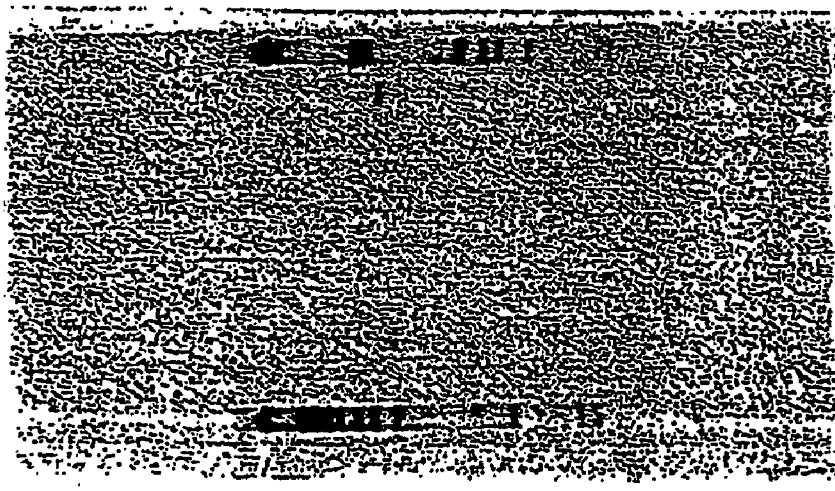

FIGS. 5A-5C: Detection of RP-factor-like genes in *Micrococcus luteus, Mycobacterium smegmatis* and *Streptomyces rimosus*.

| Part A | Part B | | |
|---|---|---|---|
| *M. luteus* | *M. luteus* | | Part C |
| Lane 1 | λBstEII | λPstI | λPstI |
| Lane 2 | ClaI | XhoI | *S. rimosus* XhoI |
| Lane 3 | SalI | StuI | *S. rimosus* StuI |
| Lane 4 | SacII | SmaI | *S. rimosus* SmaI |
| Lane 5 | PstI | PvuII | *S. rimosus* PvuII |
| Lane 6 | NcoI | PstI | *S. rimosus* PstI |
| Lane 7 | NheI | KpnI | *S. rimosus* BamHI |
| Lane 8 | MluI | BamHI | *M smegmatis* XhoI |
| Lane 9 | AatII | λPvuII | *M smegmatis* StuI |
| Lane 10 | λPstI | | *M smegmatis* SmaI |
| Lane 11 | | | *M smegmatis* PvuII |
| Lane 12 | | | *M smegmatis* PstI |
| Lane 13 | | | *M smegmatis* BamHI |
| Lane 14 | | | λPvuII |

Figure 6A:
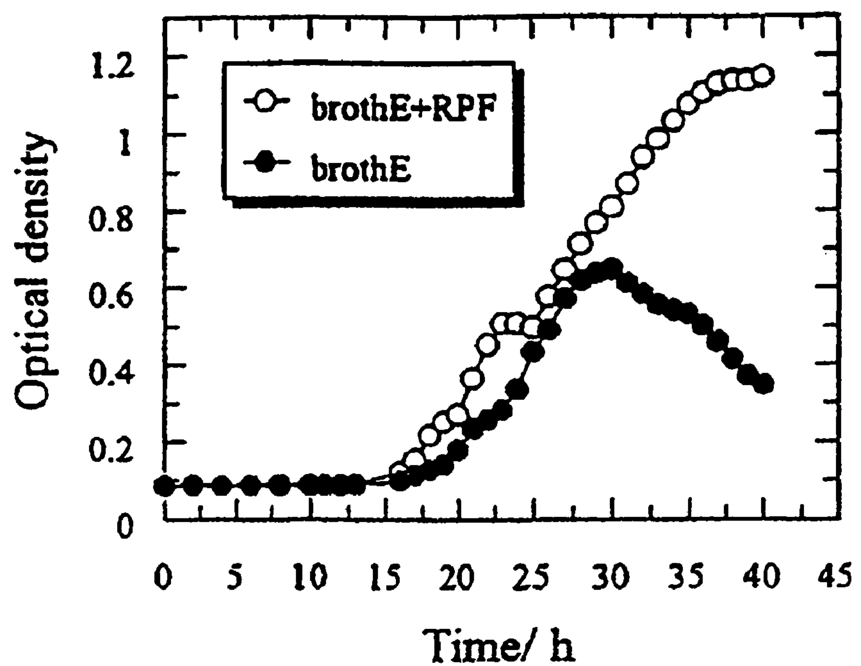

FIGS. 6A and B Effect of *M. luteus* RP-factor on the growth of *Mycobacterium smegmatis* (A) and *Mycobacterium bovis* (B) in batch culture as observed turbidimetrically. *M. smegmatis* was grown in broth E, to which was added RP-factor at 31 pMol/L. Cells were inoculated at a level of circa 200 per well, and growth was monitored in the Bioscreen instrument. *M. bovis* was grown in Sauton medium, as described in the Materials and Methods section, to which RP-factor (620 pMol/L) was either added or not. The inoculum was circa $1\cdot10^{5}$ cells·ml$^{-1}$, and the OD shown is the average of 10 separate determinations of 10 separate tubes.

Figure 7A:
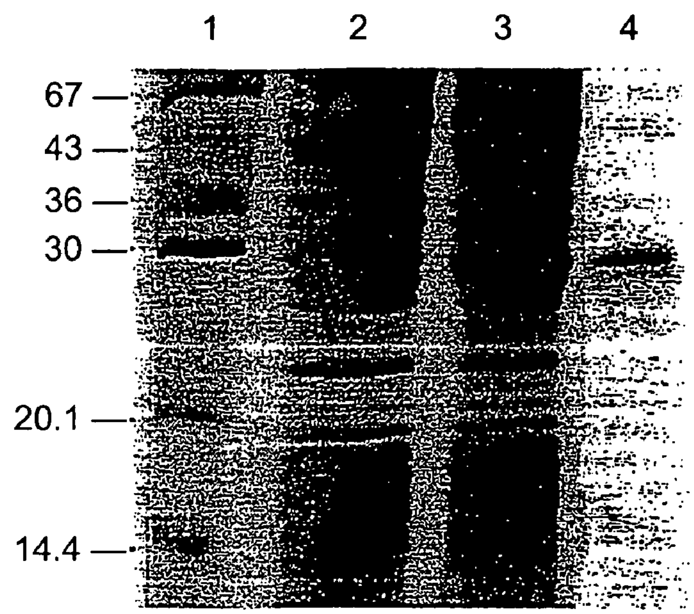
Figure 7B:
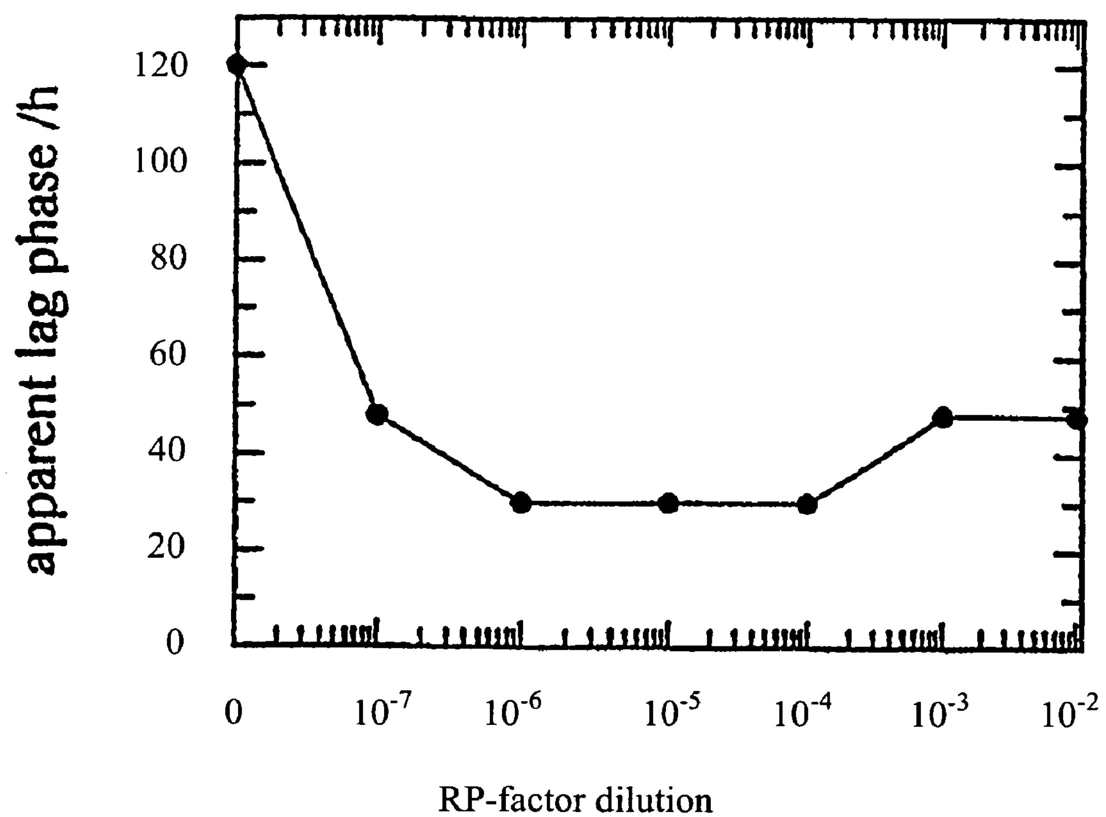
Figure 7C:
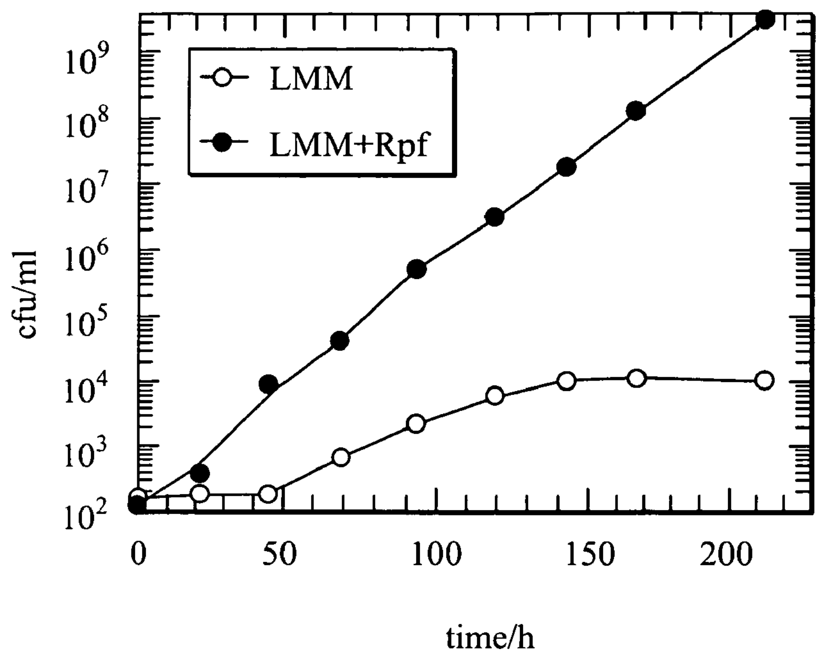

FIGS. 7A-7C: A: Purification of His-tagged RP-factor. RP-factor was expressed in *E. coli* HSM174(DE3) and purified as described infra. Shown is the SDS-PAGE profile of fractions following $Ni^{2+}$-chelation chromatography. The molecular weight (kDal) markers (SIGMA) were bovine serum albumin (67), ovalbumin (43), glyceraldehyde 3-phosphate dehydrogenase (36), carbonic anhydrase (30), soya bean trypsin inhibitor (20.1), and lactalbumin (14.4). Lane: 1, markers; 2, crude extract from *E. coli* containing pET19b vector; 3, crude extract from *E. coli* containing pRPF1; 4, purified recombinant RP-factor.

B: Reduction of the apparent lag phase of viable cells of *M. luteus* by purified 5 recombinant RP-factor. For experimental details see the legend for FIG. 3C. A dilution factor of $10^{0}$ corresponds to 33 ig RP-factor/ml.

C: Stimulation of the growth of washed cells of *M. luteus* by purified recombinant RP-factor. Stationary phase cells of *M. luteus* grown in LMM were washed 5 times by suspension and centrifugation in LMM from which lactate had been omitted. Bacteria were finally suspended in the same medium by repeatedly passing them through a syringe, diluted, and inoculated into a 20 ml flask with LMM or LMM in the presence of RP-factor (230 pMol/L). The initial cell density was ca. $10^{2}$ viable cells per ml and incubation was at 30° C. with intensive shaking. Growth was monitored by plating 0.1 ml samples on plates containing nutrient broth E solidified with agar.

Figure 8A:
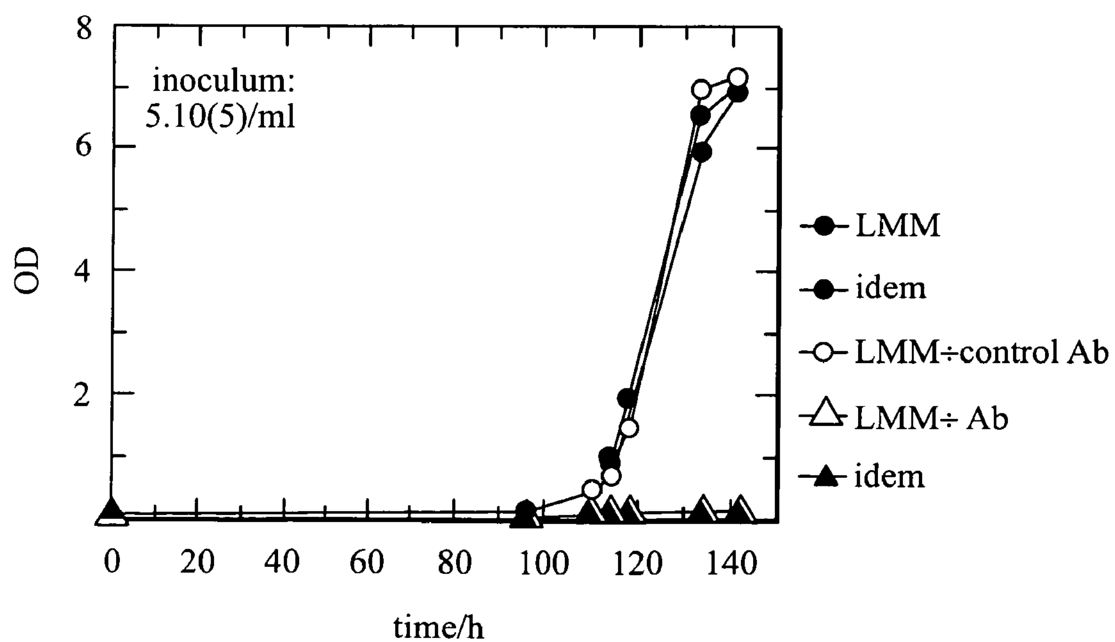
Figure 8B:
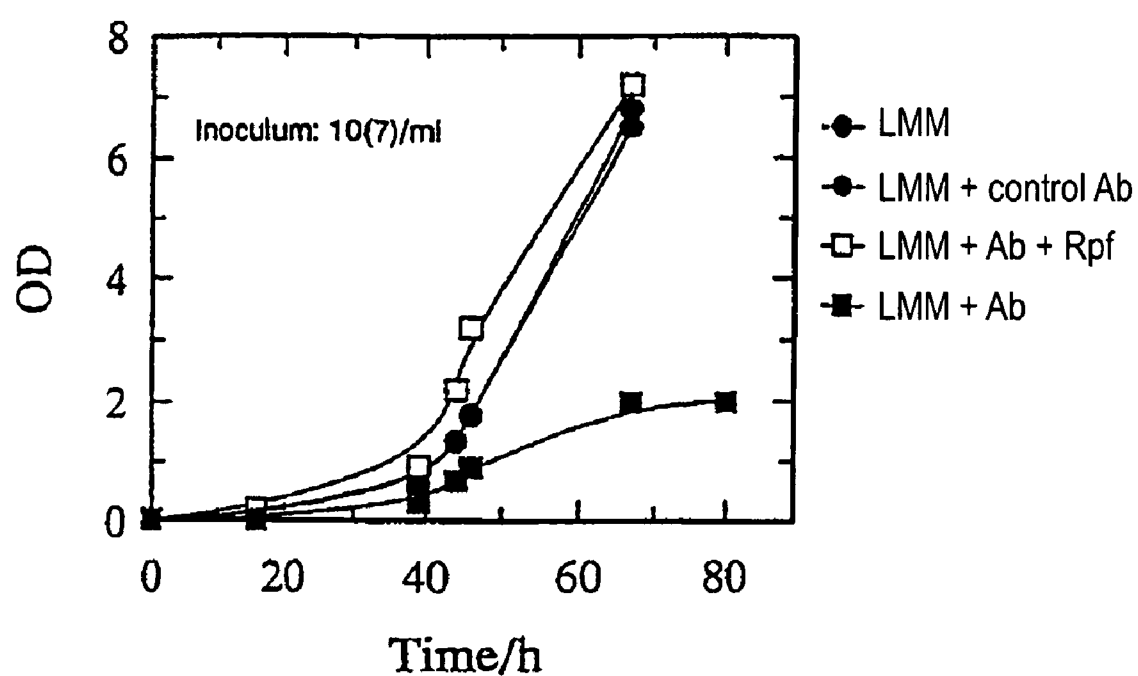

FIGS. 8A and 8B: A: Anti-RP-factor serum inhibits the growth of *Micrococcus luteus*. Bacteria were inoculated at an initial density of $5\times10^{5}$ per ml into lactate minimal medium (LMM) and the $OD_{600nm}$ was monitored at intervals. Growth of the cultures was monitored over 140 hours at intervals. The samples labelled LMM+Ab and LMM+control Ab contain equivalent amounts of immune and pre-immune serum, respectively. Immune serum (Ab) and pre-immune serum (control Ab) were employed at a 1:1000 dilution.

B: RP-factor overcomes the inhibitory effect of anti-RP-factor serum on growth of *Micrococcus luteus*. Bacteria were inoculated at an initial density of $10^{7}$ cells per ml and growth was monitored by measuring the $OD_{600nm}$ at intervals. Immune serum (Ab) and pre-immune serum (control Ab) were employed at a 1:1000 dilution and RP-factor was added at a final concentration of 50 ng/ml.

Figure 9A:
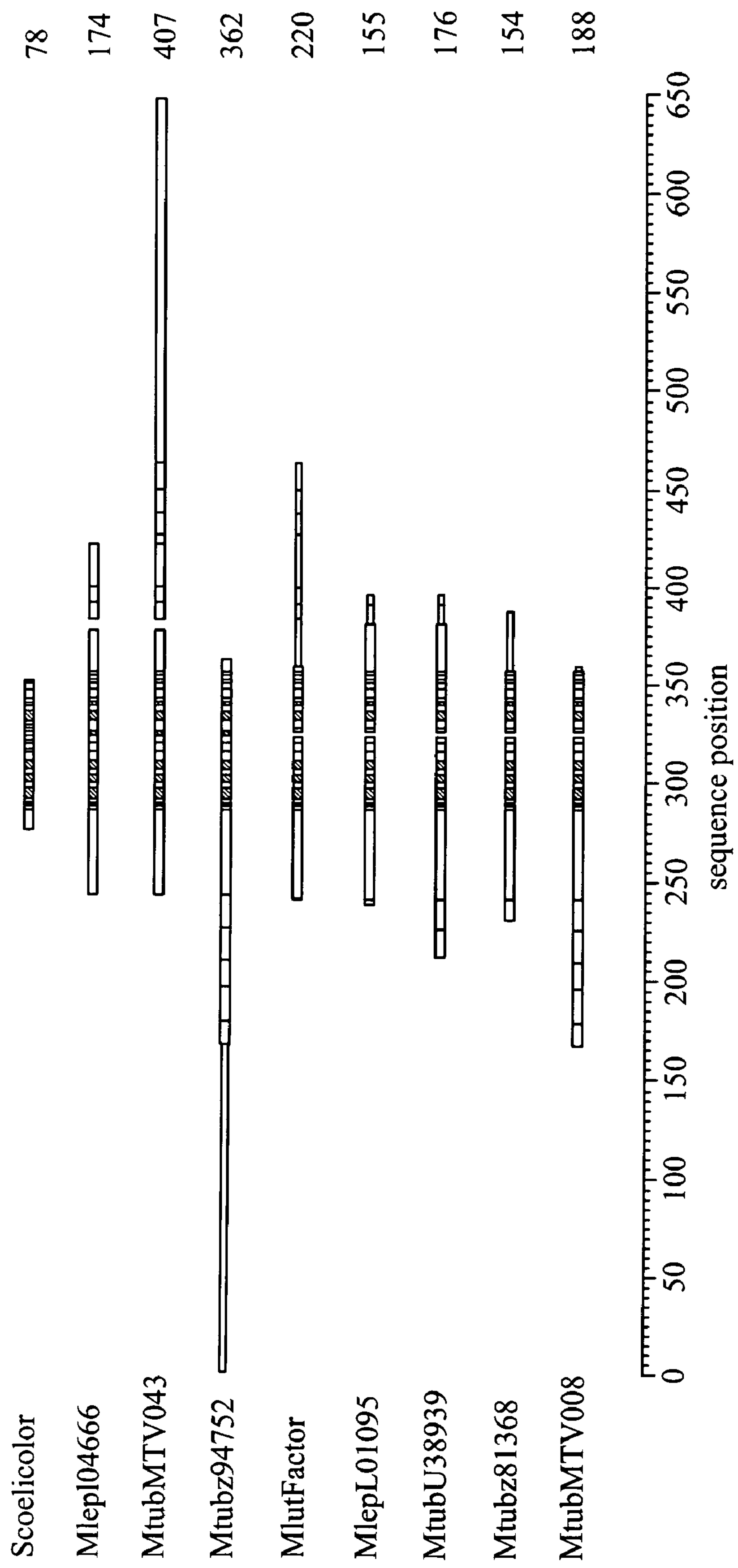
Figure 9B:
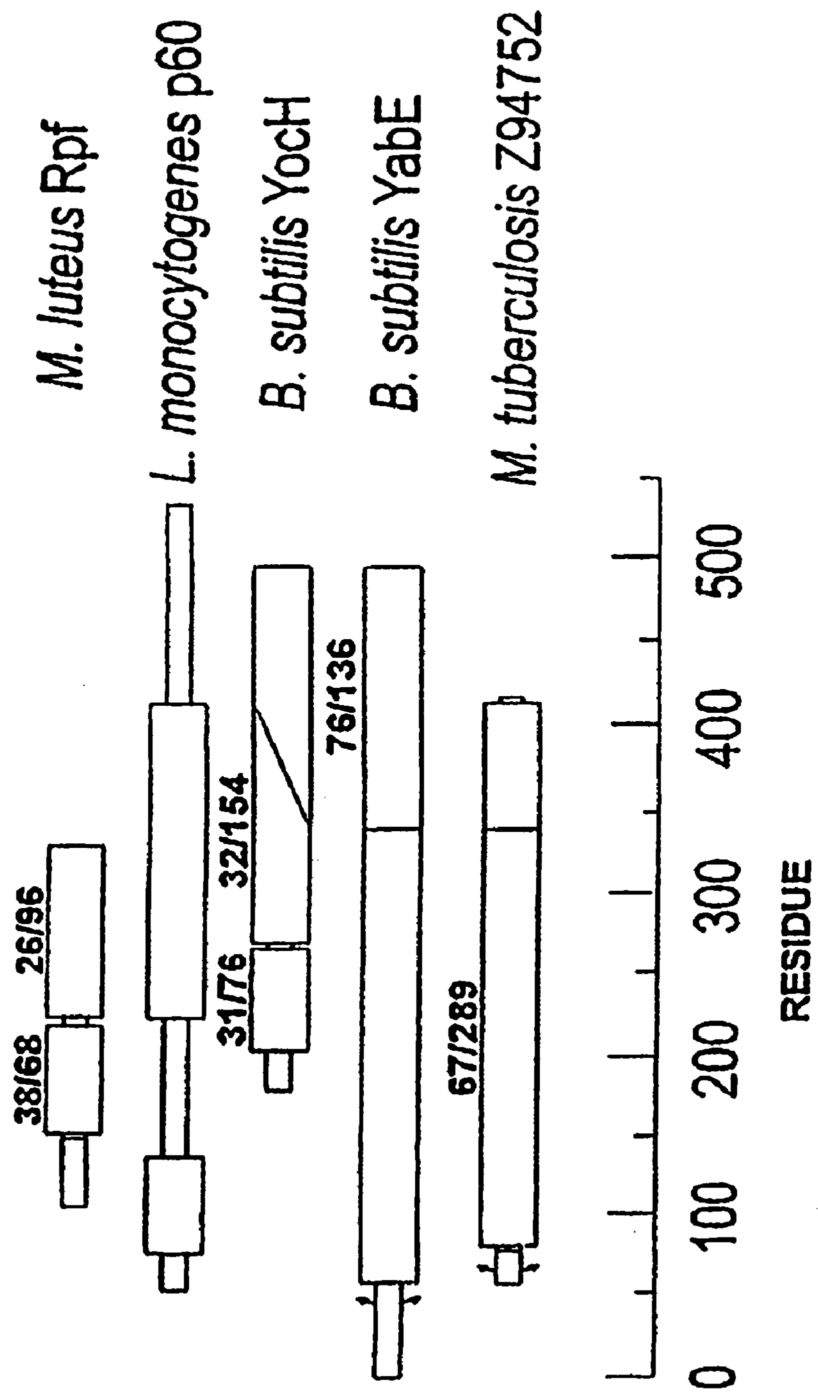

FIGS. 9A and 9B: Part A. Blocked alignment of nine RP-factors (as explained infra, MtubZ94752 may be a cognate receptor). Areas of sequence identity/similarity are indicated by the shaded areas. The *S. coelicolor* gene product shown is a fragment. Part B. Schematic showing the domain structure of some gene products in the RP-factor family.

Figure 10:
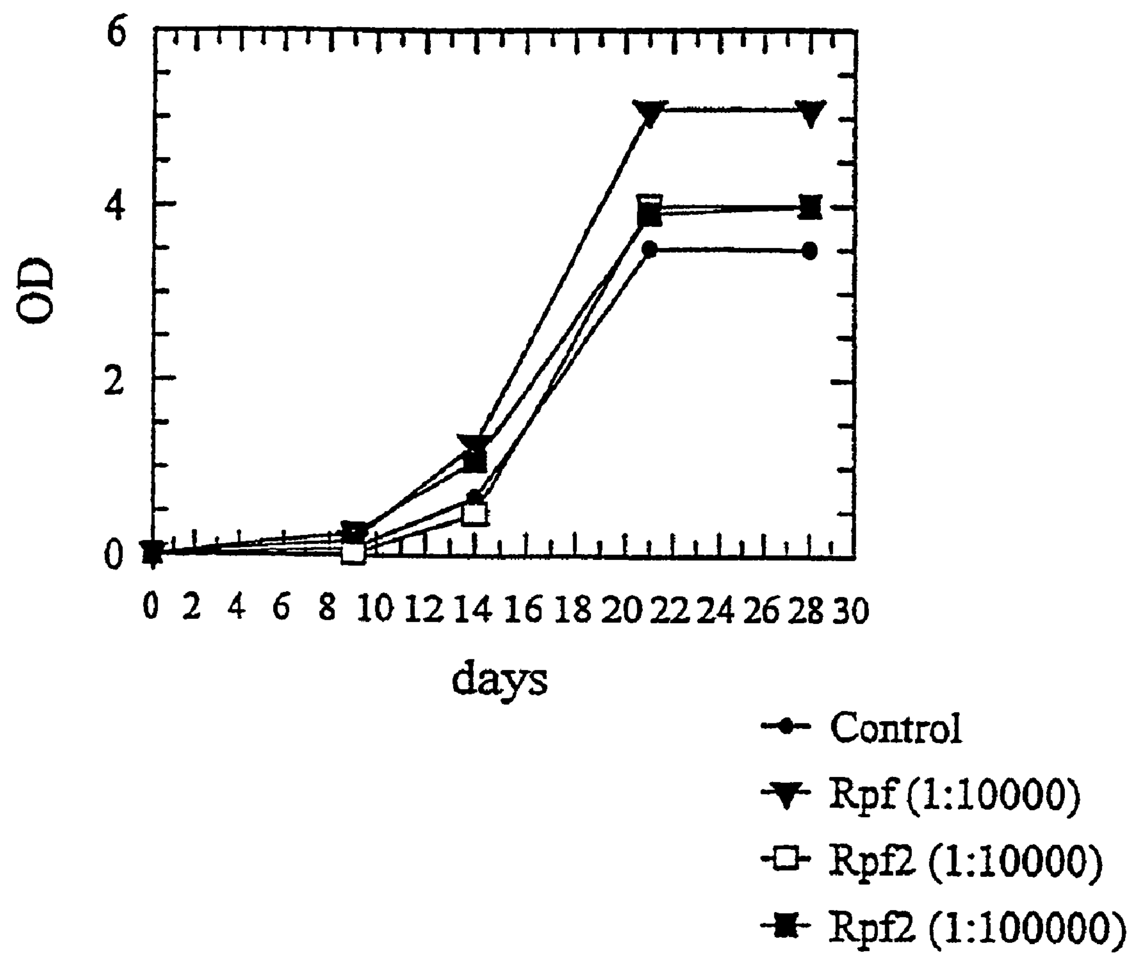

FIG. 10: Effect of recombinant RP-factor on growth of *M. tuberculosis* in Sauton medium. Sauton medium containing 0.05% Tween-80™ and 100 μMol/L Na oleate+10% (v/v) supplement (which contains, per liter, 50 g bovine serum albumin, 20 g glucose, 8.5 g NaCl) was inoculated to an initial cell density of $31\times10^{3}$ cfu/ml (viable count determined by plating on agar-solidified Middlebrook 7H9 medium containing 10% v/v supplement, composition as detailed above) [total count by microscopy=$10^{6}$ cells per ml] with a 2.5 month-old culture of *M. tuberculosis* strain H37Ra grown in the same medium. Growth of tube cultures at 370 C. was measured by determining the $OD_{600nm}$ at intervals for 28 days. The undiluted concentrations of the RP-factors, Rpf (*M. luteus*) and Rpf2 (*M. tuberculosis*), employed for these 15 experiments were ca. 10 μg/ml.

EXAMPLES

Material and Methods

Organisms and Media.

*Micrococcus luteus* NCIMB 13267 (previously described as "Fleming strain 2665") was grown aerobically at 30° C. in shake flasks in lactate minimal medium (LMM) containing L-lactate as described previously. When the culture had reached stationary phase agitation was continued at 30° C. for up to 2 months. Cultures were then held aerobically at room temperature without agitation for period for up to a further 2-3 months. The apparent initial viability of these cultures at this point (measured by comparing the plate count with the microscopic count) was less than $10^{-3}$.

*Mycobacterium smegmatis* ("fast" strain, All-Russia State Institute for Control of Veterinary Preparations, Moscow) was grown in either Sauton medium or nutrient broth E (LabM). Overnight pre-cultures were used to inoculate cultures to an initial density of $10^3$ cells/ml. *Mycobacterium bovis* (BCG), *Mycobacterium tuberculosis* H37RV and *Mycobacterium avium* were grown in Sauton medium.

*M. luteus* Spent Medium Preparation.

Supernatant was obtained after the centrifugation of late logarithmic phase *M. luteus* cultures (200-1000 ml) grown in lactate minimal medium or in the same medium in which lactate was replaced by succinate plus 0.01% yeast extract from which macromolecules had been removed by dialysis. The inoculum consisted of 2% of cells grown in rich medium (Broth E, LabM) and then washed in LMM lacking lactate. The supernatants were passed through a 0.22 μm filter (Whatman) before use.

*M. luteus* Cell Viability by Plating.

Plates consisting of 1.3% Nutrient Broth E (LabM) or lactate minimal medium were used. Cell dilutions were made in quadruplicate with centrifuged and autoclaved spent 20 medium taken from the starved culture. Plates were incubated at 30° C. for 3-5 d.

*M. luteus* Cell Viability by MPN.

The MPN assay was performed in a Bioscreen C optical growth analyzer (Labsystems, Finland) using lactate minimal medium supplemented by 0.5% lactate and 0.05% of yeast extract as a resuscitation medium. Dilutions of starved cells were made as described. 10 μl of each dilution (5-10 replicates) were added to a well containing 200 μl of either lactate minimal medium supplemented by 0.5% lactate and 0.05% of yeast extract or the same medium with fraction tested (2-20 μl). Growth (optical density) was monitored using a 600 nm filter. Plates were incubated at 30° C. with intensive continuous shaking. The overall measurement period was 120 h, each well being measured hourly.

The fractions obtained after chromatography were dialysed against elution buffer 2 (see below), diluted in resuscitation medium in various proportions (1:10, 1:100, 1:500, 1:1000, 1:5,000, 1:10,000) and filtered through 0.22 μm Gelman filters before testing. The calculation of the MPN was based on published Tables.

Total Cell Counts

Unstained cells were counted with a phase-contrast microscope and an improved Neubauer counting chamber. In long-term experiments with mycobacteria, organisms 10 were stained with Ziehl-Neelsen reagent before counting.

Chromatography

Pre-wetted DEAE cellulose was added to culture supernatant (1:10 v/v) and incubated at 4° C. for 1 h with slow stirring. The cellulose was loaded into a column, and washed with 5 volumes of buffer 1 consisting of 10 mM Tris-Cl, 1 mM EDTA, 1 mM DTT, 10% (v/v) glycerol, pH 7.4 with 10 mM KCl. The column was eluted stepwise with 2-3 bed volumes of 0.3M KCl in buffer 1. The fraction obtained was slowly diluted with buffer 1 on ice to give a final KCl concentration of 0.08M. Forty column volumes of this fraction was then loaded onto a DEAE Serharose™ fast flow column (1 part of Sepharose™ pre-equilibrated with buffer 1 containing 0.08M KCl). The column was washed with 5 bed volumes buffer 1 containing 0.08M KCl and eluted stepwise with 3 volumes of 0.25M KCl in buffer 1. The fraction obtained was again slowly diluted with buffer 1 on ice to a final KCl concentration of 0.08M, filtered through a 0.22 μm Gelman filter and loaded onto a Mono a® column (model HR5/5, pre-packed, Pharmacia) equilibrated with buffer 2 consisting of 10 mM Tris-Cl, 10% glycerol, pH 7.4 containing 0.08M KCl. The Mono Q® column was eluted by a linear gradient from 0.08 M to 0.28 M KCl in buffer 2 (the total volume of the elution was 20 ml). The flow rate and fraction size were 1 ml/min and 1 ml/tube respectively. All manipulations except the Mono Q® chromatography step were performed at 4° C. The fractions obtained were dialysed against 10 mM Tris-Cl containing 10% glycerol (dialysis is important for the retention of activity) and stored at 4° C. for up to 5 days without loss of activity. For prolonged storage in a deep freeze, fractions were dialysed in the same way and glycerol added to a final concentration of 20-30% w/v. The protein content in purified preparations was estimated by tryptophan fluorescence using lysozyme as a standard.

Trypsin Treatment:

Trypsin was added to the active, dialysed fraction obtained from the Mono Q® column and diluted by LMM supplemented with 0.5% w/v lactate and 0.05% yeast extract (1:100) (the final concentration of trypsin was 50 ug/ml). The mixture was incubated for 30 min at 370 C. The reaction was stopped by the addition of trypsin inhibitor (100 ug/ml). In control experiments trypsin inhibitor was added to the mixture (100 ug/ml) prior to incubation.

PAGE Electrophoresis.

Sodium dodecyl sulfate-polyacrylamide gel electrophoresis (SDS-PAGE) was performed according to Laemmli. Chromatographic fractions were dialysed against 10 mM Tris HCl, pH 7.4 for 4-5 h, dried in a speed-vacuum apparatus (1.5 h), dissolved in sample buffer (Sigma, S-3401), loaded onto 15% acrylamide gel and run at a constant voltage of 200V. The gel was stained with colloidal Coomassie™ G (Sigma).

Chemicals.

Nutrient Broth E, yeast extract and agar were obtained from Lab M, whilst L-lactate (Li salt), succinate, trypsin, soybean trypsin inhibitor and DEAE-Sepharose™ fast flow were obtained from Sigma. DEAE cellulose DE52 was obtained from Whatman, and Mono S® and Mono Q® from Pharmacia. Other chemicals were of analytical grade and were obtained from Sigma or BDH.

Protein microsequence data from the N-terminus (ATVDTWDRLAEexSNGTxD) (SEQ ID NO: 38) and an internal peptide (VGGEGYPHQASK) (SEQ ID NO: 42) obtained from the purified RP-factor were used to design two oligonucleotides, denoted A1 [GCSACSGTSGACACSTGGGACCGSCTSGCSGAG] (SEQ ID NO: 37) and A2 [GCYTGRTGIGGRTAICCYTCICC] (SEQ ID NO: 41), respectively. Taq polymerase was employed under standard conditions to amplify a 147 bp PCR product from *M. luteus* DNA with these primers. The PCR product obtained from *M. luteus* DNA with these two primers was labeled with digoxygenin and used as a probe for Southern hybridization experiments. Sma1-digested genomic DNA was size-fractionated by agarose gel electrophoresis and circa 1.4 kbp fragments were cloned in pMTL2O and established in *E. coli* strain DH5a. Two recombinant plasmids carrying the desired insert were detected by hybridization, confirmed by PCR using oligonucleotides A1 and A2, and one of them was manually sequenced on both strands using the dideoxy chain termination method.

Standard procedures were employed to isolate DNA from *M. luteus* and *M. smegmatis*. *Streptomyces rimosus* DNA was kindly supplied by Dr. D. Hranueli. Southern hybridisations with *M. smegmatis* and *S. rimosus* DNA were initially carried out under non-stringent conditions (0.5 SSC, 37° C.). Stringent conditions (0.1 SSC, 650 C.) were subsequently employed for screening an ordered cosmid library of *Streptomyces coelicolor* A3(2) DNA.

Purification of RP-Factor

RP-factor purified from culture supernatants of cells grown in lactate minimal medium, according to the protocol described in Materials and Methods, revealed the presence of a significant amount of polymeric material eluted from all types of columns used, which inhibited both the resuscitation of dormant cells and the growth of viable cells of *M. luteus*. Moreover, elevated concentrations of this material could even cause the lysis of cells (not shown). This inhibitory material appears to be a polymer derived from lactate, as lactate-containing LMM stored for 10 hours at room temperature without cells and subjected to the same procedure of purification revealed inhibitory properties similar to those of this spent medium. To avoid this problem we replaced lactate in the growth medium with succinate, although for good growth it proved necessary to add a small 5 amount (0.01% w/v) of yeast extract dialysed to remove macromolecules.

Using succinate-grown cultures, the active fraction was purified by a combination of anion exchange media (see Material and Methods). The final activity was eluted at around 180 mM KCl from a linear KCl gradient (from 0.08 to 0.28M KCl) on a Mono Q® column in 3 adjacent fractions (FIG. 3). It is worth mentioning that it proved important to dialyse the fractions before testing their activity because some fractions were inactive before dialysis. Active fractions did not change their resuscitation activity after dilution up to 400 times (v/v).

Interestingly, those fractions which were active in causing resuscitation could also increase the growth rate of viable cells.

The resuscitation-promoting material from the final purification step was checked by SDS-PAGE. The final product (FIG. 3C) proved to consist of a single protein with a molecular weight estimated to be ca 16 kD. All active fractions consist of single band with maximum content of protein in fraction N9.

Cloning of the RP-Factor Gene

Two primers were designed from protein microsequence data obtained for the N-terminus of the purified RP-factor and for an internal peptide. They were used to amplify a 147 bp fragment of *M. luteus* DNA, which was cloned and sequenced. The complete gene was then obtained by a combination of inverse PCR using oligonucleotides G1 and G2 and isolation of a 1.4 kbp SmaI genomic restriction fragment. Sequencing revealed that the original PCR product was part of a gene capable of encoding a protein having a signal sequence (FIG. 2A). The predicted size of the secreted form of the gene product is 19,148 Dal, and its predicted N-terminal amino acid sequence agrees with the protein microsequence data, including residues that were not used in primer design (FIG. 2A). The fact that the predicted gene product is larger than the RP-factor purified from culture supernatants suggests that it may, for example, be secreted as a precursor which is converted to its biologically active form upon contact with its cognate receptor/convertase.

Identification of RP-Factor Homologues

A BLAST search was undertaken using the predicted amino acid sequence of the ORF from *M. luteus* as query. Seven genes with substantial similarity have been sequenced previously. Five are found in *M. tuberculosis* and two in *Mycobacterium leprae* (FIG. 1A). One or more gene products in each organism appear to have a secretory signal sequence (underlined in FIG. 1A). The functions of the predicted products of these mycobacterial genes are unknown; they were found by genome sequencing projects. The BLAST search also revealed similarity between residues 126-220 of the RP-factor and a conserved segment of the (major extracellular) p60 proteins that have been implicated in adherence of *Listeria* spp. to 3T6 mouse fibroblasts suggesting, perhaps, a possible role for the RP-factor or a proteolytic product thereof in adhesion in *M. luteus* (FIG. 1E).

In common with *M. tuberculosis* and *M. leprae, M. luteus* contains a second gene similar to that encoding the RP-factor. Southern hybridisation experiments, using DNA samples cleaved with a range of different restriction enzymes, and the cloned 147 bp fragment as probe (FIGS. 5A & B), reveal two hybridising bands. The stronger hybridisation signal arises from the gene encoding the secreted RP-factor. The other gene may correspond to one of the other mycobacterial genes identified above.

Southern hybridisation experiments, using the 147 bp fragment as probe, as well as PCR experiments, using two oligonucleotides based on highly conserved amino acid motifs as primers, indicate that genes encoding proteins similar to the RP-factor are of widespread occurrence, at least throughout Gram-positive bacteria whose DNA has a high G+C content. Similar genes are detectable by either or both of these methods in all six *Streptomyces* species we have tested, including *Streptomyces rimosus* (FIG. 5C) as well as in other mycobacteria, including *Mycobacterium* I (four similar genes 5—FIG. 5C), *Mycobacterium bovis* (BCG) and *Corynebacterium glutamicum* (2 similar genes).

Domain Structure

The sequence information shows that the RP-factor gene and all of its mycobacterial homologues share a secretory signal sequence and a particularly highly conserved, ca. 70-residue segment. One (MTubZ94752) also has a membrane anchoring motif. The conserved 70-residue segment is a candidate for a signalling domain. Most of this segment is weakly hydrophilic (Kyte-Doolittle) and is predicted to form amphipathic á-helical (Garner-Robson; Chou-Fasman) or β-sheet regions (Eisenberg). Overall, the segment has a low surface probability (Emini). The C-terminal section, by contrast, is much less highly conserved and might be considered a better candidate for determining localization or specificity (i.e. be a cellular compartment-targeting or specificity-determining domain). By analogy with other protein signalling systems (e.g. many pro-hormones in animals, and systemin in plants) it is possible that the proximate signalling molecule is a proteolytically cleaved product.

Two acidic residues, D7 & E13 (numbering according to the *M. luteus* secreted protein), within this segment are absolutely conserved. The KAEQIKRAE segment (residues 51-59; SEQ ID NO: 64) represents an island of particularly high surface probability. These elements may form part of functional domains within the RP-factor protein.

The conserved domain contains four conserved tryptophan residues (one of which is in a region of high surface probability DTWDR-residues 4-8; SEQ ID NO: 65). In the complex between human growth hormone and its first bound receptor, interactions involving two surface-located tryptophan residues in the receptor account for more than 75% of the binding free energy of the complex (Clackson and Wells, Science 267, 383-386, 1995). The two conserved cysteine residues may form a disulphide bridge.

Alignments showing the domain structures of the various proteins are shown in FIGS. 9A 5 and 9B.

RP-Factor Activity

Figure 6B:
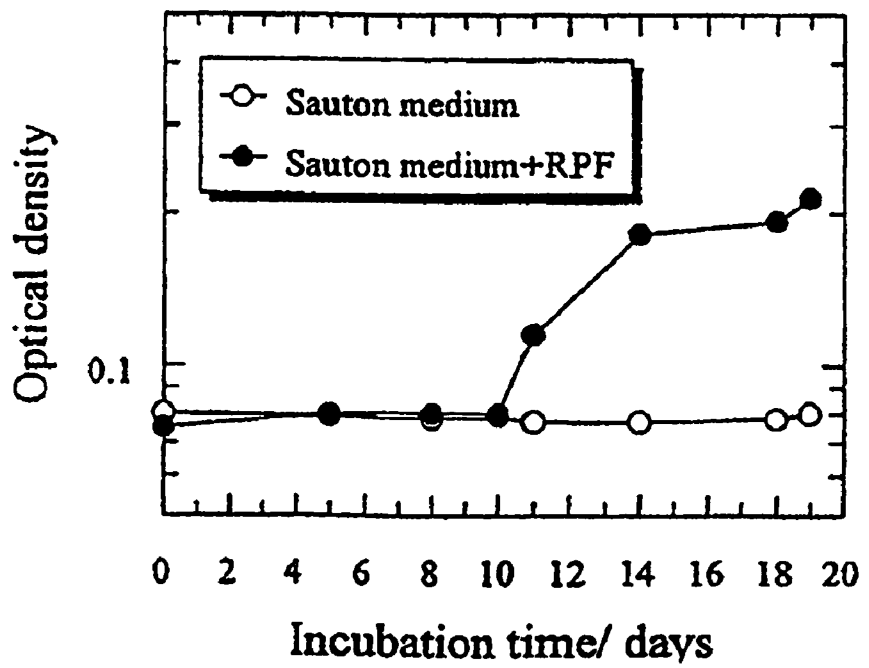

As well as resuscitating dormant cells, the purified RP-factor from *M. luteus* has been tested for growth-stimulatory activity against *M. luteus* and several other organisms. It strongly stimulates the growth of *M. luteus* and *M. smegmatis* and it appears to have weaker activity on *M. tuberculosis, M. bovis* (BCG) and *M. avium* (see FIG. 6). In all cases, there is a shortening of the apparent lag phase in batch culture (see FIGS. 3D, 4B, 6B and Table 1). The factor is active in poor media and in poor media supplemented with yeast extract and it loses activity after boiling or treatment with trypsin.

When ca. 40 pMol/L RP-factor was added to washed cells of *Mycobacterium smegmatis*, growth occurred after 20-24 hr, whereas the control lacking RP-factor showed no growth after 6 days. Experiments with slowly growing mycobacteria yielded similar results.

Growth of *M. bovis* (BCG) was also strongly stimulated by 40 pMol/L RP-factor: growth occurred after 14 days whereas the control lacking RP-factor showed no growth after 90 days. Finally, RP-factor also stimulated the growth of *Mycobacterium tuberculosis, Mycobacterium smegmatis, Mycobacterium avium* and *Mycobacterium kansasii* (see Table 1).

TABLE 1

Purified *M. luteus* RP-factor stimulates growth of mycobacteria

| Organism | Bacterial growth[$] RP-factor omitted | Bacterial growth[$] RP-factor added |
|---|---|---|
| *Mycobacterium tuberculosis* H37Ra | 1.3 ± 1.9 (5) | 110 ± 32 (5) |
| *Mycobacterium Tuberculosis* HR37Rv | 1.5 ± 2 (4) | 45 ± 28 (4) |
| *Mycobacterium Avium* | 0 (3) | >300 (3) |
| *M. bovis* (BCG) | 0 (5) | 54 ± 38 (5) |
| *M smegmatis** | 0 (8) | 225 ± 44 (8) |
| *Mycobacterium kansasii* | 2.5 ± 2.5 (3) | 90 ± 77 (3) |

[$]Growth was estimated microscopically (magnification times 600) after 14 days of 5 incubation; ca. 50 µl of each culture was fixed, stained using Ziehl-Neelsen reagent and counted. Values in the body of the Table are average numbers of cells in a microscope field (10-20 fields counted) ± standard deviation with the number of determinations in parentheses. RP-factor (after elution from the Mono Q ® column and dialysis) was used at a concentration of circa 40 pMol/L; activity was lost after either trypsin treatment, heating (autoclaving) or filtration through a 12 kDal cutoff membrane.
*Washed cells of *M. smegmatis* were used for this experiment.

Isolation and Characterisation of the Gene Encoding the Second Homologue from *M. luteus*

A combination of inverse PCR using oligos G1 and G2 (see FIG. 2A) as primers, and cloning of suitably sized genomic restriction fragments, can be employed to isolate the gene encoding the second homologue from *M. luteus*. The sequence of the gene can then be determined, taking care to eliminate any possible PCR errors by analysis of genomic clones and direct sequencing of PCR fragments obtained by combining the products of multiple, independent PCR reactions. Comparative sequence analyses of the proteins from *M. luteus, M. leprae* and *M. tuberculosis* can then be used to refine predictions concerning residues, sequence motifs and structural motifs which may be important for biological function.

Over-Expression and Purification of *M. luteus* and *M. tuberculosis* Gene Products in *E. coli*

PCR primers can be designed, incorporating suitable restriction sites such that sequences encoding the secreted forms of the *M. luteus* and the *M. tuberculosis* RP-factors can be amplified and inserted, in the correct reading frame, into commercially available plasmids (pET or pCAL vectors). The PCR-amplified fragments can first be cloned in a pBluescript KS II vector (Stratagene) so that their entire sequence can be verified, to eliminate possible PCR errors. (This material can also be employed for site-directed mutagenesis—vide infra.) The pET or pCAL constructs can then be employed to obtain controlled expression of large quantities of histidine- or calmodulin binding peptide-tagged proteins that can be purified, essentially to homogeneity, in a single step. Finally, the tags used in protein purification can be removed (using enterokinase or thrombin, as appropriate).

Expression of RP-Factor from *Micrococcus luteus* in *E. coli*

Two primers [5'-GTCAGAATTCATATGGCCACCGTGGACACCTGGG-3'] (SEQ ID NO: 46) and [5'-TGACGGATCCTATTAGGCCTGCGGCAGGACGAG-3'] (SEQ ID NO: 47) were employed to amplify (5 cycles of 30 s at 94° C., 30 s at 60° C., 30 s at 72° C., followed by 15 cycles of 30 s at 94° C., 60 s at 72° C.) the RP-factor coding sequence (i.e. lacking the signal sequence) from the cloned 1.4 kbp SmaI fragment of genomic DNA. It was first established in *E. coli* DH5α as a 567 bp EcoRI-BamHI fragment in pMTL20 and then excised as a 562 bp NdeI-BamHI fragment, inserted into pET19b (Novagen) and re-established in *E coli* DH5 á. The sequence of the PCR product and vector-insert junction in this plasmid, denoted pRPF1, was verified. RP-factor was expressed from RPF1 after transforming it into *E. coli* HSM174(DE3). The protein, containing a His10-tag at the N-terminus, was isolated by sonicating bacteria, previously grown to an $OD_{600nm}$=0.6 and induced with 0.4 mM IPTG for 4 h, in a modified binding buffer (MBB—5 mM imidazole pH7.9/0.5M NaCl/20 mM Tris-HC1/8M urea) containing 5 mM DTT and 2 mM EDTA. After low speed centrifugation, low MW compounds, including EDTA and DTT, were removed by elution through a Sephadex™ G10 column pre-equilibrated with MBB. A Ni2+-chelation column (Ni2+-coordinated iminodiacetic acid immobilized on Sepharose™ 6B), was loaded with the G10 eluate, washed with 20 vol MBB and then successively eluted with four 10 vol aliquots of MBB containing 0.01 M, 0.05 M, 0.2 M and 1 M imidazole, respectively. The column was finally eluted with strip buffer (20 mM Tris-HCl, pH 7.9/100 mM EDTA/0.5 M NaCl). Monoclonal anti-(polyHis) antibodies (Sigma, clone His-1) were employed for immunoblot analysis of fractions subjected to SDS PAGE electrophoresis and electroblotted using standard methods. Fractions were dialysed against buffer 2 and assayed for biological activity as indicated above.

Analysis of Recombinant RP-Factor

The coding sequence corresponding to the secreted form of RP-factor, starting at residue $A_{39}$, was inserted into pET 19b to generate plasmid pRPF1 (vide infra). Extracts of IPTG-induced *E. coli* strain HSM174(DE3) containing pRPF 1 were challenged with a poly-His antibody. A strong signal was associated with a protein (apparent size 29 kDal, predicted size 22 kDal) which was eluted from the affinity column by 1M imidazole (FIG. 7A). The His-tagged protein from HSM174(DE3) reduced the apparent lag phase of viable cells of *M. luteus*, whereas the control (material eluted from the same column under the same conditions when an extract from cells containing plasmid vector only was applied) showed no activity (FIG. 7B). The association of biological activity with the recombinant protein, produced in *E. coli* containing pRPF, and the absence of biological activity in the isogenic control containing pET19b, demonstrates unequivocally that the active molecule is indeed a product of the rpf gene.

Antibody Preparation

A rabbit was immunized three times at one week intervals using recombinant RP-factor (the recombinant protein prepared as described above). The protein was administered at 300 µg of protein per injection in incomplete Freud's adjuvant (0.5 ml protein and 0.5 ml adjuvant) Blood was collected before administration was started and on the 11th day after the last injection. The immunoglobulin fraction was obtained by standard procedures using PEG. Antibodies were additionally purified on a protein G-Superose™ column according to the standard (Pharmacia) protocol. The final protein concentration to was adjusted spectrophotometrically to 1 mg/ml.

Alternatively, monoclonal antibodies can be produced using established techniques.

Use of Anti-RP-Factor Antibody to Inhibit Bacterial Growth

*Micrococcus luteus* was inoculated at an initial density of $5\times10^5$ per ml into lactate minimal medium (LMM) and the $OD_{600nm}$ was monitored at intervals. Growth of the cultures was monitored over 140 hours, and the presence of the anti-RP-factor serum (prepared as described above under "Antibody preparation") completely inhibited bacterial growth (see FIG. 8).

Expression of a *M. tuberculosis* RP-Factor in *E. coli*

Two primers [5'-ATCAGAATTCATATGGACGACATCGATTGGGACGC-3'] (SEQ ID NO: 48) and [5'-CGCAGGATCCCCTCAATCGTCCCTGCTCC-3'] (SEQ ID NO: 49) were employed to amplify (5 cycles of 30 s at 94° C., 30 s at 58° C., 30 s at 72° C., followed by 25 cycles of 30 s at 94° C., 60 s at 72° C.) the RP-factor coding sequence (i.e., lacking the signal sequence) from *M. tuberculosis* H37Rv genomic DNA. The PCR product was first established in *E. coli* DH5a as a 336 bp EcoRI-BamHI fragment in pMTL20 and then excised as a 331 bp NdeI-BamHI fragment, inserted into pET19b (Novagen) and re-established in *E. coli* DH5a. The sequence of the PCR product and vector-insert junction in this plasmid, denoted pRPF2, was verified. The *M. tuberculosis* RP-factor was expressed from pRPF2 after transforming it into *E. coli* HSM174(DE3). The protein, containing a His10-tag at the N-terminus, was isolated by sonicating bacteria, previously grown to an OD600 nm=0.9 and induced with 0.4 mM IPTG for 4 h, in binding buffer (BB—5 mM imidazole pH7.9 /0.5M NaCl/20 mM Tris-HCl/8M urea). After low speed centrifugation, a Ni2+-chelation column (Ni2+-coordinated iminodiacetic acid immobilised on Sepharose™ 6B), was loaded with the supernatant, washed with 20 vol 13B, 20 vol BB containing 100 mM imidazole, and then eluted with 10 vol BB containing 0.5 M imidazole. Additional purification was achieved by Mono Q® column chromatography (vide infra, save that the salt gradient was from 0.1 M to 1M NaCl). Monoclonal anti-(polyHis) antibodies (Sigma, clone His-1) were employed for immunoblot analysis of fractions subjected to SDS PAGE electrophoresis and electroblotted using standard methods. Fractions were dialysed against buffer 2 and assayed for biological activity as indicated above.

Analysis of a Recombinant *M. tuberculosis* RP-Factor

The coding sequence corresponding to the secreted form of the *M. tuberculosis* RP-factor (g1655671; acc. no. Z81368), starting at residue $D_{50}$, was inserted into pET19b to generate plasmid pRPF2 (vide infra). Extracts of IPTG-induced *E. coli* strain HSM174(DE3) containing pRPF2 were challenged with a poly-His antibody. A strong signal was associated with a protein which was eluted from the affinity column by 0.5M imidazole. The histidine-tagged protein from HSM174(DE3) caused a slight but significant enhancement of the growth of *M. tuberculosis* H37Rv, as shown in FIG. 10. It also stimulated the growth of *M. luteus* in LMM. The control culture attained a final $OD_{600nm}$ of 1.0, whereas cultures containing the RP-factor (1:100,000 dilution) attained a final $OD_{600nm}$ of between 2.0 and 6.0.

Effect of *M. luteus* RP-Factor on Growth of *Mycobacterium tuberculosis* Cells Isolated from Macrophages In three independent experiments, dormant/latent *M. tuberculosis* cells isolated from cultured murine peritonial macrophages were resuscitated by the *M. luteus* RP-factor. The total number of *M. tuberculosis* cells in the heterogeneous suspension obtained from murine macrophages was determined microscopically. The viable cell count was determined by plating on agar-solidified Sauton medium containing 10% (v/v) supplement (which contains, per liter, 50 g bovine serum albumin, 20 g glucose, 8.5 g NaCl) or by the MPN method, using liquid Sauton medium containing 10% (v/v) supplement (see above).

The viable count (MPN) of these cell suspensions was enhanced between 25 and 2,500 times by the presence of the *M. luteus* RP-factor (added at a final concentration of 10 ng/ml) (see Table 2). All values in the body of the table are numbers of bacteria per ml suspension Peritoneal macrophages were obtained from white mice (wild type) by a standard protocol. Infection of macrophages by *M. tuberculosis* "Academiya" (laboratory strain) was performed in vivo by intraperitonial injection of $10^6$ cells (total count) per mouse followed by incubation for 6 days (1st passage). For the second and third passages macrophage cells in monolayers were infected using *M. tuberculosis* cells isolated from macrophages from the previous passage.

TABLE 2

Effect of *M. luteus* RP-factor on growth of *Mycobacterium tuberculosis* cells isolated from macrophages

| Experiment | Total count [x] (determined microscopically) | Viable count (determined by plating) | Viable count (MPN) | MPN in presence of RP-factor |
|---|---|---|---|---|
| I | $10^6 > x > 10^5$ | 90 | 70 | $4.10^3$ |
| II | $10^6 > x > 10^5$ | 9 | 40 | $1.10^3$ |
| III | $2.10^6$ | <1 | <1 | $24.10^3$ |

Macrophages were grown as a monolayer on plastic petri dishes ($10^6$ cells/5 $cm^2$) in standard RPMI medium containing gentamicin and penicillin (10 ig/ml, each) under standard conditions ($CO_2/O_2$ mixture in a 37° C. incubator). *M. tuberculosis* cells were recovered from macrophages by passing them repeatedly through a thin syringe needle. Macrophage cell debris was removed by low speed centifugation and *M. tuberculosis* cells were then collected by centrifugation at higher speed.

Effect of yabE and yocH Knockout Mutations on Growth of *Bacillus subtilis*

The entire yabE coding region together with flanking sequences was amplified from *B. subtilis* genomic DNA using primers D11 [5'-GAAGAGAATTCCTTCCATCACGA-3'] (SEQ ID NO: 50) and D12 [5'-CCAAACGAATTCGGTCAATCAC-31 (SEQ ID NO: 51) as a 1803 bp product. A 1186 bp HindIII-BclI fragment encompassing the 3' end of the coding sequence was excised from the PCR product, ligated with HindIII+BamHI-digested pMTL20, and used to transform *E. coli* strain DH5a with selection for ampicillin-resistance. Plasmid pYABE was isolated from one of the transformants. A 763 bp HindIII-BamHI fragment from entirely within the yabE coding sequence was excised from the pYABE, ligated with HindIII+BamHI-digested pMUTIN4, an integrating plasmid that may be employed for generating knockout mutations in *B. subtilis* (Edwards & Errington, 1997, Molecular Microbiology, 24, 905-915) and used to transform *E. coli* strain XL 1-Blue with selection for ampicillin-resistance. Plasmid pYAB2, containing an internal segment of the yabE coding sequence, was isolated from one of the transformants. A 1207 bp HindIII-EcoRI fragment encompassing the 3' end of the yabE coding sequence was excised from pYABE, ligated with HindIII+EcoRI digested pMUTIN4 and used to transform *E coli* strain XL1-Blue with selection for ampicillin-resistance. Plasmid pYAB3, containing the 3' end of the yabE coding sequence, was isolated from one of the transformants.

The entire yocH coding region together with flanking sequences was amplified from *B. subtilis* genomic DNA using primers D10 [5'-GCAAGGATCCCAGACTAAAAAAACAG-3'] (SEQ ID NO: 52) and D9 [5'-ATCAGGATCCATATTATTAGTTTAAGA-3'] (SEQ ID NO: 53) as a 1145 bp product. A 358 bp HpaI fragment from entirely within the yocH coding sequence was excised from the PCR product, ligated with SmaI-digested pMTL20, and used to transform *E. coli* strain XL1-Blue with selection for ampicillin-resistance. Plasmid pYOC2a, containing an internal segment of the yocH coding sequence, was isolated from one of the transformants. The insert in this plasmid was then excised from pYOC2a as a 385 bp EcoRI-HindIII fragment and inserted into pMUTIN4, to yield pYOC2. A 307 bp HindIII–BamHI fragment encompassing the 3' end of the yocH coding sequence was excised from the 1145 bp PCR product, ligated with HindIII+BamHI digested pMUTIN4, and used to transform *E. coli* strain DH5á with selection for ampicillin-resistance. Plasmid pYOC3, containing a DNA segment encompassing the 3' end of the yocH coding sequence, was isolated from one of the transformants.

Plasmids pYAB2, pYAB3, pYOC2 and pYOC3 were linearised with ApaI, which cleaves once in the pMUTIN4 vector sequences, ligated with T4 DNA ligase and employed to transform *Bacillus subtilis* strain SA253 nonA nonB leuA8 arg-15 with selection for resistance to erythromycin on a rich nutrient medium (LB+1 ig Em/ml). $Em^R$ transformants were then picked and verified by Southern hybridization. Using the integrating plasmid as probe, and digesting the chromosomal DNA with ApaI, strains harbouring a single copy of the integrated plasmid gave two hybridising bands whereas the wild type (and any spontaneous $Em^R$ mutants that were present) gave a single hybridising band.

Analysis of the products of transformation with each of the four plasmids indicates that yabE and yocH gene products are required for growth (at least under certain conditions) in *B. subtilis.*

The invention claimed is:

1. A composition comprising a polypeptide purified to essential homogeneity, wherein the polypeptide is selected from the group consisting of:

i) a polypeptide having at least 95% sequence identity with amino acid residues 285 to 355 of SEQ ID NO: 1, amino acid residues 117 to 184 of SEQ ID NO: 2, amino acid residues 44 to 114 of SEQ ID NO: 4, amino acid residues 73 to 140 of SEQ NO: 6, amino acid residues 54 to 121 of SEQ ID NO: 7 or amino acid residues 224 to 318 of SEQ ID NO: 11;

ii) a polypeptide having at least 95(3 sequence identity with SEQ ID NO: 1, SEQ ID NO: 2, SEQ ID NO: 4, SEQ ID NO: 6, SEQ ID NO: 7, SEQ ID NO: 11, SEQ ID NO: 36 or SEQ ID NO: 43:

iii) a polypeptide comprising at least amino acid residues 285 to 355 of SEQ ID NO: 1, amino acid residues 117 to 184 of SEQ ID NO: 2, amino acid residues 44 to 114 of SEQ NO: 4, amino acid residues 73 to 140 of SEQ NO: 6, amino acid residues 54 to 121 of SEQ ID NO: 7 or amino acid residues 224 to 318 of SEQ ID NO: 11: and iv) a polypeptide comprising the amino acid sequence of SEQ ID NO: 1, SEQ ID NO: 2, SEQ ID NO: 4, SEQ ID NO: 6, SEQ NO: 7, SEQ ID NO: 11, SEQ ID NO: 36 or SEQ ID NO: 43.

2. The composition of claim 1, wherein the composition is in a unit dosage form or a form suitable for local or systemic administration.

3. The composition of claim 1, wherein the polypeptide has at least 95% sequence identity with the amino acid sequence of SEQ ID NO: 1.

4. The composition of claim 1, wherein the polypeptide comprises the amino acid sequence of SEQ ID NO: 1.

5. A kit comprising a polypeptide purified to essential homogeneity, wherein the polypeptide is selected from the group consisting of:

i) a polypeptide having at least 95% sequence identity with amino acid residues 285 to 355 of SEQ ID NO: 1, amino acid residues 117 to 184 of SEQ ID NO: 2, amino acid residues 44 to 114 of SEQ ID NO: 1, amino acid residues 73 to 140 of SEQ ID NO: 6, amino acid residues 54 to 121 of SEQ ID NO: 7 or amino acid residues 224 to 318 of SEQ ID NO: 11;

ii) a polypeptide having at least 95% sequence identity with SEQ ID NO: 1, SEQ ID NO: 2, SEQ NO: 4, SEQ ID NO: 6, SEQ NO: 7, SEQ ID NO: 11, SEQ ID NO: 36 or SEQ ID NO: 43;

iii) a polypeptide comprising at least amino acid residues 285 to 355 of SEQ ID NO: 1, amino acid residues 117 to 184 of SEQ ID NO: 2, amino acid residues 44 to 114 of SEQ ID NO: 4, amino acid residues 73 to 140 of SEQ ID NO: 6, amino acid residues 54 to 121 of SEQ ID NO: 7 or amino acid residues 224 to 318 of SEQ ID NO: 11; and iv) a polypeptide comprising the amino acid sequence of SEQ ID NO: 1, SEQ ID NO: 2, SEQ TD NO: 4, SEQ ID NO: 6, SEQ ID NO: 7, SEQ ID NO: 11, SEQ ID NO: 36 or SEQ ID NO: 43; and instructions for use.

6. The kit of claim 5, wherein the polypeptide is present in a composition comprising a pharmaceutical excipient.

7. The kit of claim 5, wherein the composition is in a unit dosage form or a form suitable for local or systemic administration.

8. The kit of claim 5, wherein the polypeptide has at least 95% sequence identity with the amino acid sequence of SEQ NO: 1.

9. The kit of claim 5, wherein the polypeptide comprises the amino acid sequence of SEQ NO: 1.

10. The composition of claim 1, wherein the polypeptide has at least 95% sequence identity with the amino acid sequence of SEQ ID NO: 2.

11. The composition of claim 1, wherein the polypeptide has at least 95% sequence identity with the amino acid sequence of SEQ ID NO: 4.

12. The composition of claim 1, wherein the polypeptide has at least 95% sequence identity with the amino acid sequence of SEQ ID NO: 6.

13. The composition of claim 1, wherein the polypeptide has at least 95% sequence identity with the amino acid sequence of SEQ ID NO: 7.

14. The composition of claim 1, wherein the polypeptide has at least 95% sequence identity with the amino acid sequence of SEQ ID NO: 11.

15. The composition of claim 1, wherein the isolated polypeptide has at least 95% sequence identity with the amino acid sequence of SEQ ID NO: 43.

16. The composition of claim 1, wherein the polypeptide comprises the amino acid sequence of SEQ ID NO: 2.

17. The composition of claim 1, wherein the polypeptide comprises the amino acid sequence of SEQ ID NO: 4.

18. The composition of claim 1, wherein the polypeptide comprises the amino acid sequence of SEQ ID NO: 6.

19. The composition of claim 1, wherein the polypeptide comprises the amino acid sequence of SEQ ID NO: 7.

20. The composition of claim 1, wherein the polypeptide comprises the amino acid sequence of SEQ ID NO: 11.

21. The composition of claim 1, wherein the polypeptide comprises the amino acid sequence of SEQ ID NO: 43.

22. The kit of claim 5, wherein the polypeptide has at least 95% sequence identity with the amino acid sequence of SEQ ID NO: 2.

23. The kit of claim 5, wherein the polypeptide has at least 95% sequence identity with the amino acid sequence of SEQ ID NO: 4.

24. The kit of claim 5, wherein the polypeptide has at least 95% sequence identity with the amino acid sequence of SEQ ID NO: 6.

25. The kit of claim 5, wherein the polypeptide has at least 95% sequence identity with the amino acid sequence of SEQ ID NO: 7.

26. The kit of claim 5, wherein the isolated polypeptide has at least 95% sequence identity with the amino acid sequence of SEQ ID NO: 11.

27. The kit of claim 5, wherein the isolated polypeptide has at least 95% sequence identity with the amino acid sequence of SEQ ID NO: 43.

28. The kit of claim 5, wherein the polypeptide comprises the amino acid sequence of SEQ ID NO: 2.

29. The kit of claim 5, wherein the polypeptide comprises the amino acid sequence of SEQ ID: 4.

30. The kit of claim 5, wherein the polypeptide comprises the amino acid sequence of SEQ ID NO: 6.

31. The kit of claim 5, wherein the polypeptide comprises the amino acid sequence of SEQ ID NO: 7.

32. The kit of claim 5, wherein the polypeptide comprises the amino acid sequence of SEQ ID NO: 11.

33. The kit of claim 5, wherein the polypeptide comprises the amino acid sequence of SEQ ID NO: 43.

34. The composition of claim 1, further comprising a pharmaceutical excipient.

35. The composition of claim 1, wherein the polypeptide has at least 95% sequence identity with the amino acid sequence of SEQ ID NO: 36.

36. The composition of claim 1, wherein the polypeptide comprises the amino acid sequence of SEQ ID NO: 36.

37. The kit of claim 5, wherein the polypeptide has at least 95% sequence identity the amino acid-sequence of SEQ ID NO: 36.

38. The kit of claim 5, wherein the polypeptide comprises the amino acid sequence of SEQ ID NO: 36.

* * * * *

UNITED STATES PATENT AND TRADEMARK OFFICE

CERTIFICATE OF CORRECTION

PATENT NO. : 8,383,126 B2
APPLICATION NO. : 11/978257
DATED : February 26, 2013
INVENTOR(S) : Galina V. Mukamolova et al.

It is certified that error appears in the above-identified patent and that said Letters Patent is hereby corrected as shown below:

In the Claims:

At column 77, claim 1, line 22, delete "at least 95(3 sequence identity" and replace it with --at least 95% sequence identity--.

At column 77, claim 5, line 49, delete "amino residues 44 to 114 of SEQ ID NO: 1" and replace it with --amino residues 44 to 114 of SEQ ID NO: 4--.

At column 78, claim 15, line 37, delete "isolated".

At column 78, claim 26, line 65, delete "isolated".

At column 79, claim 27, line 1, delete "isolated".

Signed and Sealed this
Twenty-second Day of July, 2014

Michelle K. Lee

Michelle K. Lee
*Deputy Director of the United States Patent and Trademark Office*

UNITED STATES PATENT AND TRADEMARK OFFICE

CERTIFICATE OF CORRECTION

PATENT NO. : 8,383,126 B2
APPLICATION NO. : 11/978257
DATED : February 26, 2013
INVENTOR(S) : Mukamolova et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 265 days.

Signed and Sealed this
Fourteenth Day of October, 2014

Michelle K. Lee
*Deputy Director of the United States Patent and Trademark Office*